(12) United States Patent
Deno et al.

(10) Patent No.: US 12,109,031 B2
(45) Date of Patent: *Oct. 8, 2024

(54) SYSTEM AND METHOD FOR LOCAL ELECTROPHYSIOLOGICAL CHARACTERIZATION OF CARDIAC SUBSTRATE USING MULTI-ELECTRODE CATHETER

(71) Applicant: St. Jude Medical, Cardiology Division, Inc., St. Paul, MN (US)

(72) Inventors: D. Curtis Deno, Andover, MN (US); Ram K. Balachandran, Maple Grove, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/593,631

(22) Filed: Oct. 4, 2019

(65) Prior Publication Data
US 2020/0253496 A1 Aug. 13, 2020

Related U.S. Application Data

(63) Continuation of application No. 15/118,522, filed as application No. PCT/US2015/017576 on Feb. 25, 2015, now Pat. No. 10,470,682.

(Continued)

(51) Int. Cl.
*A61B 5/00* (2006.01)
*A61B 5/06* (2006.01)
(Continued)

(52) U.S. Cl.
CPC .............. *A61B 5/287* (2021.01); *A61B 5/062* (2013.01); *A61B 5/068* (2013.01); *A61B 5/316* (2021.01);
(Continued)

(58) Field of Classification Search
CPC .......... A61B 5/287; A61B 5/316; A61B 5/339; A61B 5/341; A61B 5/349; A61B 5/068;
(Continued)

(56) References Cited

U.S. PATENT DOCUMENTS

| 4,649,924 A | 3/1987 | Taccardi |
| 5,297,549 A | 3/1994 | Beatty et al. |

(Continued)

FOREIGN PATENT DOCUMENTS

| CN | 101448454 A | 6/2009 |
| CN | 102118994 A | 7/2011 |

(Continued)

OTHER PUBLICATIONS

Anter, Elad et al.; High-Resolution Mapping of Scar-Related Atrial Arrhythmias Using Smaller Electrodes with Closer Interelectrode Spacing; Circulation; vol. 8; No. 3; Jun. 2015.

(Continued)

*Primary Examiner* — Sana Sahand
(74) *Attorney, Agent, or Firm* — Wiley Rein LLP

(57) ABSTRACT

A system for determining electrophysiological data comprising an electronic control unit configured to acquire electrophysiology signals from a plurality of electrodes (130) of one or more catheters, select at least one clique of electrodes from the plurality of electrodes (136) to determine a plurality of local E field data points, determine the location and orientation of the plurality of electrodes, process the electrophysiology signals from the at least one clique from a full set of bipole subcliques to derive the local E field data points associated with the at least one clique of electrodes, derive at least one orientation independent signal from the at least one clique of electrodes (138) from the information content corresponding to weighted parts of electrogram signals, and display or output catheter orienta- (Continued)

tion independent electrophysiologic information to a user or process.

20 Claims, 33 Drawing Sheets

Related U.S. Application Data

(60) Provisional application No. 61/944,426, filed on Feb. 25, 2014.

(51) Int. Cl.
    *A61B 5/287*     (2021.01)
    *A61B 5/316*     (2021.01)
    *A61B 5/339*     (2021.01)
    *A61B 5/341*     (2021.01)
    *A61B 5/349*     (2021.01)
    *A61B 18/14*     (2006.01)
    *A61M 25/01*     (2006.01)
    *A61B 18/00*     (2006.01)

(52) U.S. Cl.
    CPC .............. *A61B 5/339* (2021.01); *A61B 5/341* (2021.01); *A61B 5/349* (2021.01); *A61B 5/6852* (2013.01); *A61B 5/6858* (2013.01); *A61B 18/1492* (2013.01); *A61M 25/0127* (2013.01); *A61B 5/0044* (2013.01); *A61B 5/7239* (2013.01); *A61B 2018/00577* (2013.01); *A61B 2018/00839* (2013.01); *A61B 2562/0214* (2013.01); *A61B 2562/046* (2013.01); *A61M 2025/0166* (2013.01)

(58) Field of Classification Search
CPC ... A61B 5/6858; A61B 5/0127; A61B 5/6852; A61B 5/062; A61B 5/1492; A61B 5/0044; A61B 5/7239; A61B 2562/046; A61B 2562/0214; A61B 18/1492; A61B 2018/00577; A61B 2018/00839
See application file for complete search history.

(56) References Cited

U.S. PATENT DOCUMENTS

| | | | |
|---|---|---|---|
| 5,487,391 A * | 1/1996 | Panescu | A61N 1/056 |
| | | | 600/512 |
| 5,848,972 A | 12/1998 | Triedman et al. | |
| 5,921,923 A | 7/1999 | Kuck et al. | |
| 6,233,476 B1 | 5/2001 | Strommer et al. | |
| 6,360,121 B1 | 3/2002 | Shoda et al. | |
| 6,400,981 B1 | 6/2002 | Govari | |
| 6,498,944 B1 | 12/2002 | Ben-Haim et al. | |
| 6,546,270 B1 | 4/2003 | Goldin et al. | |
| 6,690,983 B2 | 2/2004 | Ben-Haim et al. | |
| 6,788,967 B2 | 9/2004 | Ben-Heim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 8,862,213 B2 | 10/2014 | Lo et al. | |
| 8,876,817 B2 | 11/2014 | Avitall et al. | |
| 10,470,682 B2 * | 11/2019 | Deno | A61B 5/339 |
| 10,499,826 B2 * | 12/2019 | Balachandran | A61B 5/061 |
| 2002/0055674 A1 * | 5/2002 | Ben-Haim | A61B 5/6858 |
| | | | 600/374 |
| 2003/0100923 A1 * | 5/2003 | Bjorling | A61N 1/3622 |
| | | | 607/9 |
| 2004/0254437 A1 | 12/2004 | Hauck et al. | |
| 2006/0253030 A1 | 11/2006 | Altmann et al. | |
| 2007/0225589 A1 | 9/2007 | Viswanathan | |
| 2008/0221643 A1 | 9/2008 | Olson | |
| 2009/0248014 A1 | 10/2009 | Shachar et al. | |
| 2010/0168557 A1 | 7/2010 | Deno et al. | |
| 2010/0168560 A1 | 7/2010 | Hauck et al. | |
| 2011/0160593 A1 * | 6/2011 | Deno | A61B 5/061 |
| | | | 600/463 |
| 2011/0275949 A1 * | 11/2011 | Harlev | A61B 5/6852 |
| | | | 600/509 |
| 2012/0184865 A1 * | 7/2012 | Harlev | A61B 18/00 |
| | | | 600/509 |
| 2013/0190747 A1 | 7/2013 | Koblish et al. | |
| 2013/0274582 A1 * | 10/2013 | Afonso | A61B 5/065 |
| | | | 600/374 |
| 2014/0058375 A1 | 2/2014 | Koblish | |
| 2014/0180152 A1 * | 6/2014 | Maskara | A61B 18/1492 |
| | | | 600/509 |
| 2014/0336518 A1 | 11/2014 | Shuros et al. | |
| 2016/0174865 A1 * | 6/2016 | Stewart | A61B 5/316 |
| | | | 600/374 |

FOREIGN PATENT DOCUMENTS

| | | | | |
|---|---|---|---|---|
| CN | 103354730 A | | 10/2013 | |
| CN | 103565432 A | | 2/2014 | |
| EP | 1166714 | | 1/2002 | |
| EP | 1166714 A1 * | | 1/2002 | ............... A61B 5/06 |
| EP | 1336379 | | 8/2003 | |
| EP | 2186474 | | 5/2010 | |
| JP | 11047148 A | | 2/1999 | |
| JP | 2001-37730 A | | 2/2001 | |
| JP | 2001-061789 | | 3/2001 | |
| JP | 2002-051998 | | 2/2002 | |
| JP | 2002-65626 A | | 3/2002 | |
| JP | 2007537831 A | | 12/2007 | |
| JP | 2012524606 A | | 10/2012 | |
| WO | 1997/024983 | | 7/1997 | |
| WO | 2012/037471 | | 3/2012 | |
| WO | WO-2012037471 A2 * | | 3/2012 | ........... A61B 5/6823 |
| WO | 2012/092016 | | 7/2012 | |
| WO | WO-2012092016 A1 * | | 7/2012 | ......... A61B 18/1492 |
| WO | 2014/113612 | | 7/2014 | |
| WO | 2014/182822 | | 11/2014 | |

OTHER PUBLICATIONS

Arora, Rishi et al.; "Fundamentals of Intracardiac Mapping"; Catheter Ablation of Cardiac Arrhythmias; pp. 107-134; 2006.
Avitall, Boaz et al.; "Maximal Electrogram Attenuation Recorded from Mini Electrodes Embedded on 4.5-mm Irrigated and 8-mm Nonirrigated Catheters Signifies Lesion Maturation"; Journal of Cardiovascular Electrophysiology; vol. 26; No. 2; Feb. 2015.
Balasundaram, Krishnanand et al.; "Tracking Rotors with Minimal Electrodes: Modulation Index Based Strategy"; Circulation; vol. 8; No. 2; Apr. 2015.
Barnette, AR et al.; "Estimation of a 3-D Conduction Velocity Vector Fields from Cardiac Mapping Data"; Computers in Cardiology; vol. 25; pp. 605-608; Sep. 1998.
Bayly, Philip V. et al.; "Estimation of Conduction Velocity Vector Fields from Epicardial Mapping Data"; IEEE Transactions on Biomedical Engineering; vol. 45; No. 5; pp. 563-569; May 1998.
Bayly, PV et al.; "Estimation of Conduction Velocity Vector Fields from 504-Channel Epicardial Mapping Data"; Computers in Cardiology; pp. 133-136; Sep. 1996.
Benharash, Peyman et al.; "Quantitative Analysis of Localized Sources Identified by Focal Impulse and Rotor Modulation Mapping in Atrial Fibrillation"; Circulation; pp. 554-561; Jun. 2015.
Bharati, Saroja et al.; "The Conduction System of the Swine Heart": Chest; vol. 100; No. 1; pp. 207-212; Jul. 1991.
Bortone, Agustin et al.; "Unipolar Signal Modification as a Guide for Lesion Creation During Radiofrequency Application in the Left Atrium Prospective Study in Humans in the Setting of Paroxysmal Atrial Fibrillation Catheter Ablation"; Circulation; pp. 1096-1102; Dec. 2013.
Bouman, L.N. et al.; "Structure and Function of the Sino-Atrial Node: A Review"; European Heart Journal; vol. 7; No. 2; pp. 94-104, Feb. 1986.
Boyelt, M.R. et al.; "The Sinoatrial Node, a Heterogeneous Pacemaker Structure"; Cardiovascular Research; vol. 47; No. 4; Sep. 2000.

(56) References Cited

OTHER PUBLICATIONS

Burch, George E. et al.; "Chapter X the Development of Spatial Vectrocardiography"; A History of Electrocardiography; Norman Publishing: pp. 235-248; Apr. 1990.

Cantwell, C.D. et al.; "Techniques for Automated Local Activation Time Annotation and Conduction Velocity Estimation in Cardiac Mapping", Computers in Biology and Medicine; Oct. 1, 2015.

Casella, Michela et al. "Feasibility of Combined Unipolar and Bipolar Voltage Maps to Improve Sensitivity of Endomycardial Biopsy"; Circulation; Jun. 2015.

Chan, Rodrigo C. et al.; "The Effect of Ablation Length and Catheter Tip to Endocardial Orientation on Radiofrequency Lesion Size in the Canine Right Atrium"; PACE; vol. 25; No. 1; Jan. 2002.

Damle, Roger S.; "Atrial and Accessory Pathway Activation Direction in Patients with Orthodromic Supraventricular Tachycardia: Insights from Vector Mapping" JACC; vol. 23; No. 3; pp. 664-692; Mar. 1, 1994.

De Bakker, Jacques M.T. et al.; "The Pathophysiologic Basis of Fractionated and Complex Electrograms and the Impact of Recording Techniques on Their Detection and Interpretation"; Circulation; vol. 3, No. 2; Apr. 2010.

De Bakker, Jacquest M.T. et al.; "Activation Mapping: Unipolar Versus Bipolar Recording"; Cardiac Electrophysiology from Cell to Bedside Second Edition: pp. 1088-1078; Jan. 28, 1995.

Deng, Dong-dong et al.; "Simulation of Blatrial Conduction via Different Pathways during Sinus Rhythm with a Detailed Human Atrial Model"; Journal of Zhjlang University-Science B (Biomedicine & Biotechnology; pp. 676-694; Sep. 2012.

Deng, Dongdong et al.; "An Image-Based Model of the Whole Human Heart with Detailed Anatomical Structure and Fiber Orientation"; Computational and Mathematical Methods in Medicine; vol. 2012; Jul. 2012.

Desai, Jawahar M. et al.; "Two Phase Radiofrequency Catheter Ablation of Isolated Ventricular Endomyocardium"; PACE, vol. 14, pp. 1179-1194; Jul. 1991.

Dubois, R. et al.; "Global and Directional Activation Maps for Cardiac Mapping in Electrophysiology"; Computing in Cardiology; pp. 349-352; Sep. 2012.

Faes, Luca et al.; "A Method for Quantifying Atrial Fibrillation Organization Based on Wave-Morphology Similarity"; IEEE Transactions on Biomedical Engineering: vol. 49; No. 12: pp. 1504-1513; Dec. 2002.

Fedotov, N.M. et al.; "Methods for increasing the Reliability of Coordinate Determination by the Location and Imaging Systems of Endocardial Electrodes"; Biomedical Engineering: vol. 41, No. 4; pp. 145-149; Jul. 1, 2007.

Fisher, Westby G. et al.; "Three-Dimensional Electrogram Mapping Improves Ablation of Left-Sided Accessory Pathways"; PACE; vol. 15; pp. 2344-2356; Dec. 1992.

Fitzgerald, Tamara N. et al.; "Comparative Psychometric Analysis of Vector and isochrone Cardiac Activation Maps"; IEEE Transactions on Biomedical Engineering: vol. 51; No. 5; pp. 847-855; May 2004.

Fitzgerald, Tamara N. et al.; "Estimation of Cardiac Conduction Velocities Using Small Data Sets"; Annals of Biomedical Engineering; vol. 31; pp. 250-261; Mar. 2003.

Fitzgerald, Tamara N. et al.; "Identification of Cardiac Rhythm Features by Mathematical Analysis of Vector Fields"; IEEE Transactions on Biomedical Engineering; vol. 52: No. 1; pp. 19-29, Jan. 2005.

Gaudette, RJ et al.; "Epicardiai Velocity Estimation Using Wavelets"; Computers in Cardiology; vol. 24; pp. 339-342; Sep. 7, 1997.

Gerstenfeld, Edward P. et al.; "Detection of Changes in Atrial Endocardial Activation with Use of an Orthogonal Catheter"; JACC; vol. 18; No. 4; pp. 1034-1042; Oct. 1991.

Gerstenfeld, Edward P. et al.; "Evidence for Transient Linking of Atrial Excitation During Atrial Fibrillation in Humans"; Circulation; vol. 86; No. 2; pp. 375-382; Aug. 1992.

Gornick, Charles C. et al.; "Validation of a New Noncontact Catheter System for Electroanatomic Mapping of Left Ventricular Endocardium": Circulation; pp. 828-836; Feb. 16, 1999.

Gupta, Sanjaya et al.; "Rapid Ablation of Recurrent Atrial Flutter Using a Novel Ablation Catheter"; The Journal of Innovations in Cardiac Rhythm Management; No. 5; pp. 1808-1812; Nov. 2014.

Haddad, El et al.; "Novel Algorithmic Methods in Mapping of Atrial and Ventricular Tachycardia"; Circulation; Jun. 2014.

Harrild, David M. et al.; "A Computer Model of Normal Conduction in the Human Atria": Circulation Research; Sep. 29, 2000.

Homer, S.M. et al.; "Electrode for Recording Direction of Activation, Conduction Velocity, and Monophasic Action Potential of Myocardium", the American Physiological Society; pp. H1917-H1927; Apr. 1997.

Huang, Jian et al.; "Evolution of the Organization of Epicardial Activation Patterns During Ventricular Fibrillation"; Journal of Cardiovascular Electrophysiology; vol. 9, No. 12; Dec. 1998.

Ideker, Raymond E. et al.; "The Assumptions of Isochronal Cardiac Mapping": PACE; vol. 12; pp. 456-478; Mar. 1989.

Irie, Tadanobu et al.; "Relationship Between Sinus Rhythm Late Activation Zones and Critical Sites for Scar-Related Ventricular Tachycardia: a Systematic Analysis of Isochronal Late Activation Mapping"; Circulation; Apr. 2015.

Kadish, Alan et al . . . ; "Mapping of Atrial Activation with a Noncontact, Multielectrode Catheter in Dogs"; Circulation; pp. 1906-1913; Apr. 13, 1999.

Kadish, Alan H. et al.; "Vector Mapping of Myocardial Activation"; Circulation; vol. 74; No. 3; pp. 603-615; Sep. 1986.

Karney, Charles F.F. et al.; "Quaternions in Molecular Modeling"; Journal of Molecular Graphics and Modeling; pp. 595-604; Jan. 2007.

Kay, Matthew W. et al.; "Measuring Curvature and Velocity Vector Fields for Waves of Cardiac Excitation in 2-D Media"; IEEE Transactions on Biomedical Engineering: vol. 52; No. 1; pp. 50-63; Jan. 2005.

Kearsley, Simon K.; "On the Orthogonal Transformation Used for Structural Comparisons"; Acta Crystallographica Section A; A45; pp. 208-210; Feb. 1, 1989.

Kumar, Saurabh et al.; Unipolar Electrogram Morphology to Assess Lesion Formation During Catheter Ablation of Atrial Fibrillation Successful Translation into Clinical Practice; Circulation; pp. 1050-1052; Dec. 2013.

Lindsay, Bruce D. et al.; "Novel Directional Activation Map Using Local Propagation Between Adjacent Electrograms"; Heart Rhythm; vol. 8; No. 5; May Supplement 2011.

Liu, Chenguang et al.; "Three-Dimensional Imaging of Ventricular Activation and Electrograms from Intracavity Recordings", IEEE Transactions on Biomedical Engineering; vol. 58; No. 4; pp. 868-875; Apr. 2011.

Liu, Tu-Ying et al.; "Functional Characterization of the Crista Terminalis in Patients with Atrial Flutter: Implications of Radiofrequency Ablation"; JACC; vol. 43; No. 9: pp. 1639-1645; May 5, 2004.

Masse, M. et al.; "Velocity Field Analysis of Activation Maps in Atrial Fibrillation a Simulation Study"; World Congress on Medical Physics and Biomedical Engineering: vol. 25/4; pp. 1014-1017; Sep. 2009.

Mazeh, Nachaat et al.; "A Simplified Approach for Simultaneous Measurements of Wavefront Velocity and Curvature in the Heart Using Activation Times"; Cardiovascular Engineering and Technology: vol. 4; No. 4; Dec. 2013.

Michaud, Gregory F. et al.; "Information at our Catheter Tips: Unipolar Electrogram Morphology Makes another Comeback!"; Heart Rhythm; vol. 7; No. 9: pp. 1301-1302; Sep. 2010.

Mironov, Sergey et al.; "Role of Conduction Velocity Restitution and Short-Term Memory in the Development of Action Potential Duration Alternans in Isolated Rabbit Hearts"; Circulation; pp. 17-25; Jul. 1, 2008.

Mountantonakis, Stavros E. et al.; "Relationship between Voltage Map "Channels" and the Location of Critical Isthmus Sites in Patients with Post-Infarction Cardiomyopathy and Ventricular Tachycardia"; JACC; vol. 61; No. 20; pp. 2088-2095; May 21, 2013.

(56) References Cited

OTHER PUBLICATIONS

Nanthakumar, Kumaraswamy et al.; "Regional Differences in Ventricular Fibrillation in the Open-Chest Porcine Left Ventricle"; Circulation Research; pp. 734-740, Oct. 18, 2002.

Narayan, Sanjiv M. et al.; "Treatment of Atrial Fibrillation by the Ablation of Localized Sources"; JACC; vol. 60; No. 7; pp. 628-636; Aug. 14, 2012.

Nayyar, Sachin et al.; "High-Density Mapping of Ventricular Scar a Comparison of Ventricular Tachycardia (VT) Supporting Channels with Channels that do not Support VT"; Circulation; pp. 90-98, Feb. 2014.

Otomo, Kiyoshi et al.; "Local Unipolar and Bipolar Electrogram Criteria for Evaluating the Transmurality of Atrial Ablation Lesions at Different Catheter Orientations Relative to the Endocardial Surface", Heart Rhythm; vol. 7; No. 9; pp. 1291-1300; Sep. 2010.

Parson, Ian D. et al.; "Cardiac Mapping Instrumentation for the Instantaneous Display of Endocardial and Epicardial Activation"; IEEE Transactions on Biomedical Engineering; vol. BME-34; No. 6; pp. 468-472; Jun. 1987.

Patel, Parin J. et al.; "Electroanatomic Mapping of the Intercaval Bundle in Atrial Fibrillation"; Circulation; pp. 1262-1267; Dec. 2014.

Pieper, Carl F. et al.; "Simultaneously Collected Monopolar and Discrete Bipolar Electrograms: Comparison of Activation Time Detection Algorithms"; PACE; vol. 16; pp. 426-433; Mar. 1993.

Plank, G. et al.; "Cardiac Near-Field Morphology During Conduction Around a Microscopic Obstacle—a Computer Simulation Study"; Annals of Biomedical Engineering; vol. 31; No. 10; pp. 1206-1212; Nov. 2003.

Plank, G. et al.; "Model Study of Vector-Loop Morphology During Electrical Mapping of Microscopic Conduction in Cardiac Tissue"; Annals of Biomedical Engineering; vol. 28; No. 10; pp. 1244-1252; Oct. 2000.

Plank, G. et al.; "Use of Cardiac Electric Near-Field Measurements to Determine Activation Times"; Annals of Biomedical Engineering; vol. 31; No. 9; pp. 1066-1076; Oct. 2003.

Price, Adam et al.; "Novel Ablation Catheter Technology that Improves Mapping Resolution and Monitoring of Lesion Maturation"; The Journal of Innovations in Cardiac Rhythm Management; pp. 599-609; Jan. 2012.

Ravelli, Flavia et al.; "Wave Similarity Mapping Shows the Spatiotemporal Distribution of Fibrillatory Wave Complexity in the Human Right Atrium During Paroxysmal and Chronic Atrial Fibrillation"; Journal of Cardiovascular Electrophysiology; vol. 16; No. 10; pp. 1071-1076; Oct. 2005.

Rogers, Jack M. et al.; "Quantitative Techniques for Analyzing High-Resolution Cardiac-Mapping Data"; IEEE Engineering in Medicine and Biology: vol. 17, No. 1; pp. 62-72; Jan. 1, 1998.

Schilling, Richard J. et al.; "Simultaneous Endocardial Mapping in the Human Left Ventricle Using a Noncontact Catheter"; Circulation; pp. 887-898; Sep. 1, 1998.

Schmitt, Otto H. et al.; "Symposium on Electrocardiography and Vectorcardiography the Present Status of Vectorcardiography"; JAMA Internal Medicine; vol. 96; No. 5; pp. 574-590; Nov. 1955.

Schuler, S. et al.; "Influence of Catheter Orientation, Tissue Thickness and Conduction Velocity on the Intracardiac Electrogram"; Biomedizinische Technik/Biomedical Engineering; Sep. 2013.

Schumacher, Burghard et al.; "Transverse Conduction Capabilities of the Crista Terminalis in Patients with Atrial Flutter and Atrial Fibrillation"; JACC; vol. 34; No. 2; pp. 363-373; Aug. 1999.

Shors, Stephanie M. et al. "A method for Determining High-Resolution Activation Time Delays in Unipolar Cardiac Mapping"; IEEE Transactions on Biomedical Engineering, vol. 43; No. 12; pp. 1192-1196; Dec. 1996.

Spears, Danna A. et al.; "Relationship of Bipolar and Unipolar Electrogram Voltage to Scar Transmurality and Composition Derived by Magnetic Resonance Imaging in Patients with Nonischemic Cardiomyopathy Undergoing VT Ablation"; Heart Rhythm; vol. 9. No. 11; pp. 1837-1846; Nov. 2012.

Stevenson, William G. et al.; "Recording Techniques for Clinical Electrophysiology"; Journal of Cardiovascular Electrophysiology; vol. 16; No. 9; pp. 1017-1022; Sep. 2005.

Tedrow, Usha B. et al.; "Recording and Interpreting Unipolar Electrograms to Guide Catheter Ablation"; Heart Rhythm; vol. 8; No. 5; pp. 791-796; May 2011.

Thompson, Nathaniel C. et al.; "Improved Spatial Resolution and Electrogram Wave Direction Independence with the Use of an Orthogonal Electrode Configuration" J Clin Monit Comput; pp. 167-163; Apr. 2014.

Tungjitkusolmun, Supan et al.; "Guidelines for Predicting Lesion Size at Common Endocardial Locations During Radio-Frequency Ablation"; IEEE Transactions on Biomedical Engineering, vol. 48; No. 2; pp. 194-201; Feb. 2001.

Weber, Frank M. et al.; "Conduction Velocity Restitution of the Human Atrium—An Efficient Measurement Protocol for Clinical Electrophysiological Studies", IEEE Transactions on Biomedical Engineering; vol. 58; No. 9; pp. 2648-2655; Sep. 2011.

Weber, Frank M. et al.; "Wave-Direction and Conduction-Velocity Analysis from Intracardiac Electrograms—a Single-Shot Technique"; IEEE Transactions on Biomedical Engineering; vol. 57; No. 10; pp. 2394-2401; Oct. 2010.

Witkowski, Francis X. et al.; "In Vivo Estimation of Cardiac Transmembrane Current"; Circulation Research; vol. 72; No. 2; pp. 424-439; Feb. 1993.

Yamada, Takumi et al.; "Electrophysiological Pulmonary Vein Antrum Isolation with a Multielectrode Basket Catheter is Feasible and Effective for Curing Paroxysmal Atrial Fibrillation: Efficacy of Minimally Extensive Pulmonary Vein Isolation"; Heart Rhythm, vol. 3; No. 4; pp. 377-384; Apr. 2006.

Yamada, Takumi; "Pulmonary Vein Isolation with a Multielectrode Basket Cather"; Indian Pacing and Electrophysiology Journal; pp. 97-109; Apr. 2007.

Zaman, Junaid, A.B. et al.; "The Rofor Revolution Conduction at the Eye of the Storm in Atrial Fibrillation"; Circulation; pp. 1230-1236; Dec. 2014.

Zhang, Xin et al.; "Noninvasive Three-Dimensional Electrocardiographic Imaging of Ventricular Activation Sequence"; AJP-Heart Circ Physiol; vol. 289; pp. H2724-2732; Aug. 5, 2005.

* cited by examiner

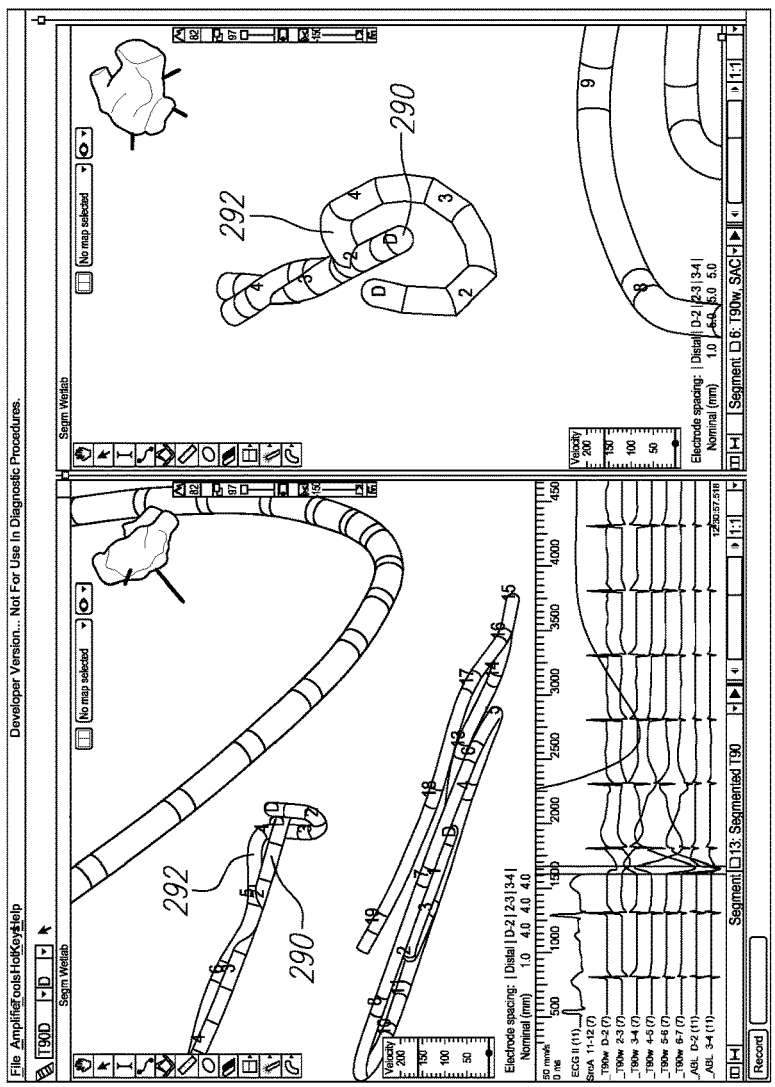
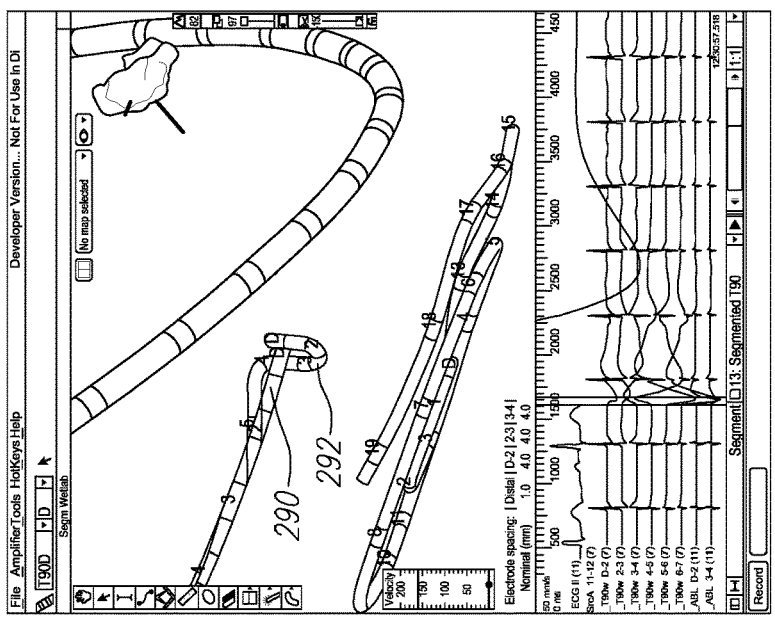
FIG. 12A
FIG. 12B

|  | P(θ) | CURL | DIV |
|---|---|---|---|
| Uniform Propagation | Strong and eccentric | Small | Small |
| Rotors | Weak | Large | Small |
| Focal Source | Weak | Small | Large and Positive |
| Collision Site | Weak | Small | Large and Negative |
| Scar | Weak | Small | Small |

370 — Uniform Propagation
371 — Rotors
372 — Focal Source
373 — Collision Site
374 — Scar

FIG. 16

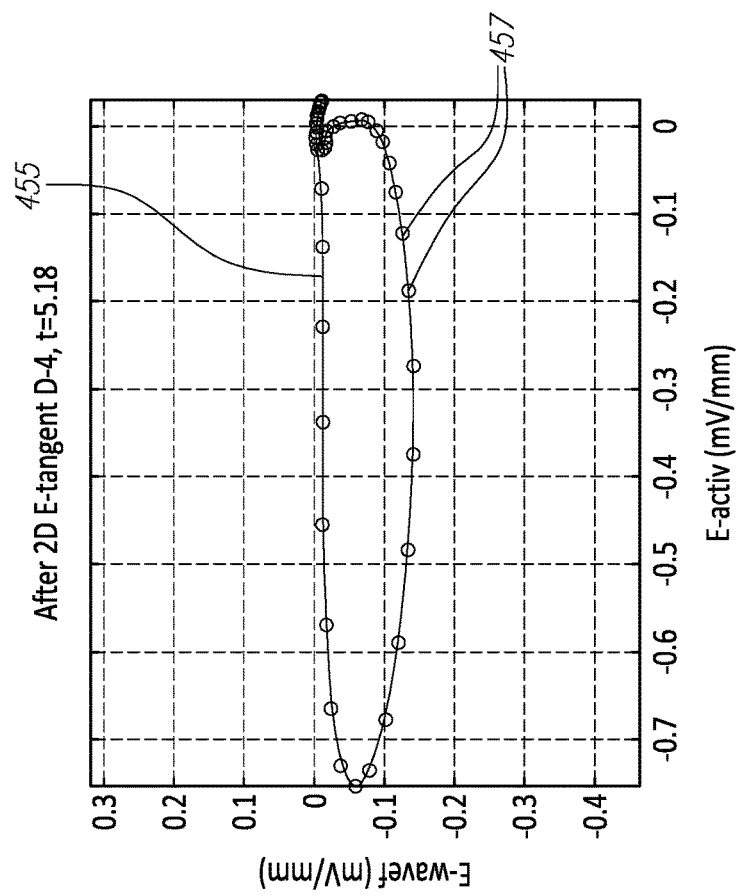
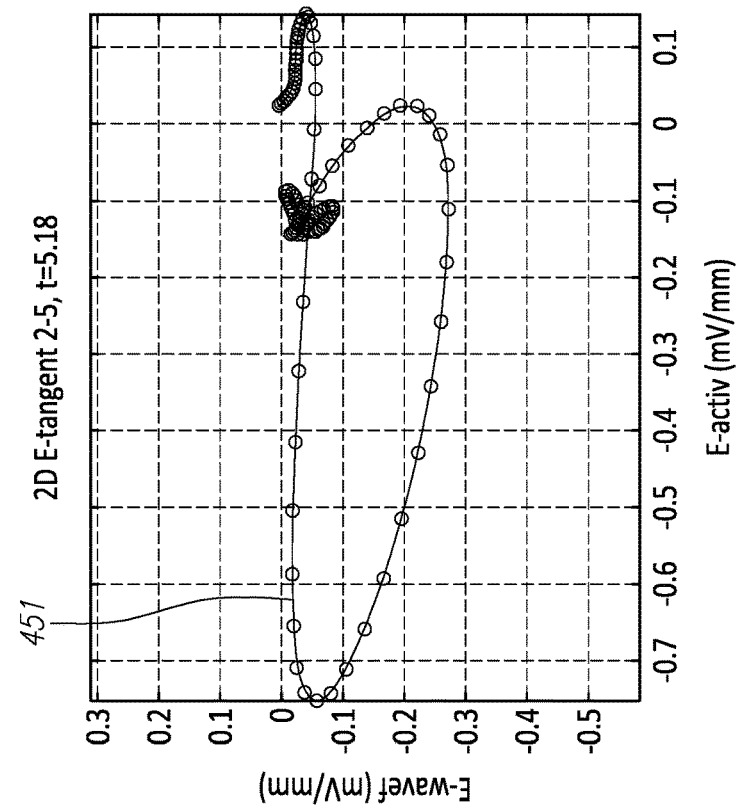
FIG. 24B
FIG. 24A

SYSTEM AND METHOD FOR LOCAL ELECTROPHYSIOLOGICAL CHARACTERIZATION OF CARDIAC SUBSTRATE USING MULTI-ELECTRODE CATHETER

CROSS-REFERENCE TO RELATED APPLICATIONS

This application is a continuation of U.S. application Ser. No. 15/118,522, filed 12 Aug. 2016 (the '522 application), now U.S. Pat. No. 10,470,682, which is a national stage filing based upon international application no. PCT/US2015/017576, filed 25 Feb. 2015 (the '576 application), which claims the benefit of U.S. provisional application No. 61/944,426, filed 25 Feb. 2014 (the '426 application). The '522 application, the '576 application and the '426 application are all hereby incorporated by reference in their entirety as though fully set forth herein.

BACKGROUND a. Field

This disclosure relates to systems, apparatuses and methods for utilizing electrode spatial arrangements within a mapping system. In particular, the instant disclosure relates to systems, apparatuses and methods for characterizing cardiac conduction conditions in a catheter orientation independent manner using electrode spatial arrangements in 3D mapping systems.

b. Background

Electrophysiology (EP) catheters are used in a variety of diagnostic, therapeutic, and/or mapping and ablative procedures to diagnose and/or correct conditions such as atrial or ventricular arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, a catheter is deployed and manipulated through a patient's vasculature to the intended site, for example, a site within a patient's heart. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue. This lesion disrupts undesirable cardiac activation pathways and thereby limits, corrals, or prevents errant conduction signals that can form the basis for arrhythmias.

To position a catheter at a desired site within the body, some type of navigation may be used, such as using mechanical steering features incorporated into the catheter (or a sheath). In some examples, medical personnel may manually manipulate and/or operate the catheter using the mechanical steering features.

A navigating system may be used for visualization and to facilitate the advancement of catheters through a patient's vasculature to specific locations within the body. Such navigating systems may include, for example, electric and/or magnetic field based positioning and navigating systems that are able to determine the position and orientation of the catheter (and similar devices) within the body.

Conduction disorders in the body can result from abnormal conduction in regions as small as 1-4 mm. In addition, ablation in these regions must be restricted to the pathological tissue to preserve electrical and mechanical function, particularly with ventricular arrhythmias. Today, many catheters employ electrode pairs spaced greater than 4 mm apart which can make it difficult to reliably allow discrimination or localization of defects. Even when the electrodes are more closely spaced, around 1 mm to around 2 mm, the orientation of the pair of electrodes is a prominent factor in the amplitude and morphology of the resulting signals.

The foregoing discussion is intended only to illustrate the present field and should not be taken as a disavowal of claim scope.

BRIEF SUMMARY

In an embodiment, a system for determining electrophysiological data comprises an electronic control unit configured to receive electrogram data for a set of electrodes, receive position and orientation information for the set of electrodes from a mapping system, determine catheter orientation independent information of a tissue, and output the orientation independent information to the mapping system. In some embodiments, the electrode arrangements facilitate multiple simultaneous such assessments and the mapping system may process the spatial pattern of catheter orientation independent information to recognize certain arrhythmia patterns.

In one embodiment, a system for determining electrophysiological data can comprise an electronic control unit configured to acquire electrophysiology signals from a plurality of electrodes of one or more catheters, select at least one clique of electrodes from the plurality of electrodes to determine a plurality of local E field data points, determine the location and orientation of the plurality of electrodes, process the electrophysiology signals from the at least one clique from a full set of bipole subcliques to derive the local E field data points associated with the at least one clique of electrodes, derive at least one orientation independent signal from the at least one clique of electrodes from the information content corresponding to weighted parts of electrogram signals, and display or output catheter orientation independent electrophysiologic information to a user or process.

In another embodiment, a method for determining electrophysiological data can comprise acquiring electrophysiology signals from a plurality of electrodes of one or more catheters, selecting at least one clique of electrodes from the plurality of electrodes to determine a plurality of local E field data points, determining the location and orientation of the plurality of electrodes, processing the electrophysiology signals from the at least one clique from a full set of bipole subcliques to derive the local E field data points associated with the at least one clique of electrodes, deriving at least one orientation independent signal from the at least one clique of electrodes from the information content corresponding to weighted parts of electrogram signals, and displaying or output catheter orientation independent electrophysiologic information to a user or process.

In yet another embodiment, a circuit box adapter can comprise circuitry to interface an electrode ablation catheter to both an RF generator and EP mapping system; the circuitry operable between a first state to allow a plurality of catheter electrodes to separately sense electrical signals in a first mode and a second state to emit energy from a single output from an ablation generator in a second mode. In the first state, the circuitry is configured to allow passive isolation of the plurality of segmented catheter electrodes for operation in the first mode.

BRIEF DESCRIPTION OF THE DRAWINGS

FIGS. 12A and 12B are mapping system images illustrating the effectiveness of the switch box circuit before and during RF respectively.

FIG. 16 is a table showing the characteristic values and shapes expected for determining tissue characteristics.

FIGS. 24A and 24B are graphs showing the tangent E-field loop before and after weighting the loop points based on the norm of the E-field.

DETAILED DESCRIPTION

Cardiac EP mapping today primarily uses bipolar electrograms (EGMs) obtained from electrode pairs. Bipoles are preferred as they have reduced low frequency noise, reduced far-field effects and often produce sharp and well-recognized features when filtered appropriately. Unipolar EGMs on the other hand contain far-field information and less stable baselines that make them less attractive for mapping purposes. A feature of the unipolar signal that makes it useful for mapping is the fact that its morphology and amplitude are independent of catheter orientation. Amplitudes and morphology of bipolar EGM's are dependent on the orientation of the electrode pair from which they are calculated and hence depend on the orientation of the catheter. The dependence on orientation results in inconsistently measured amplitudes and morphology-based measurements like activation times. It therefore also impacts derived quantities like scar boundaries, activation direction, and conduction velocity.

Electrophysiologic information may also be elicited by pacing a tissue or organ and observing the resulting spread of depolarization from immediately adjacent to the site where capture occurs. These observations are difficult with current technology because of pacing artifacts but directional information provided by $E_n$, $E_a$, or v, as described herein, can serve as clues to anatomic or functional conduction blocks. Even without pacing, conduction around obstacles such as valve orifices or blocks is known to become curved and slowed and this can be directly mapped and visualized with the information disclosed herein much more conveniently and reliably than previously possible.

Figure 1:
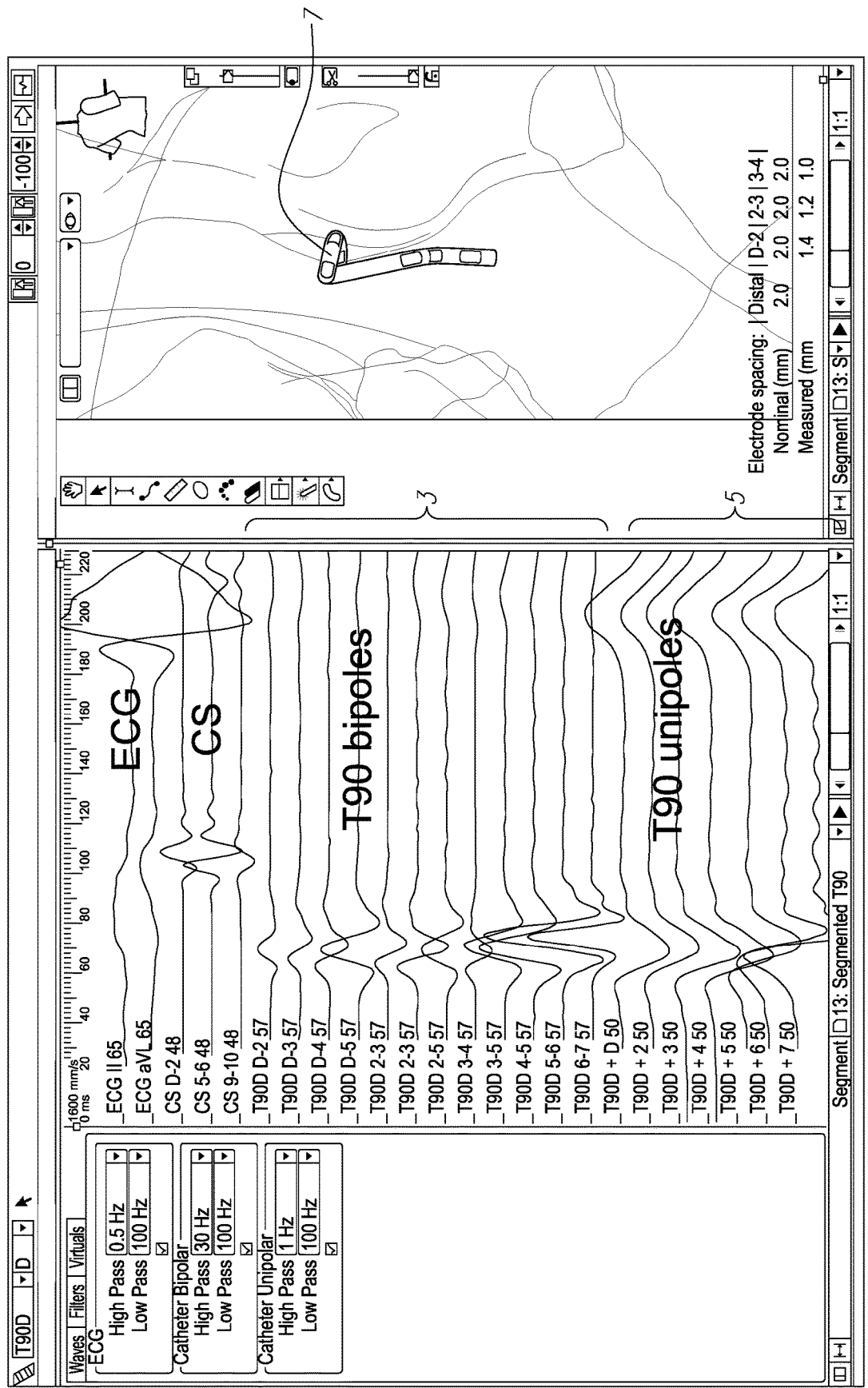
FIG. 1 is an illustration of the morphology and amplitudes of bipoles obtained from a catheter.

FIG. 1 depicts the variability in the morphology and amplitudes of a plurality of bipole signals 3 obtained from a catheter 7 in the right atrium of a heart. A plurality of unipolar signals 5 also acquired from the catheter 7 have very similar morphology and amplitudes but they are contaminated by far field ventricular depolarization.

One aspect described herein addresses a unique way to combine the benefit of orientation independence of the unipolar signals with the other benefits of bipolar signals that were highlighted previously. The disclosure utilizes closely spaced electrodes on high-density diagnostic catheters to derive local "pseudo bipolar", "equivalent bipole", or "omnipolar" signals that are orientation independent and are free of low-frequency noise and far-field effects. The closely spaced electrodes can be located on a single high-density diagnostic or other catheter or in some embodiments can be located on multiple catheters where electrodes on the catheters are located near or adjacent each other. Furthermore, the equivalent bipolar EGMs so derived possess characteristic shapes and relationships that reflect physiologic and anatomic directions which enable better contact maps by virtue of more consistent activation timing directions. The presence of closely spaced electrodes also helps to characterize the substrate in the immediate vicinity (few mm) of the catheter. The omnipolar electrogram signal's amplitude and morphology would only be a function of the local substrate's electrophysiology and hence lends itself to the creation of better, consistent, and more useful contact maps. Examples of high-density catheters that can be used for the purpose include (but are not limited to) the catheters shown in FIG. 2, and basket catheters like the catheters shown in FIG. 3 and FIG. 9.

Figure 2A:
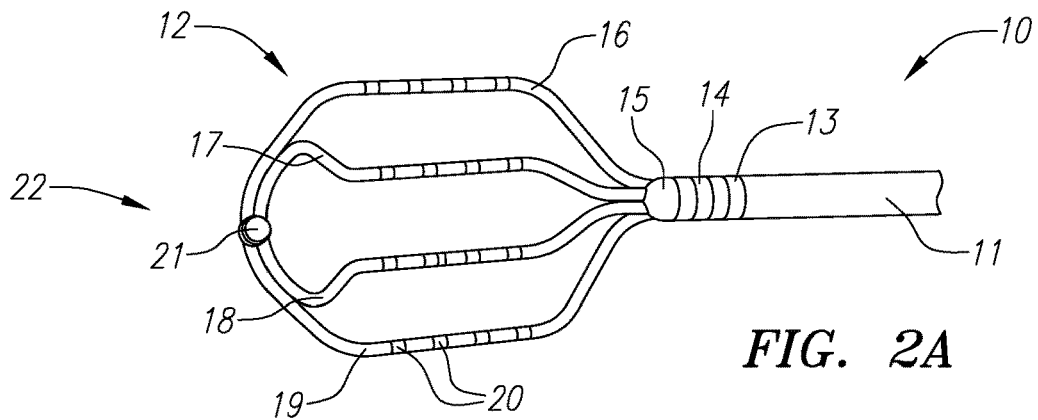
FIG. 2A is an isometric view of one embodiment of a paddle catheter.
Figure 2B:
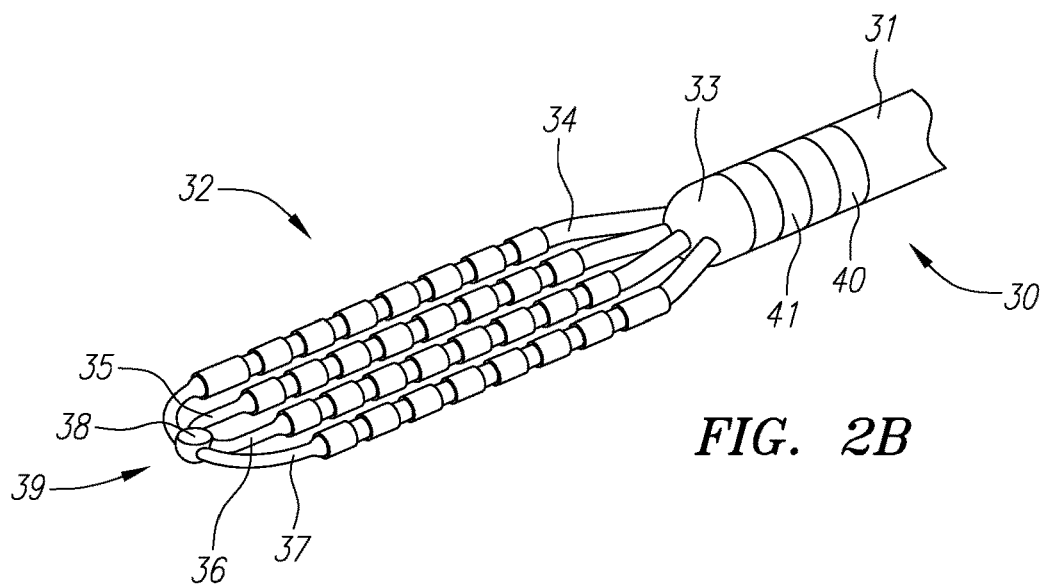
FIG. 2B is an isometric view of another embodiment of a paddle catheter.
Figure 2C:
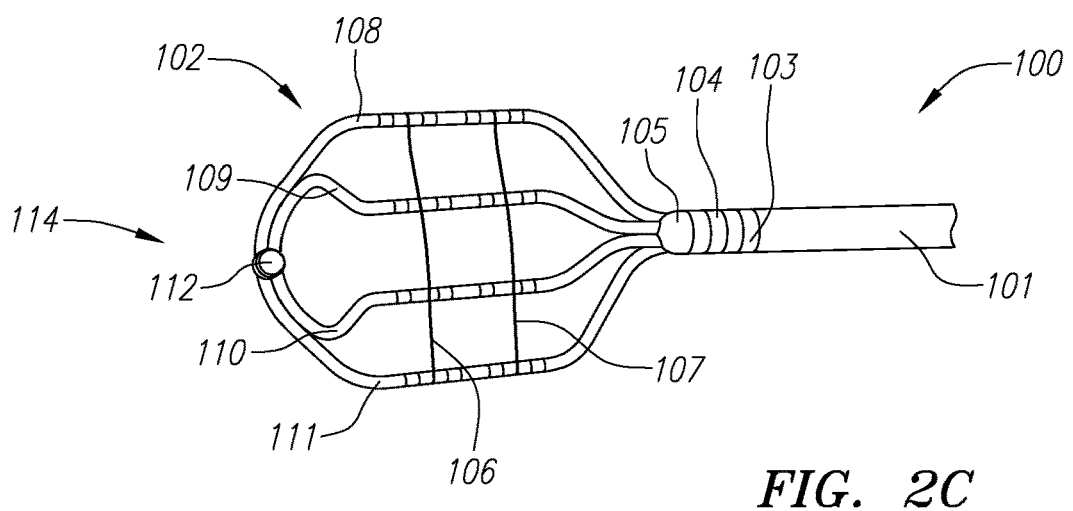
FIG. 2C is an isometric view of another embodiment of a paddle catheter.

FIGS. 2A-2C show embodiments of catheters that can be used for HD mapping applications. FIG. 2A illustrates one embodiment of a catheter 10 comprising a catheter body 11 coupled to a paddle 12. The catheter body 11 can further comprise a first body electrode 13 and a second body electrode 14. The paddle 12 can comprise a first spline 16, a second spline 17, a third spline 18, and a fourth spline 19 that are coupled to the catheter body 11 by a proximal coupler 15 and coupled to each other by a distal connector 21 at a distal end of the paddle 22. In one embodiment the first spline 16 and the fourth spline 19 can be one continuous segment and the second spline 17 and the third spline 18 can be another continuous segment. In other embodiments the various splines can be separate segments coupled to each other. The plurality of splines can further comprise a varying number of electrodes 20. The electrodes in the illustrated embodiment can comprise ring electrodes evenly spaced along the splines. In other embodiments the electrodes can be evenly or unevenly spaced and the electrodes can comprise point or other types of electrodes. FIG. 2B illustrates another embodiment of a catheter 30 that can be used for HD mapping applications. The catheter 30 can comprise a catheter body 31 coupled to a paddle 32. The catheter body 31 can further comprise a first body electrode 40 and a second body electrode 41. The paddle 32 can comprise a first spline 34, a second spline 35, a third spline 36, and a fourth spline 37 that are coupled to the catheter body 31 by a proximal coupler 33 and coupled to each other by a distal connector 38 at a distal end of the paddle 39. In one embodiment, the proximal coupler 33 can further comprise an electrode.

Electrode placement along splines is controlled by the good mechanical stability of electrodes on splines. As a result, spacing along splines is best determined not by the mapping system, but by design and manufacturing. But spacing between splines is variable as a result of the forces and torques experienced as a catheter is maneuvered to a desired location. Electrodes located in spline midsections are most vulnerable to displacement. FIG. 2C shows incorporating slender tensile elements configured to join the splines near their centers to limit the maximal displacement from one another. One means to accomplish this is to use slender mono or multifilament nylon thread or suture like material, fastened at the ends, and looping around splines in the middle. A pass through a reflow oven during production allows the threads to become incorporated into the spline's polymer insulation, securing the thread to each spline and minimizing protuberances.

FIG. 2C illustrates one embodiment of a catheter 100 using tethers to limit the maximal spread between splines and thus enforce a more consistent electrode spacing when in use. The catheter 100 can comprise a catheter body 101 coupled to a paddle 102. The catheter body 101 can further comprise a first body electrode 103 and a second body electrode 104. The paddle 102 can comprise a first spline 108, a second spline 109, a third spline 110, and a fourth spline 111 that are coupled to the catheter body 101 by a proximal coupler 105 and coupled to each other by a distal connector 112 at a distal end of the paddle 114. The paddle 102 can further comprise a first support member 106 and a second support member 107 to limit displacement of the splines from each other. These support members can be slender tensile elements (like threads or suture material) that collapse during insertion of the catheter 100 into a sheath. The catheters shown in FIGS. 2A, 2B, and 2C are further described in international application no. PCT/US2014/011, 940 filed 16 Jan. 2014 and published in English on 24 Jul. 2014 under international publication no. WO 2014/113612 (the '612 application) and U.S. provisional application No. 61/753,429, filed 16 Jan. 2013 (the '429 application). The '612 application and the '429 applications are both hereby incorporated by reference in their entirety as though fully set forth herein.

Figure 3:
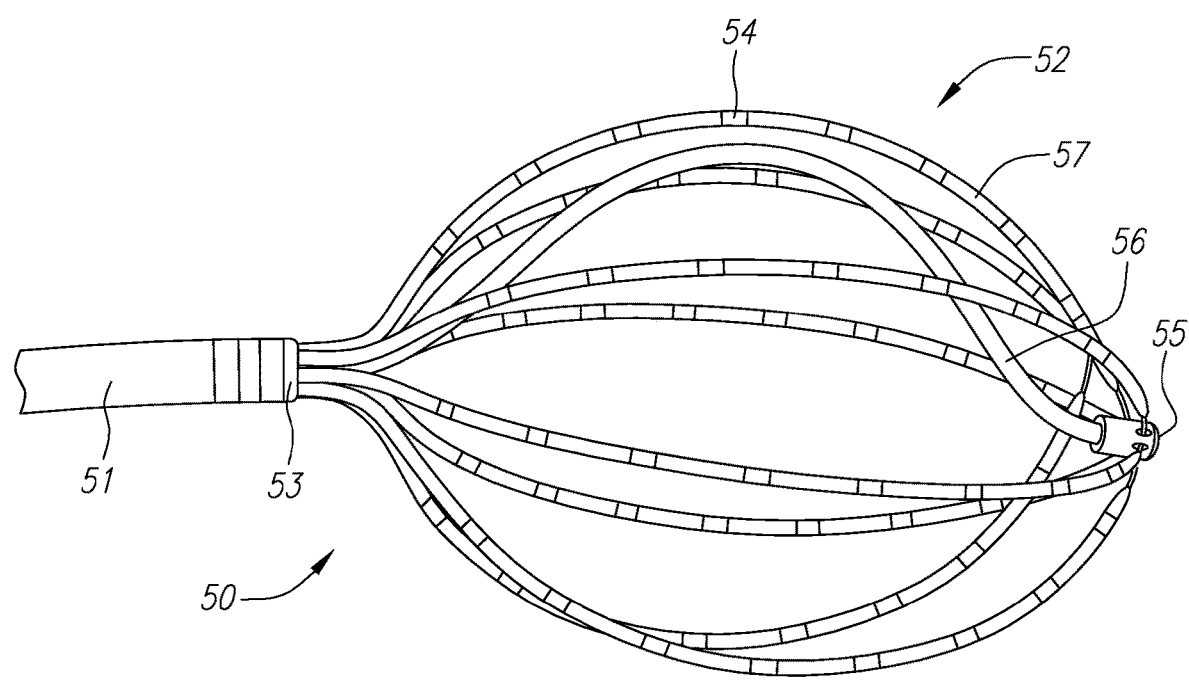
FIG. 3 is an isometric view of a basket catheter.

FIG. 3. Illustrates an embodiment of a basket catheter 50 which can be considered to be a 2D array of electrodes distributed over an ellipsoid surface. The basket catheter 50 can comprise a catheter body 51 coupled to a basket 52. The basket 52 can be coupled to the catheter body with a proximal connector 53. The basket 52 can comprise a plurality of splines 57, a distal coupler 55, and an irrigation tubing 56. Each of the plurality of splines 57 can comprise at least one electrode 54. In the illustrated embodiment, each of the plurality of splines comprises 8 electrodes. The exact number of electrodes can be varied based on the desired characteristics. The basket catheter shown in FIG. 3 is further described in U.S. provisional application No. 61/936, 677, filed 6 Feb. 2014, which is hereby incorporated by reference as though fully set forth herein Current techniques to estimate conduction velocity and the direction of activation generally rely on robust determination of activation times over precise distances. The techniques to assign times to signal locations can result in predictions that are not accurate under certain conditions. The method below utilizes the fundamental concept of wave propagation and does not rely on LAT (local activation time) detection algorithms. This approach is more robust and consistent. Certain extensions are also described that specialize and enhance the application to 2- and 3-dimensional arrangements of electrodes on cardiac surfaces. With each depolarization, the local electric field vector, E, sweeps out a loop like trajectory governed by anatomic and physiologic factors adjacent to these arrangements of electrodes. Two dimensional electrode arrangements allow the resolution of $E_t$, the "tangent bipole vector", which is a useful orientation independent signal to which wave propagation principles can be applied and can be used to introduce a scalar version of $E_t$ along the unit activation direction â, and call it $E_a$.

Three dimensional electrode arrangements allow the resolution of a component of E along the surface normal direction denoted n̂ called $E_n$. Finally, both 2- and 3-dimensional electrode arrangements allow determination of the E field along the direction ŵ=n̂×â called $E_w$ which for traveling waves is a very small signal.

Figure 4:
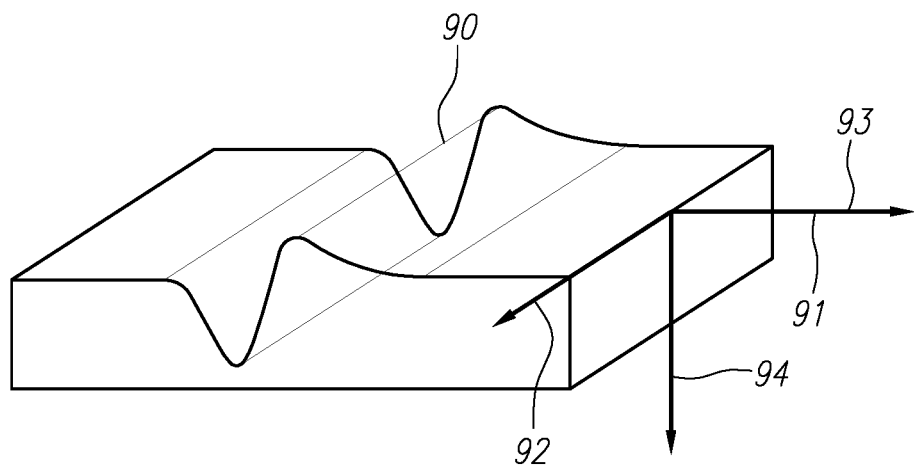
FIG. 4 is an illustration showing the activation, wavefront, surface normal, and conduction velocity directions for a traveling wave.

FIG. 4 illustrates the unit activation vector 91, wavefront vector 92, surface normal vector 94, wavefront crest 90, and conduction velocity direction 93. A single depolarization wavefront 90 is depicted based on a unipolar traveling wave voltage signal, φ(x,y,z,t). Propagation of the depolarization wavefront 90 occurs from left to right in the view. The depolarization wavefront 90 does not have to conform to a specific shape for the discussion within this disclosure to be valid, but a benefit can be found from physiologic unipolar morphology.

The orientation independent omnipole signals $E_n$ and $E_a$ possess characteristic shapes and amplitudes in normal myocardium. This can be further seen in FIGS. 6A-6C.

These permit more robust determinations of EP characteristics such as electrogram amplitude, activation timing, and conduction velocity by traditional means.

The next section explains the derivation of the omnipole or "equivalent bipole" signal $E_a$ using a high density catheter such as one of the catheters 10, 30, 50 shown in FIGS. 2-3. The paddle catheter, basket catheter, or other high density catheter is presumably maneuvered such that some or all adjacent electrodes lie flat on the surface/substrate. For convenience the following will use language indicating all catheter electrodes lie on the surface (i.e. the catheter lies on the surface) but the language refers to those electrodes that do lie on the surface or are sufficiently close to be indistinguishable from those that do.

The E-field (E) in the plane of the surface can be calculated using electrode locations X and the potentials measured at the electrodes φ using the following equations (where dφ and dX have been derived from X, φ, and subtraction matrix F, as described in international application no. PCT/US2014/037,160 filed 7 May 2014 and published in English on 13 Nov. 2014 under international publication no. WO 2014/182822 (the '822 application) and U.S. provisional application No. 61/855,058, filed 7 May 2013 (the '058 application). The '822 application and the '058 applications are both hereby incorporated by reference in their entirety as though fully set forth herein. The equations have the same form for both 2D and 3D situations:

$$d\varphi = -(dX)^T \cdot E \quad (1)$$

$$E = -((dX)^{-T})^+ d\varphi \quad (2)$$

where
φ—vector of unipolar potentials,
dφ—vector of bipolar potentials with respect to a common reference electrode,
X—matrix of mapping system coordinates for the electrodes,
dX—matrix of bipolar displacements with respect to the reference electrode location, and
$A^+$ is the Moore-Penrose generalized inverse of matrix A.

Figure 5:
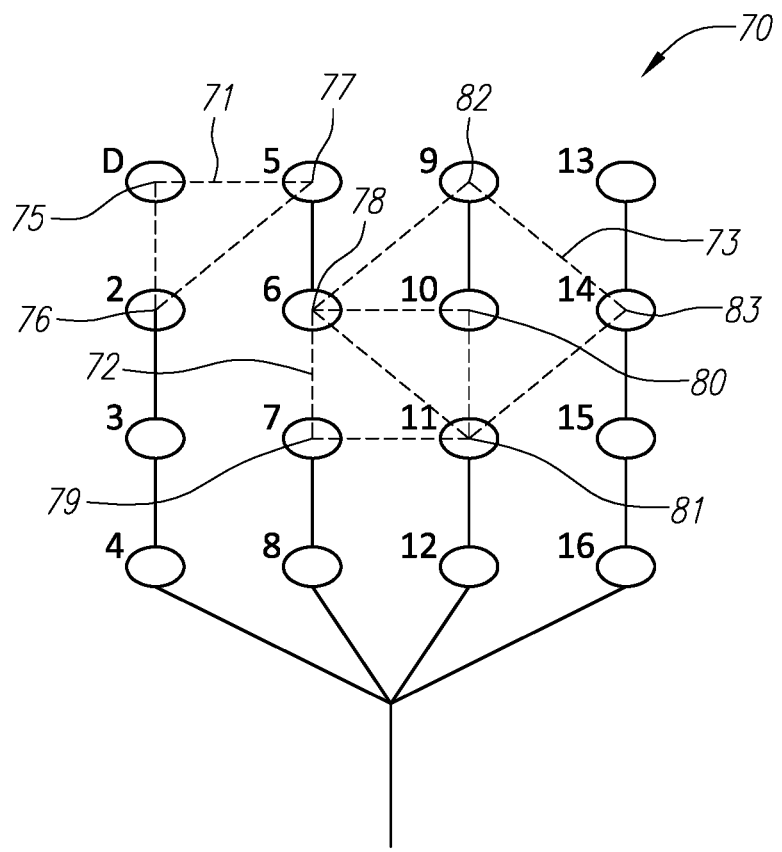
FIG. 5 is a schematic illustrating electrode location and clique geometry.

FIG. 5. Illustrates one embodiment of a paddle catheter 70 showing 16 electrodes and some of the sets of electrodes that can be used to determine $E_t$. In the illustrated embodiment, the paddle catheter 70 can comprise four splines with each spline comprising four electrodes. Any 2D electrode set with at least three adjacent electrodes forms a clique and can be used for the calculations. A three electrode clique 71, a four electrode clique 72, and a five electrode clique 73 is illustrated on the paddle catheter 70 in FIG. 5. The three electrode clique 71 can comprise electrodes D 75, two 76, and five 77. The four electrode clique 72 can comprise electrodes six 78, seven 79, ten 80, and eleven 81. The five electrode clique 73 can comprise electrodes six 78, nine 82, ten 80, eleven 81, and fourteen 83. As can be seen by the above illustration, the same electrode on the catheter can be used for multiple cliques The local E-field at a position on the surface can be calculated from sets of sufficient nearby electrodes (also referred to as a clique) on the catheter as illustrated in FIG. 5. As indicated generally by dashed lines in FIG. 5, for example, a 2-dimensional clique may comprise a set of three or more electrodes (e.g., electrodes D, 5, 2) located alone a plane of the catheter. When only a unipole or bipole is present the clique can be referred to as a degenerate clique. A degenerate clique is unable to be used to determine orientation independent assessments of directional quantities. A unipole degenerate clique, while orientation independent, has no real directional information. When, for example, more than 3 electrodes are used in a clique, the bipolar signals over-determine the 2D field. In such an instance, where the clique has more electrodes than strictly necessary for its 2D or 3D role, the clique is overdetermined and admits "subcliques." Subcliques are themselves cliques which may or may not be minimal depending on how overdetermined the original clique was to start with and what subclique is being reviewed. Cliques that are not degenerate allow omnipoles and subcliques allow a unique direct demonstration of orientation independent sensing (OIS) superiority over traditional bipoles. OIS can be uniformly better than bipoles in determining many EP characteristics, including amplitude, timing, conduction velocity direction and magnitude. Although FIG. 5 only illustrates cliques comprising three (electrodes D, 5, 2) 71, four (electrodes 6, 10, 11, 7) 72, and 5 (electrodes 9, 14, 11, 6, 10) 73 neighboring electrodes, the method can be extended to other cliques with more electrodes on the catheter. Since the catheter is assumed to lie flat on the substrate, the full 3D vector E at any clique is also expected to have components in the 2D tangent plane of the endocardial or epicardial surface. As a result, the term $E_t$ is used to describe the component of the E-field in the tangent plane.

One method of determining the local E field is to choose one electrode from the clique as a reference electrode and determine n−1 bipolar potentials (dφ) and displacements (dX) with respect to the reference electrode. Another method of determining the local E field is to determine all possible distinct bipoles (n*(n−1)/2) from the clique's n electrodes to compute dφ and dX. Determining all possible distinct bipoles can lead to a more robust determination of the E-field as it reduces "2nd order" orientation effects that result from the electrode distribution with respect to wavefront.

Let â and ŵ be unit vectors in the tangent plane along the activation and wavefront directions as illustrated in FIG. 4. For an ideal, homogenous wavefront, $E_t$ is expected to be either parallel or anti-parallel to the activation direction (â) with very little component along the wavefront direction (ŵ). The scalar $E_a$ (also the equivalent bipole or omnipole activation signal) can be defined using the dot product as $$E_a = E \cdot â = E_t â \quad (3)$$

$E_a$ is the equivalent bipolar EGM that would be measured if one were to place a pair of bipoles separated by 1 mm along the activation direction. By definition, $E_a$ is catheter and clique orientation independent and hence its morphology and amplitude should purely be a function of the local substrate. By virtue of it being a bipolar signal, it is also expected that it would be largely free of far-field artifacts and possess a stable isoelectric baseline.

Figure 6B:
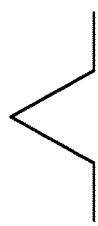
FIGS. 6A-6C are graphs depicting exemplary equivalent bipole signal shapes and amplitudes.
Figure 6C:
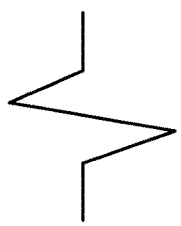
Figure 6A:
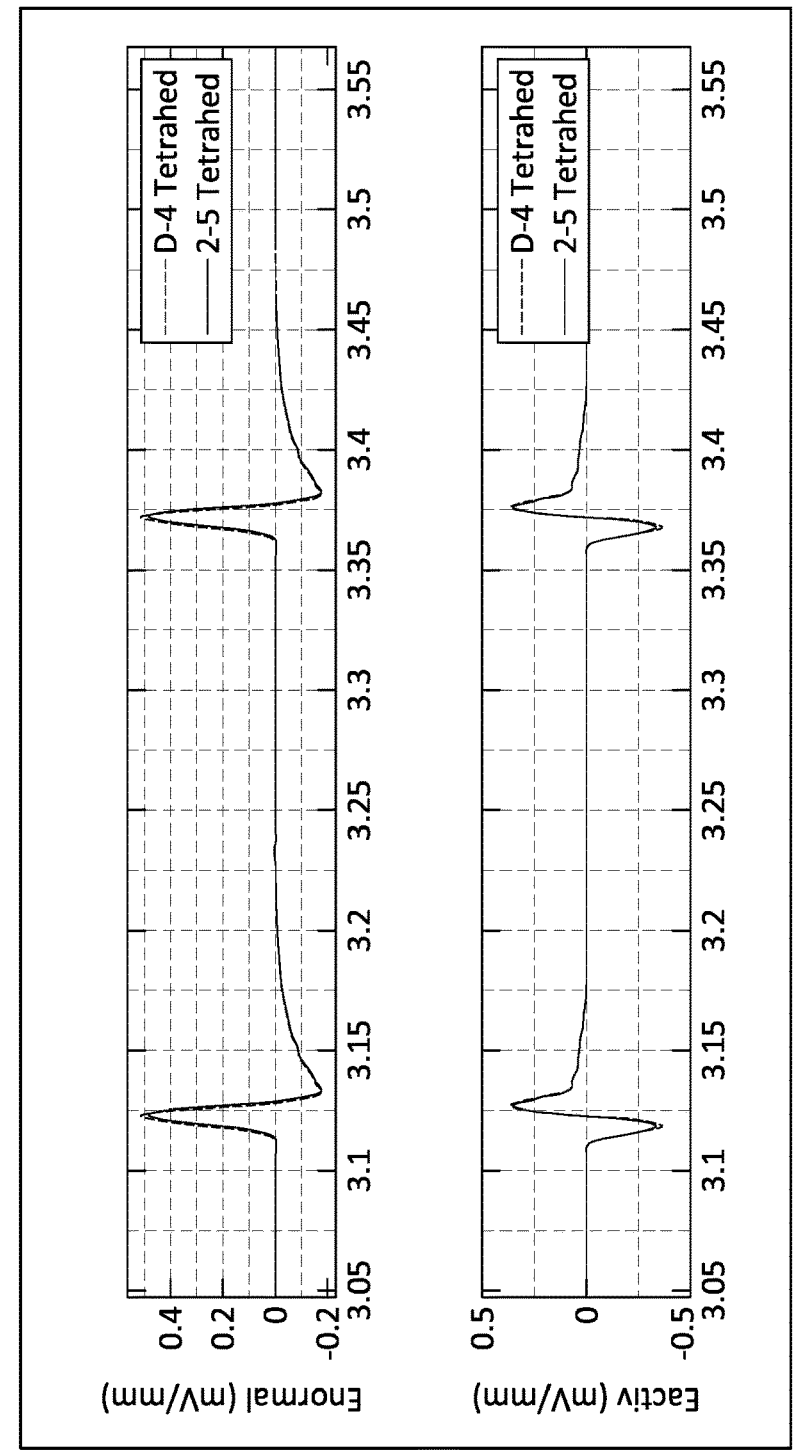

FIGS. 6A-6C illustrate characteristic OIS omnipole signal shapes and amplitudes that permit more robust assessments of substrate including scar and activation timing maps. The two signals thus resolved ($E_n$ and $E_a$) are significantly independent of each other, opening the possibility of learning more from local EGM signals. FIG. 6B illustrates an exemplary $E_n$ signal and FIG. 6C illustrates an exemplary $E_a$ signal. The algorithm to determine $\hat{c}$ from $E_t$ will be explained below.

The conduction velocity can be derived from the E-field using traveling wave concepts. The potential is recognized to be a function of space and time. Propagation of a traveling wave with velocity $v=(v_x, v_y, v_z)$ implies that the wave at time to matches exactly the wave at a time $t_0+t$ at coordinates $x+v_x t$, $y+v_y t$, and $z+v_z t$. As a result $$\varphi(x_0, y_0, z_0, t_0) = \varphi(x_0 v_x t, y_0 + v_y t, z_0 + v_z t, t_0 + t) \quad (4)$$

for all initial times and locations $t_0$, $x_0$, $y_0$, $z_0$ for all times t. Taking the total derivative of both sides of the above equation with respect to time leads to $$0 = \frac{\partial \varphi}{\partial x} v_x + \frac{\partial \varphi}{\partial y} v_y + \frac{\partial \varphi}{\partial z} v_z + \frac{\partial \varphi}{\partial t}$$

which we note is equivalent to $$0 = \nabla \varphi \cdot v + \dot{\varphi} \quad (5)$$

where v is a vector representing cardiac conduction velocity. Recognizing that $E=-\nabla\varphi$ and that only the component of E-field in the tangent plane contributes to the inner product, we get $$E_t \cdot v = \dot{\varphi} \quad (6)$$

$$E_a(\hat{a} \cdot v) = \quad (7)$$

The conduction velocity vector v can then expressed as $$v = \frac{\dot{\varphi}}{E_a} \hat{a} \quad (8)$$

Conduction velocity, a presumed constant during depolarization, is recognized to be the ratio of the time derivative to the spatial derivative in the tangent plane of the potential. It is then expected that under ideal conditions, the morphology of $E_a$ would be similar to that of $\varphi$ with the only difference being a scale factor which would be the velocity magnitude. The activation direction ($\hat{a}$) is determined to be the direction in the tangent plane that results in the maximum correlation between $\dot{\varphi}$ and $E_a$. Although the expression above holds in principle at every time point, when signal levels are sufficiently small or isoelectric, the ratio of $\dot{\varphi}$ to $E_a$ cannot be meaningfully determined.

The analysis can be expected to be more robust when the electrodes that form a clique are in good contact with the surface. This can be checked and enforced a priori using some or all of the criteria below. The criteria to check whether a clique is in good contact with the surface can be applied together or separately as determined by the user or process. Automatic application of the first six criteria can form an important component of the disclosure as getting uniform contact of all electrodes is generally difficult for any catheter, particularly so for small basket catheters.

The first criteria looks at the angular deviation between a 3D mapping systems determined surface normal near the clique and the normal to the plane that best fits the electrodes on the clique and determines whether they are below a threshold. The second criteria looks at the angular deviation between the normal corresponding to the clique of interest and the normal corresponding to the neighboring cliques and determines whether they are below a threshold. The third criteria looks at the distance between the electrode locations that form the clique and the surface and determines whether they are below a threshold. In one embodiment, the second criteria further includes ensuring that the local curvature is not above a threshold. The fourth criteria looks at the amplitudes of the unipolar signals obtained from the electrodes on the clique and determines whether they are within a typical range. The fifth criteria looks at the morphologies of the unipolar signals obtained from the electrodes on the clique and determines whether they are typical (e.g. modest upstroke followed by a dominant down deflection and fairly prompt return). The sixth criteria looks at the amplitudes, shapes, and morphologies of Et, and Ea obtained from the clique and determines whether they are typical. The seventh criteria looks at the visual cues for good contact such as fluoro, ICE, etc. as well as tactile sensations and maneuvering history on the part of a catheter operator. While seven criteria are listed herein to check whether a clique is in good contact with the surface, not all seven of the criteria listed have to be used to make that determination. Further, other criteria can also be used to determine whether a clique has made good contact with a surface.

Figure 7:
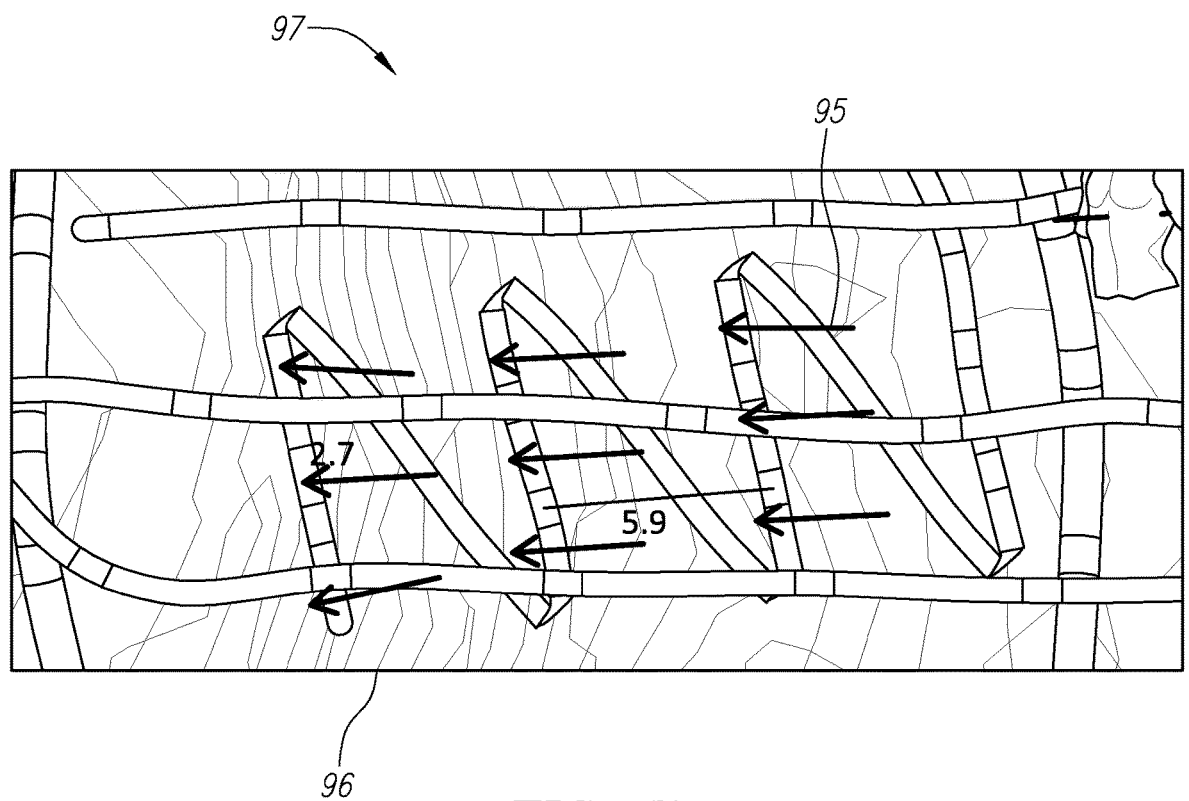
FIG. 7 is a combined map showing activation propagation vectors and isochrones.

Conduction velocity once derived can be displayed with a 3D mapping system on the chamber geometry using, for example, arrows, with the direction of the arrow indicating the activation direction and the color, length, or width of the arrow showing the magnitude. In another embodiment an interpolated color map can also be used to display conduction velocity magnitude with or without arrows of uniform length showing the direction. FIG. 7, as discussed below, illustrates another embodiment where conduction velocity vector maps can also be coupled with LAT maps. Generally, the display is updated immediately following each local depolarization and persisting or gradually fading out until the next local depolarization. Finally, some or all isochrones may be displayed as curved lines on the cardiac surface, for instance at specific intervals since the start of depolarization such as 0, 20, 40, and 60 ms. This reduces visual clutter and allows a more interpretable superposition of conduction velocity arrows.

FIG. 7. Illustrates a combined map showing a catheter 98, a plurality of electrodes 99, a plurality of activation propagation vectors 95 and isochrones. The activation propagation vectors 95 can be of constant length and color coded to indicate the magnitude of velocity. Alternatively, the length or the size of the vectors can also be used to indicate the magnitude of velocity. The vectors 95 can also be superimposed on color maps 97 of conduction velocity magnitudes, activation time, amplitude, or any of a variety of other indices of cardiac function. The gradient lines 96 can be used to shown conduction velocity magnitudes with various colors representing different velocities. Maps showing conduction velocities with color gradients are well known in the art and used in many different systems.

As can be readily appreciated from equations 1 and 2 listed above, it is important to have reasonably accurate electrode displacements (dX) and electrode positions (X) to judge contact and the local surface tangent plane so as to portray the signals and resulting EP characteristics including conduction velocity accurately. It has been suggested that impedance based mapping system locations are more robustly determined from tip or circumferential ring electrodes than from small surface area electrodes on portions of a catheter shaft. Nevertheless, the issue can remain significant in catheter designs with small ring electrodes on flexible splines. Small electrodes, owing to their high electrode-electrolyte impedance can be difficult to locate accurately—they are more susceptible to artifact and can be biased toward the system reference "belly patch" electrode. Compensation algorithms can be used to correct for the positions, however, they rely on a priori knowledge of the construction and inter-electrode distances. Flexible splines can deform, bunch up, or become separated (splayed) in vivo under certain conditions resulting in important deviations from their nominal design. When that happens, the compensation algorithms referred to above may not be able to effectively correct electrode location errors. Means to prevent the deformations, bunching, and separation of catheter splines and electrodes from becoming severe enough to significantly disturb assessments of EP characteristics are also disclosed above in relation to FIG. 2C.

Figure 8:
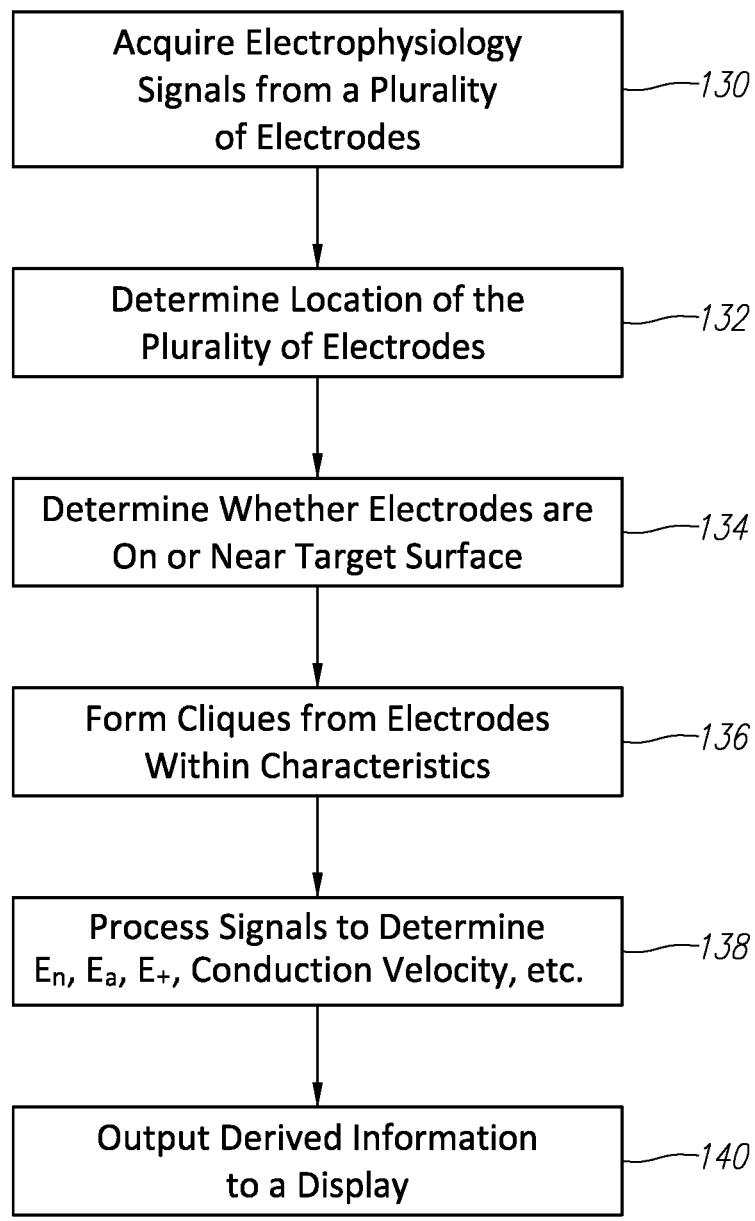
FIG. 8 illustrates a flowchart showing a step-by-step approach to acquire, determine, and output orientation independent information.

FIG. 8 illustrates a flowchart showing a step-by-step approach to acquire, determine, and output orientation independent information. The method illustrated in the flowchart can comprise the following steps:

At step 130 acquire electrophysiology signals from a plurality of electrodes.

At step 132 determine the location of the plurality of electrodes in step 130.

At step 134 determine whether the plurality of electrodes are on or near the target surface.

At step 136 form cliques from the electrodes that fit within defined characteristics for inclusion in cliques.

At step 138 process the electrophysiology signals to determine $E_n$, $E_a$, $E_t$, conduction velocity, and other orientation independent characteristics such as amplitude or timing.

At step 140 output the derived information to a display.

Helical basket catheters have been proposed as a means to achieve more uniform coverage of electrodes over the extent of a basket. This can be a desirable characteristic for this disclosure on its own, but also for the increased stiffness (and thus resistance to displacement) that results. Increased stiffness can allow for reliance on the spacing as determined by design and manufacturing rather than the mapping system location for each electrode.

Figure 9:
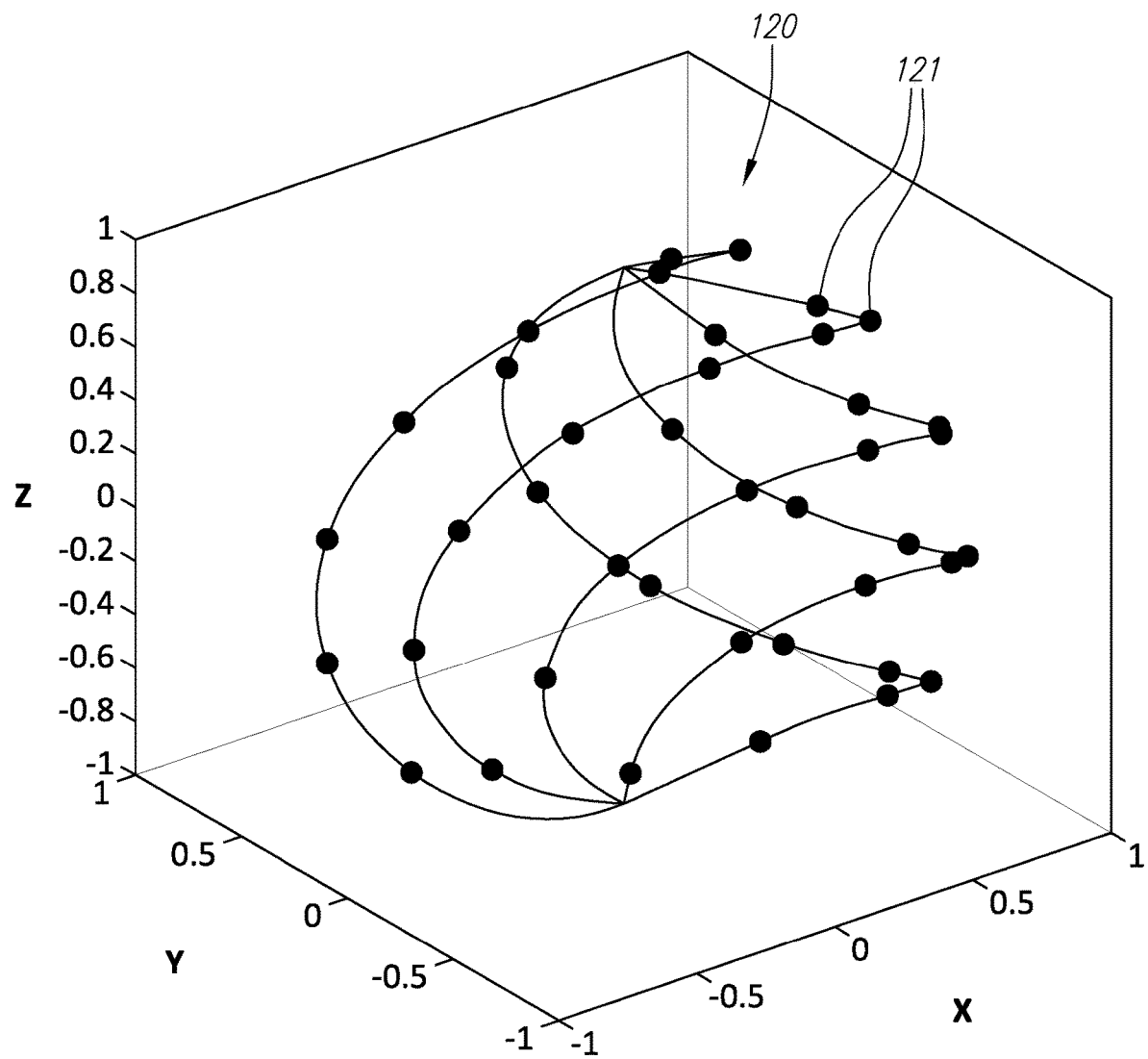
FIG. 9 is a diagrammatic view of helical basket catheter design with non-uniform electrode spacing along splines but uniform spacing over the ellipsoidal basket surface.

FIG. 9 illustrates a helical catheter design of a catheter 120 with non-uniform electrode spacing along splines but achieves a nearly uniform electrode dispersal over the outer surface of the basket. Each point 121 in the figure represents an electrode. The catheter illustrated in FIG. 9 is further described in U.S. application Ser. No. 13/790,110, filed 8 Mar. 2014, which is hereby incorporated by reference as though fully set forth herein.

The local nature of determinations made by beam buckling theory suggests compliance goes as the length dimension squared so twice as small translates to 4 times stiffer. With small size, then, come the benefits of: (a) interelectrode spacing more consistent under varying use conditions, (b) more dense sampling and thus better spatial resolution, and (c) the capacity to be maneuvered into full contact positions and orientations.

As discussed earlier, conventional mapping techniques suffer from bipole orientation induced amplitude and morphology uncertainty which also adversely affects activation timing. Challenging arrhythmias in clinical EP today may involve features such as channels with low amplitudes and slow conduction that are only of the order of 5 mm in width. Detailed maps are often not required over an entire cardiac chamber but confined to certain locations where pathology often appears or other diagnostic tests such as surface ECGs, ultrasound, MRI, or even basic EP catheter signals indicate. What is important is that the information reliably reflect the state of the myocardium locally and that it do so with adequate resolution.

The algorithm discussed in the invention can be used to derive local E-fields (including E and $E_t$), and equivalent bipolar signals ($E_n$ and $E_a$) with orientation independent amplitudes and reliable morphology/timing, and instantaneous conduction velocity vectors. We postulate such characterization will permit improved maps of substrate amplitude (using $E_n$, $E_a$, or measures of E field loop size), activation times (LAT), conduction velocity (magnitude and direction), as well as a novel index of inhomogeneous conduction derived from $E_w$ or the eccentricity of $E_t$. Bipolar-like omnipole signals of consistent morphology may be understood from the fundamentals of cell depolarization and unipolar EGM signals when in proximity to active tissue.

One or more of these characteristics can also enable clinicians to perform more reliable scar border delineation (known to contribute to VT and other arrhythmias). Also, local determinations of low amplitude and/or slow conduction velocity can help identify critical pathways such as isthmuses for arrhythmias that are amenable to ablation therapy. More reliable EGM amplitudes and morphologies can also allow better measures of EGM reduction measures, lesion characterization, or the local assessment of conduction velocity as a critical isthmus is affected or a lesion gap approached.

OIS technology can also be utilized with implanted medical devices. Implanted medical devices responsible for rhythm discrimination currently rely primarily on depolarization event timing. Timing alone however can fail to distinguish between important rhythms as the times of occurrence can be similar, and multi-chamber algorithms are not sufficiently specific. The application of OIS to an implanted device's catheter or lead can establish a baseline direction and speed (using OIS characterizations) for healthy rhythms.

Implanted devices already perform elementary mapping system functions, but with OIS technology as discussed herein, can better track the number and degree of abnormality of beats and can group them by similarity in detection criteria. For example, a non-physiologic heart rate increase typically would cause the conduction velocity to decrease, while a physiologic cause for heart rate increase, like exercise, would not result in a decrease in conduction velocity. Hence the decision to treat this tachycardia can be based not only on changes in heart rate and other traditional ICD metrics such as timing but based on noting the conduction velocity vector's direction and magnitude are consistent with a VT. Some of the detection criteria that can be used by the implanted device can include combinations of rate, number consecutive abnormal beats, frequency "x of y beats", etc.

Observations from one or more sites on implanted leads can also be used to track rate or ischemia induced functional block occurrences with greater accuracy than inferences drawn from timing changes. This in turn can enable patient or health care provider alerts to potential problems with brady or tachy arrhythmias before deciding on treatments with pacing or cardioversion shocks.

This technology is also valuable when applied at the time of RF ablation. Although OIS omnipole compatible electrode arrays today are seldom invoked as ablation electrodes, they may prove valuable in the future, particularly when combined with the resolution and consistency of the mapping capabilities described elsewhere in this disclosure. RF may be delivered through individual electrodes of such an array in the standard fashion. If, however, RF is to be delivered simultaneously through a number of adjacent electrodes so as to create a line of block or a single conjoined lesion, it is valuable to do so in a manner that maintains individual EGM signals and mapping system positions but effectively delivers RF voltage in parallel to emulate a single large electrode.

A passive circuit technique is disclosed for achieving a similar result. The passive circuit was used with an ablation catheter having a split tip that effectively deployed a 4 electrode 2D array at its tip. Capacitors served as low impedance elements to couple RF from a single generator connection at relatively high RF frequencies and serve as high impedance connections between electrodes at the lower frequencies of impedance mapping system and EGM amplifiers. Several embodiments of catheters fitting this description are further described in international application no. PCT/US2014/011,940 filed 16 Jan. 2014 and published in English on 24 Jul. 2014 under international publication no. WO 2014/113612, which is hereby incorporated by reference as though fully set forth herein. For the catheter design used herein, the circuit employed 33 nF capacitors though values between 10-100 nF would also work.

Figure 10A:
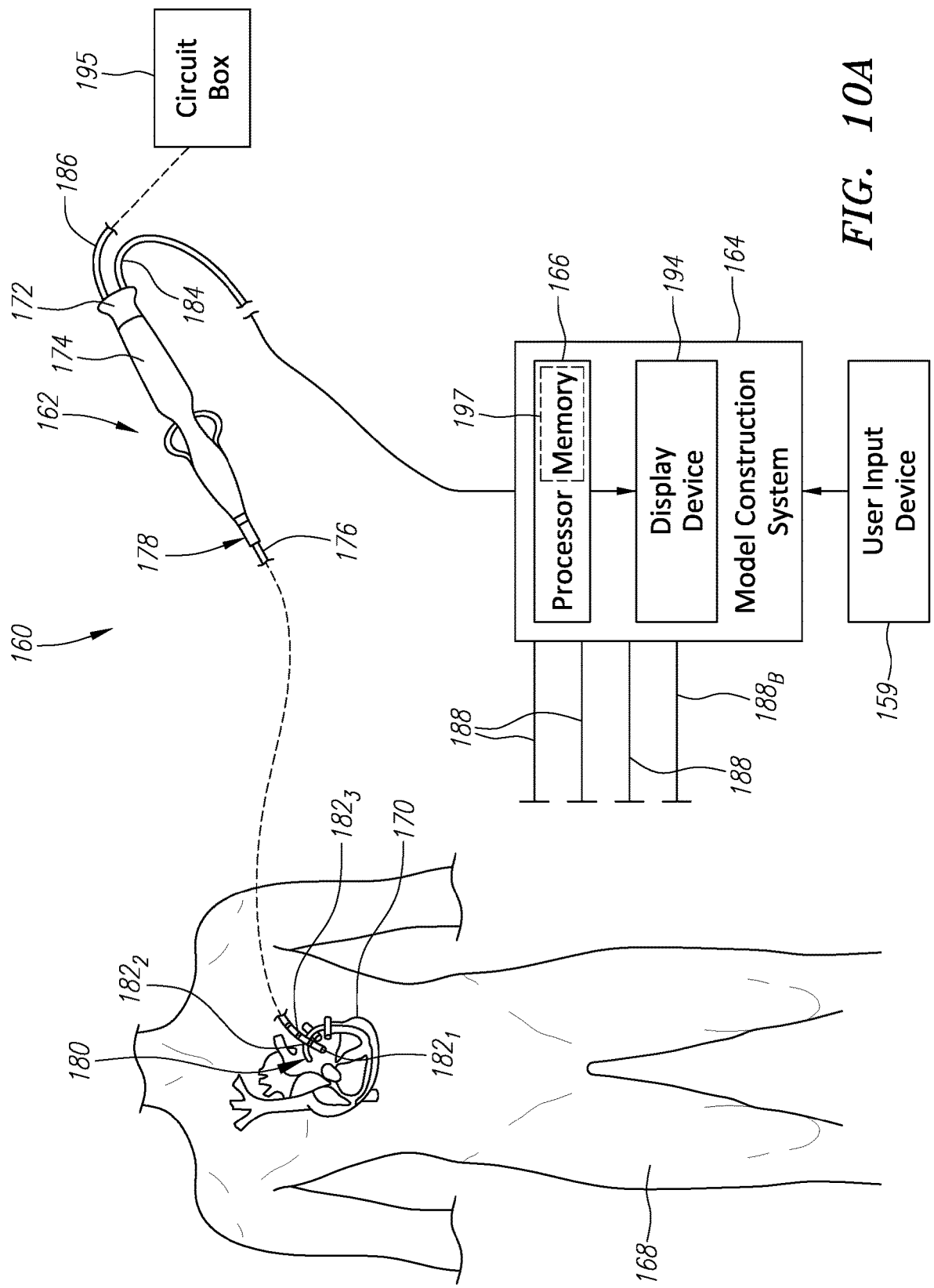
FIG. 10A is a diagrammatic view of a system for generating surface models and/or mapping electrophysiological information thereon.

FIG. 10A illustrates one embodiment of a system 160 for mapping electrophysiological information corresponding to an anatomic structure onto a multi-dimensional (e.g., three-dimensional) geometry surface model of the anatomic structure (each of the terms "electrophysiology" and "electrophysiological" will hereinafter be referred to as "EP"). The system 160 comprises, among other components, a medical device 162 and a model construction system 164. In one embodiment, the medical device 162 comprises a catheter, and the model construction system 164 comprises, in part, a processing apparatus 166. The processing apparatus 166 may take the form of an electronic control unit, for example, that is configured to obtain a geometry surface model of the cardiac structure, and to construct an EP map corresponding to the cardiac structure using data collected by, for example, the catheter 162. The catheter 162 is configured to be inserted into a patient's body 168, and more particularly, into the patient's heart 170. The catheter 162 may include a cable connector or interface 172, a handle 174, a shaft 176 having a proximal end 178 and a distal end 180 and one or more sensors 182 (e.g., 1821, 1822, 1823) mounted in or on the shaft 176 of the catheter 162. In one embodiment, the sensors 182 are disposed at or near the distal end 180 of the shaft 176. The connector 172 provides mechanical, fluid, and electrical connection(s) for cables, such as, for example, cables 184, 186 extending to the model construction system 164 and/or other components of the system 160 (e.g., a visualization, navigation, and/or mapping system (if separate and distinct from the model construction system 164), an ablation generator, irrigation source, etc.).

The sensors 182 mounted in or on the shaft 176 of the catheter 162 are electrically connected to the model construction system 164, and the processing apparatus 166 thereof, in particular. The sensors 182 may be provided for a variety of diagnostic and therapeutic purposes including, for example and without limitation, EP studies, pacing, cardiac mapping, and ablation. In an embodiment, one or more of the sensors 182 are provided to perform a location or position sensing function. Accordingly, in such an embodiment, as the catheter 162 is moved along a surface of the cardiac structure and/or about the interior thereof, the sensor(s) 182 can be used to collect location data points that correspond to the surface of, or locations within, the cardiac structure. These location data points can then be used by, for example, the model construction system 164 in the construction of a geometry surface model of the cardiac structure.

In one embodiment, the model construction system 164, and the processing apparatus 166 thereof, in particular, is configured to obtain a geometry surface model of the cardiac surface (or at least a portion thereof), and to map EP information corresponding to that cardiac structure onto the geometry surface model. The processing apparatus 166 is configured to use, at least in part, data (location data and/or EP data/information) collected by the catheter 162 in the construction of one or both of a geometry surface model and an EP map.

In an embodiment wherein the model construction system 164 is configured to construct the geometry surface model, the model construction system 164 is configured to acquire location data points collected by the sensor(s) 182 corresponding to the cardiac structure. The model construction system 164 is configured to then use those location data points in the construction of the geometry surface model of the cardiac structure. The model construction system 164 is configured to construct a geometry surface model based on some or all of the collected location data points. In addition to constructing a geometry surface model of a structure, the model construction system 164 is configured to function with the sensor(s) 182 to collect location data points that are used in the construction of the geometry surface model. In such an embodiment, the model construction system 164 may comprise an electric field-based system, such as, for example, the EnSite NavX™ system commercially available from St. Jude Medical, Inc., and generally shown with reference to U.S. Pat. No. 7,263,397 entitled "Method and Apparatus for Catheter Navigation and Location and Mapping in the Heart", the entire disclosure of which is incorporated herein by reference. In other exemplary embodiments, however, the model construction system 164 may comprise other types of systems, such as, for example and without limitation: a magnetic-field based system such as the Carto™ System available from Biosense Webster, and as generally shown with reference to one or more of U.S. Pat. No. 6,498,944 entitled "Intrabody Measurement," U.S. Pat. No. 6,788,967 entitled "Medical Diagnosis, Treatment and Imaging Systems," and U.S. Pat. No. 6,690,963 entitled "System and Method for Determining the Location and Orientation of an Invasive Medical Instrument," the entire disclosures of which are incorporated herein by reference, or the gMPS system from MediGuide Ltd., and as generally shown with reference to one or more of U.S. Pat. No. 6,233,476 entitled "Medical Positioning System," U.S. Pat. No. 7,197,354 entitled "System for Determining the Position and Orientation of a Catheter," and U.S. Pat. No. 7,386,339 entitled "Medical Imaging and Navigation System," the entire disclosures of which are incorporated herein by reference; a combination electric field-based and magnetic field-based system such as the Carto 3™ System also available from Biosense Webster.

In one embodiment, the sensor(s) 182 of the catheter 162 comprise positioning sensors. The sensor(s) 182 produce signals indicative of catheter location (position and/or orientation) information. In an embodiment wherein the model construction system 164 is an electric field-based system, the sensor(s) 182 may comprise one or more electrodes. In such an embodiment, each of the electrodes may comprise one of a number of types of electrodes, such as, for example, tip electrodes, ring electrodes, button electrodes, coil electrodes, brush electrodes, flexible polymer electrodes, and spot electrodes. Alternatively, in an embodiment wherein the model construction system 164 is a magnetic field-based system, the sensor(s) 182 may comprise one or more magnetic sensors configured to detect one or more characteristics of a low-strength magnetic field. For instance, in one exemplary embodiment, the sensor(s) 182 may comprise magnetic coils disposed on or in the shaft 176 of the catheter 162.

For purposes of clarity and illustration, the model construction system 164 will hereinafter be described as comprising an electric field-based system, such as, for example, the EnSite NavX™ system identified above. It will be appreciated that while the description below is primarily limited to an embodiment wherein the sensor(s) 182 comprise one or more electrodes, in other exemplary embodiments, the sensor(s) 182 may comprise one or more magnetic field sensors (e.g., coils). Accordingly, model construction systems that include positioning sensor(s) other than the sensors or electrodes described below remain within the spirit and scope of the present disclosure.

In one embodiment, the system 160 can further comprise a circuit box 195. The circuit box can be used as further described in FIG. 11 to implement passive isolation at EGM and impedance mapping system frequencies, and yet effectively short segments together at ablation frequencies.

Figure 10B:
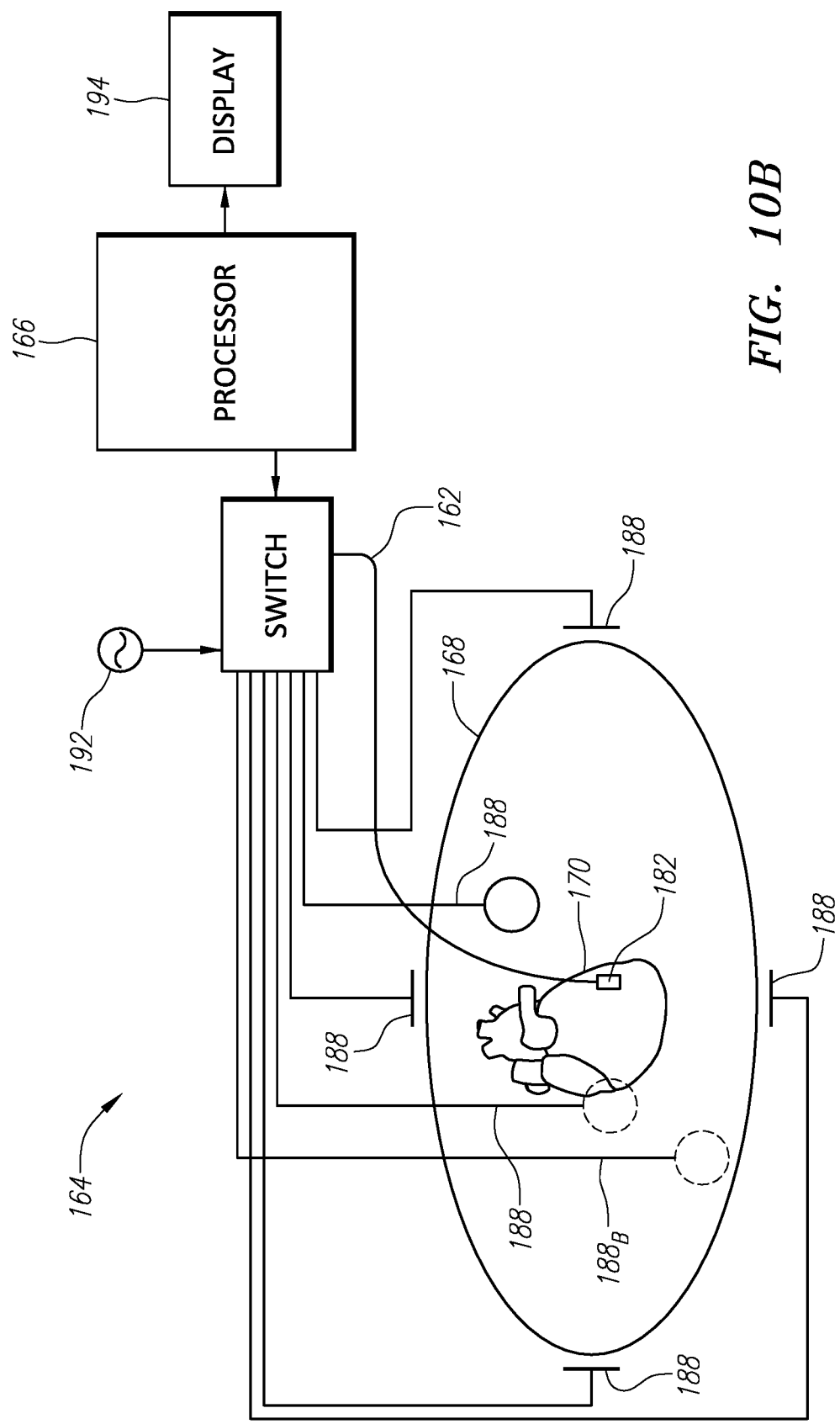
FIG. 10B is simplified diagrammatic and schematic view of a model construction system of the system illustrated in FIG. 10A.

With reference to FIG. 10B, in addition to the processing apparatus 166, the model construction system 164 may include, among other possible components, a plurality of patch electrodes 188, a multiplex switch 190, a signal generator 192, and a display device 194. In another exemplary embodiment, some or all of these components are separate and distinct from the model construction system 164 but that are electrically connected to, and configured for communication with, the model construction system 164.

The processing apparatus 166 may comprise a programmable microprocessor or microcontroller, or may comprise an application specific integrated circuit (ASIC). The processing apparatus 166 may include a central processing unit (CPU) and an input/output (I/O) interface through which the processing apparatus 166 may receive a plurality of input signals including, for example, signals generated by patch electrodes 188 and the sensor(s) 182, and generate a plurality of output signals including, for example, those used to control and/or provide data to, for example, the display device 194 and the switch 190. The processing apparatus 166 may be configured to perform various functions, such as those described in greater detail above and below, with appropriate programming instructions or code (i.e., software). Accordingly, the processing apparatus 166 is programmed with one or more computer programs encoded on a computer storage medium for performing the functionality described herein.

With the exception of the patch electrode 188B called a "belly patch," the patch electrodes 188 are provided to generate electrical signals used, for example, in determining the position and orientation of the catheter 162. In one embodiment, the patch electrodes 188 are placed orthogonally on the surface of the body 168 and are used to create axes-specific electric fields within the body 168.

In one embodiment, the sensor(s) 182 of the catheter 162 are electrically coupled to the processing apparatus 166 and are configured to serve a position sensing function. More particularly, the sensor(s) 182 are placed within electric fields created in the body 168 (e.g., within the heart) by exciting the patch electrodes 188. For purposes of clarity and illustration only, the description below will be limited to an embodiment wherein a single sensor 182 is placed within the electric fields. It will be appreciated, however, that in other exemplary embodiments that remain within the spirit and scope of the present disclosure, a plurality of sensors 182 can be placed within the electric fields and then positions and orientations of each sensor can be determined using the techniques described below.

When disposed within the electric fields, the sensor 182 experiences voltages that are dependent on the location between the patch electrodes 188 and the position of the sensor 182 relative to tissue. Voltage measurement comparisons made between the sensor 182 and the patch electrodes 188 can be used to determine the location of the sensor 182 relative to the tissue. Accordingly, as the catheter 162 is swept about or along a particular area or surface of interest, the processing apparatus 166 receives signals (location information) from the sensor 182 reflecting changes in voltage levels on the sensor 182 and from the non-energized patch electrodes 188. Using various known algorithms, the processing apparatus 166 may then determine the location (position and orientation) of the sensor 182 and record it as a location data point corresponding to a location of the sensor 182 on the surface of, or within, the cardiac structure in a memory or storage device associated with, or accessible, by the processing apparatus 166, such as the memory 197. In one embodiment, prior to recording the location as a location data point, the raw location data represented by the signals received by the processing apparatus 166 may be corrected by the processing apparatus 166 to account for respiration, cardiac activity, and other artifacts using known or hereafter developed techniques. The system described in FIGS. 10A and 10B is further described in U.S. application Ser. No. 14/533,630, filed 5 Nov. 2014, which is hereby incorporated by reference as though fully set forth herein.

Figure 11:
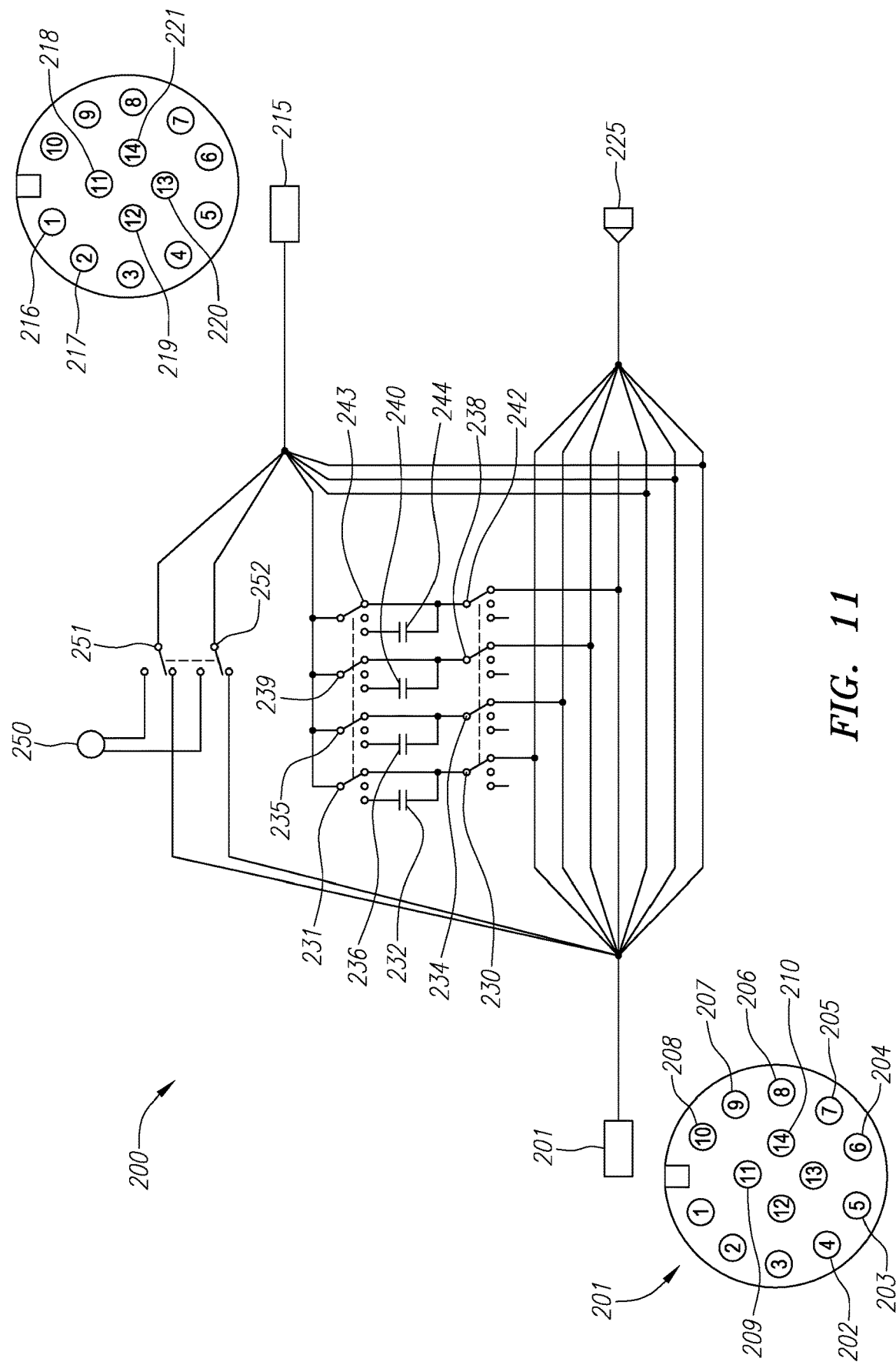
FIG. 11 is an electrical diagram of a switch box circuit configured to implement passive isolation at certain frequencies and short segments together at other frequencies.

FIG. 11 depicts a switch box circuit 200 configured interface an OIS compatible ablation catheter to an RF generator and a 3D mapping system. The circuit implements passive isolation at EGM and impedance mapping system frequencies, and yet effectively short segments together at ablation frequencies. The switch box circuit 200. The switches allow for convenient alternation between truly shorting the tip electrodes together (at all frequencies) and shorting them together for only ablation. The switch box circuit 200 introduces a practical means to treat a "split tip" ablation catheter design as a single common electrode for purposes of RF ablation and yet distinct electrodes for NavX and EGM signals. The switch box circuit 200 can be coupled to a catheter through a catheter connector 201. The catheter connector 201 can comprise a plurality of catheter pins and can be coupled to a catheter. Each of the catheter pins can be electrically connected to various sensors or electrodes on the catheter. In the illustrated embodiment a fourth catheter pin 202 can be connected to a third tip segment. A fifth catheter pin 203 can be connected to a fourth tip segment. A sixth catheter pin 204 can be connected to a first tip segment. A seventh catheter pin 205 can be connected to a proximal ring electrode on the catheter body. An eighth catheter pin 206 can be connected to a center ring electrode on the catheter body. A ninth catheter pin 207 can be connected to a distal ring electrode on the catheter body. A tenth catheter pin 208 can be connected to a second tip segment. An eleventh catheter pin 209 can be connected to a first thermocouple lead. A fourteenth catheter pin 210 can be connected to a second thermocouple lead.

The switch box circuit 200 can further be coupled to an ablation generator through an ablation generator connector 215. The ablation generator connector 215 can comprise a plurality of generator pins and can be coupled to an ablation generator. A first generator pin 216 can be coupled to a first thermocouple lead. A second generator pin 217 can be coupled to a second thermocouple lead. An eleventh generator pin 218 can be coupled to a proximal ring electrode of the catheter body. A twelfth generator pin 219 can be coupled to a center ring electrode of the catheter body. A thirteenth generator pin 220 can be coupled to a distal ring electrode of the catheter body. A fourteenth generator pin 221 can be coupled to a combined tip electrode of the catheter. The switch box circuit 200 can further be coupled to a breakout cable through a breakout cable connector 225. The breakout cable can be coupled to a breakout cable connector 225 that can comprise a plurality of breakout pins. A first breakout pin can be coupled to a first tip segment. A second breakout pin can be couple to a second tip segment. A third breakout pin can be coupled to a third tip segment. A fourth breakout pin can be coupled to a fourth tip segment. A fifth breakout pin can be coupled to a distal ring electrode of the catheter body. A sixth breakout pin can be coupled to a center ring electrode of the catheter body. A seventh breakout pin can be coupled to a proximal ring electrode of the catheter body.

The switch circuit box 200 can further comprise a plurality of switches. Each of a plurality of tip segment electrodes can be electrically coupled to an RF ablation generator by two switches and a capacitor. The illustrated embodiment of the switch circuit box 200 can be configured to couple a catheter with four segmented tip electrodes and at least one thermocouple to an ablation generator and a mapping system. In the illustrated embodiment, the switch box circuit 200 can be coupled to a catheter comprising four segmented tip electrodes. The first tip segment can be electrically coupled to a first switch 230, a second switch 231, and a first capacitor 232. The second tip segment can be electrically coupled to a third switch 234, a fourth switch 235, and a second capacitor 236. The third tip segment can be electrically coupled to a fifth switch 238, a sixth switch 239, and a third capacitor 240. The fourth tip segment can be electrically coupled to a seventh switch 242, an eighth switch 243, and a fourth capacitor 244.

The first, third, fifth, and seventh switches can be referred to as a first set of switches in the switch circuit box 200. The second, fourth, sixth, and eighth switches can be referred to as a second set of switches in the switch circuit box 200. The first set of switches can be configured to disconnect the plurality of tip segment electrodes from an ablation generator. In the illustrated embodiment, the plurality of tip segment electrodes can comprise four tip segment electrodes, each of which is connected to a switch in the first set of switches. The second set of switches can be configured to have the plurality of tip segment electrodes appear to the ablation generator as if they are a direct short. The second set of switches can further be configured to allow the plurality of tip segment electrodes to appear as a single capacitively coupled blend electrode. As a result of the first set of switches and the second set of switches the switch circuit box 200 can allow for an ablation generator to see the plurality of tip segment electrodes as one tip electrode and emit energy accordingly, while at the same time allow a mapping system to see the plurality of tip segment electrodes as independent electrodes. In another embodiment, the RF generator sees no tip electrode when the first set of switches is in a first state, and a blend of the 4 tip segments as decided by the capacitors 232, 236, 240, 244 and the first set of switches in a second state. When the second set of switches are in a first state the 4 split tip electrodes are directly shorted together. When the second set of switches are in a second state, the 4 split tip electrodes are effectively combined for RF but distinct for mapping systems and electrograms. The visualization of the electrode can be seen in FIGS. 12A and 12B.

The switch circuit box 200 can further comprise a distinct thermocouple 250. The circuit box's distinct thermocouple 250 can be electrically coupled to a first thermocouple switch 251 and a second thermocouple switch 252. When the first thermocouple switch 251 and the second thermocouple switch 525 are in the up position, a signal from the circuit box's distinct thermocouple 250 can be transmitted to the ablation generator. When the first thermocouple switch 251 and the second thermocouple switch 252 are in the down position, a signal from the catheter thermocouple can be transmitted to the ablation generator.

FIGS. 12A and 12B illustrate the passive circuit described in FIG. 11 in use with a mapping system as described herein. The effectiveness of the passive circuit approach described in this disclosure can be seen for an ablation catheter with four tip electrodes. The common capacitively coupled connection that is intended for only ablation, when shown as a rendered ablation catheter 290 in an impedance mapping system shows up as a tip electrode at the center of a 2D planar array of a rendered split tip catheter 292. While two separate catheters, the rendered ablation catheter 290 and the rendered split tip catheter 292, are both displayed in the mapping system, these two catheters comprise a single catheter and the switch box circuit can allow for them to be displayed as two. As seen in FIG. 12B, the rendered ablation catheter 290 is disposed within the 2D planar array of the rendered split tip catheter 292. The impedance mapping system shows the capacitively coupled connection and split tip electrode as separate catheters sharing the same general space in locations proximal of the split tip. The three proximal ring electrodes are handled conventionally and thus co-locate for the rendered ablation catheter 290 and the split tip catheter 292. The figure further comprises a circular mapping catheter and a reference catheter. FIGS. 12A and 12B show that there is no change in appearance in the impedance mapping system or electrogram signals before and during RF ablation when using the four capacitively coupled split tip electrodes as a single RF tip electrode. FIG. 12A depicts the impedance mapping system at 1 second before RF ablation, and FIG. 12B depicts the impedance mapping system at 2 seconds after RF ablation.

Methods to identify focal sources and rotors using the signals derived in the previous sections are next disclosed. Two approaches to identify this information will be presented. The first approach is most general and relies on triangular cliques. The second approach is specific to the rectangular cliques of a paddle catheter as previously discussed. The propagation of a wavefront from a focal source is typically slow near the source and speeds up as it propagates through the rest of the myocardium. In one embodiment, focal source candidates are identified by locating regions with low conduction velocity using conduction velocity maps. In another embodiment, the region with minimum conduction velocity can be identified to be the location of focal sources. This can be done without mapping the entire chamber, by choosing successive locations in the direction opposite to "outbound" conduction velocity. A chain of velocity vectors traces a path to the focal source in a step by step process, avoiding a need to map most of or the entire chamber and thus saving time. Alternatively, gradients of the velocity magnitudes (v=|v|) calculated from multiple cliques in a single acquisition can also be used to direct the user towards the region of minimum conduction velocity.

Convex (outward) propagation vectors are associated with lower conduction velocities. This is a result of each depolarized cell having to activate by gap junctions more cells ahead of it in a manner dependent on the curvature. Pacing near threshold can, depending on both the size and amplitude of the pacing stimulus as well as local preferential pathways or anisotropic (directionally dependent) conduction result in a symmetric or asymmetric pattern which the arrays of this invention disclosure are well suited to identify.

Figure 13:
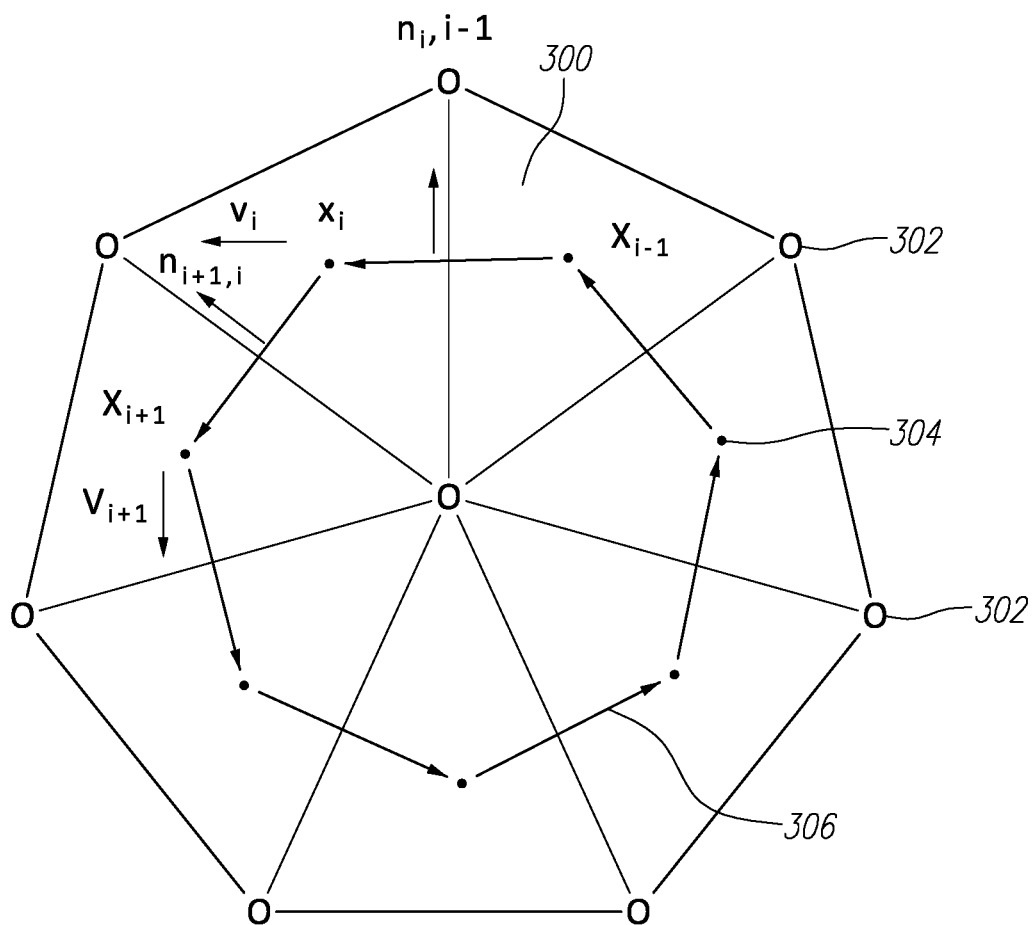
FIG. 13 is a diagram of a set of cliques and the path integrals that can be determined from the cliques.

Regions with focal activity and rotors can also be identified by approximating surface and closed path integrals of velocities derived at a set of neighboring cliques. Electrodes on a catheter can form 3 or more electrode cliques. About an interior common electrode, a closed path can be considered to pass through the centroid of each clique. This is illustrated in FIG. 13. The cliques enclosed by this path form a surface. Conduction velocity distributions on such surfaces and closed paths lend themselves to approximations of divergence and curl vector operations through Stokes Theorem and the Divergence or Gauss Theorem.

FIG. 13 shows the surface points corresponding to electrode locations and a plurality of cliques 300 formed using an electrode triplet. The points 302 represent the surface electrode locations and the dots 304 correspond to the centroid of the cliques 300. The path integrals 306 are evaluated along the lines that connect the centroids 304 of the cliques 300. Adjacent electrode groups, shown here as triangle cliques, provide local conduction velocities. This process enables a mapping system to compute indices of strong uniform propagation, rotation (rotors), and source/sink and can permit automated classification of field of view.

An angle dependent assessment of conduction velocity can be conceptually defined in a neighborhood about a point to be $$p(\theta) = \iint_A v(A) \cdot t(\theta) dA / \iint_A dA \quad (9)$$

where A is the small region over which the surface integral is calculated (typically would span the area covered by a set of neighboring cliques). $t(\theta)$ is a unit vector oriented at an angle $\theta$ with respect to an arbitrary axis. Normalized or weighted by area, the maximum of $p(\theta)$, P, is the mean velocity directed at angle $\theta$, and thus forms the mean velocity vector of area A. In practice, an integral over area A may be discretely approximated by the sum over the cliques that compose A and the velocity at each point in A, v(A), approximated as piecewise constant in each clique. To summarize, uniform propagation is characterized by a highly eccentric $p(\theta)$ whose maximal value P is in the physiologic range of conduction velocities, roughly 0.3<P<1.4 mm/ms.

Figure 14A:
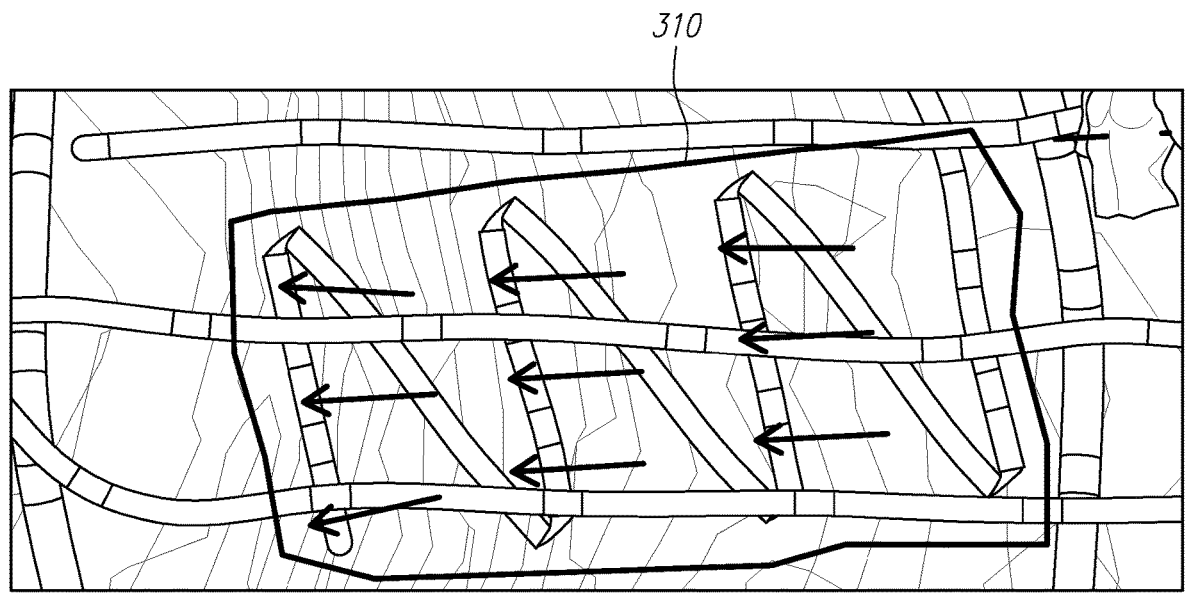
FIGS. 14A and 14B are diagrams of a determination of a mean conduction velocity vector field over an area.
Figure 14B:
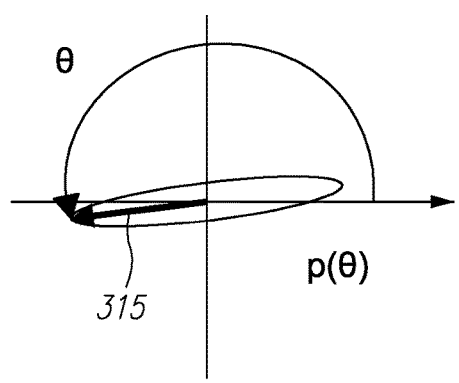

FIGS. 14A and 14B illustrate the determination of an approximately uniform conduction velocity vector field over area A 310 and the determination of mean velocity vector 315. As unit direction vector $\hat{u}(\theta)$ is rotated through 360 degrees, $p(\theta)$ traces out an ellipse with its maximum direction 315 aligned along a major axis.

$$P = \max_{\theta} \left\{ p(\theta) = \sum_i v_i \cdot \hat{u}(\theta) \cdot A_i \bigg/ \sum_i A_i \right\}$$

Once uniform conduction has been judged unlikely, the velocity vector field may be processed for evidence of rotational or focal source activity. Using Stoke's theorem and Gauss' theorem, the curl and divergence of the velocity field can be calculated using path integrals as follows $$\iint_A (\nabla \times v) \cdot dA = \oint_S v \cdot ds \quad \text{curl} \quad (10)$$

$$\iint_A (\nabla \cdot v) dA = \oint_S v \cdot \hat{n} ds \quad \text{div} \quad (11)$$

A path integral around closed path S which contains area A 310 may be discretely approximated as a sum over the line segments that join clique centroids (e.g. the lines 306 of FIG. 13) or the exterior path consisting of all outer segments of area A 310. As we did for uniform propagation, it is convenient to normalize the results into a signed mean rotational velocity vector magnitude and signed mean outward pointing velocity vector magnitude so as to not depend on clique or area A's size and better discern true rotational or outer/inner propagation from random results in scar tissue.

Let $x_i$ denote the coordinates of the $i^{th}$ clique's centroid for cliques that form the outer boundary of area A. Also let $v_i$ be the velocity vector associated with that clique. Then define the "average path vector" between centroid points i−1 and i+1 to be $$\delta_i = \frac{(x_{i+1} - x_i) + (x_i - x_{i-1})}{2} = \frac{(x_{i+1} - x_{i-1})}{2}$$

where the indices wrap appropriately around the closed path for area A. Then the path length weighted curl of the velocity vector field may be defined to be $$C := \Sigma_i \delta_i \cdot v_i / \Sigma_i |\delta_i|$$

The path length weighted divergence (D) may be similarly defined by introducing a 90 degree rotated, outward pointing, version of $\delta_i$ denoted as $\partial_i$ so that $$D := \sum_i \partial_i \cdot v_i \bigg/ \sum_i |\partial_i|$$

where $$\partial_i = \frac{\|x_{i+1} - x_i\| n_{i+1,i} + \|x_i - x_{i-1}\| n_{i,i-1}}{2}$$

The curl of the velocity field (C) would provide a strong indication of the presence of rotors while the divergence of the velocity field (D) would provide a strong indication of focal source or collision site. The sign of the divergence can then be used to distinguish a focal source location from a collision site. Since $\partial_i$ was defined to be an outward pointing normal then the path integral would be positive for a focal source and negative for a collision site.

Derived quantities C and D can be displayed on the 3D geometry using a mapping system. Color maps of C and D can be used to locate regions of high and low curl and divergence indicating potential existence of rotors, focal sources or collision sites.

Figure 15:
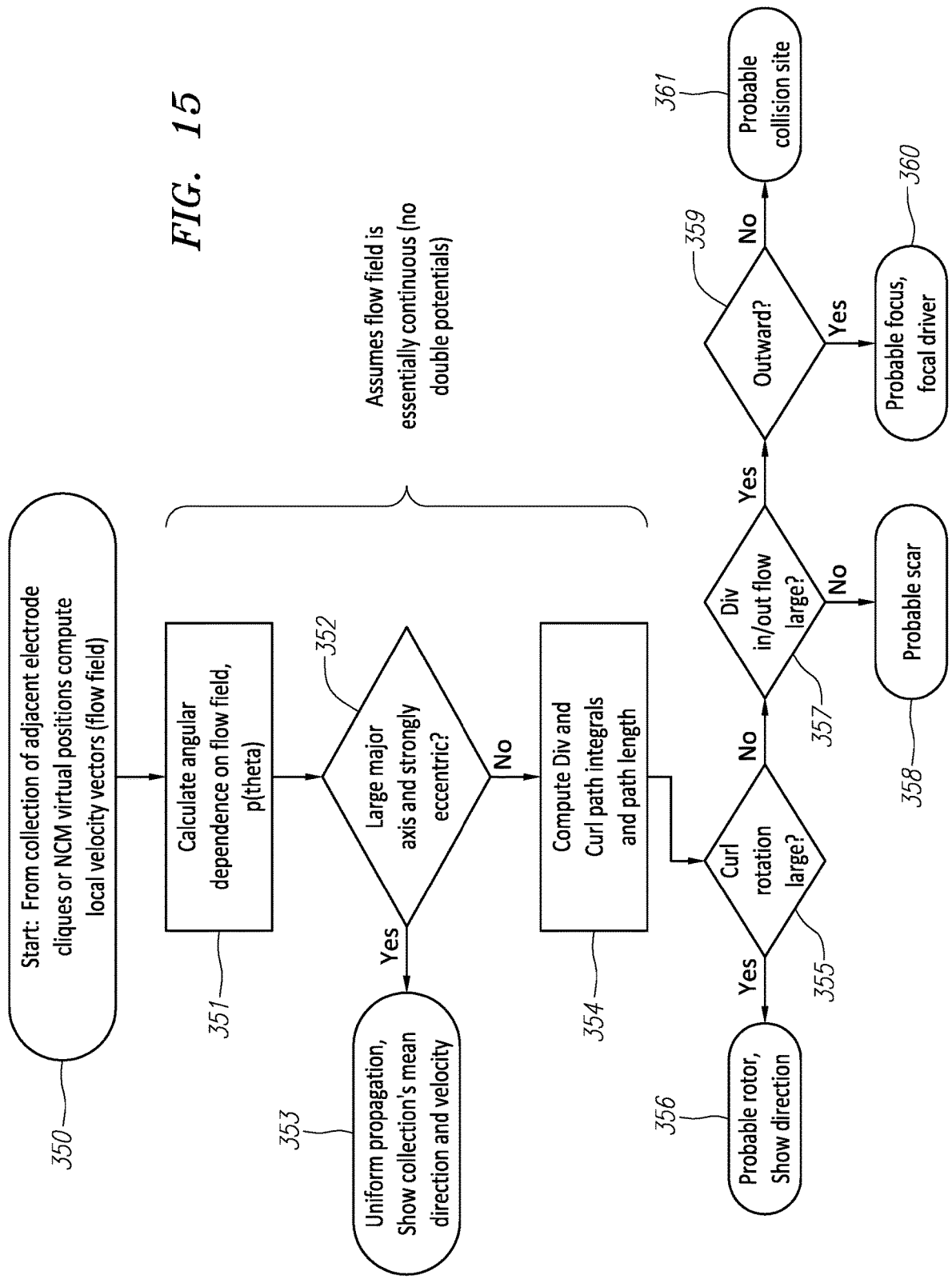
FIG. 15 is a flowchart showing a step-by-step approach to identify uniform propagation, focal sources and rotors.

FIG. 15 illustrates a flowchart showing a step-by-step approach to identify focal sources and rotors using path and surface integrals of local conduction velocity determinations. This classification algorithm depends on reasonably correct velocity vector determinations not confused by double potentials, should they exist. The result enables automatic rhythm classification of uniform propagation, rotor, scar, focus, and collision sites. The method illustrated in the flowchart can comprise the following steps:

At step 350, compute the local velocity vectors from a collection of adjacent electrode cliques or non-contact mapping virtual positions.

At step 351, calculate the angular dependence of flow field p(theta).

At step 352, determine whether a large major axis is present and whether there is strong eccentricity.

If there is a large major axis and strong eccentricity proceed to step 353. At step 353, uniform propagation has been established and the mean direction and velocity of the collection of adjacent electrode cliques can be shown.

If there is not a large major axis and strong eccentricity proceed to step 354. At step 354, compute the Divergence and Curl path integrals and the path length.

At step 355, determine whether the curl rotation is large from a sufficiently large positive or negative value of C corresponding to a counterclockwise or clockwise rotation.

If the curl rotation is large proceed to step 356. At step 356, it is determined that there is a probable rotor at the location where the collection of adjacent electrode cliques was taken and the direction of the rotor can be shown.

If the curl rotation is not large proceed to step 357. At step 357, determine whether the divergence in/out flow is large from large positive or negative values of D respectively.

If the divergence in/out flow is not large proceed to step 358. At step 358, it is determined that there is probable scar at the location where the collection of adjacent electrode cliques was taken.

If the divergence in/out flow is large proceed to step 359. At step 359, determine whether the div flow is outward.

If the divergence flow is outward or positive proceed to step 360. At step 360, it is determined that a probable focus or focus driver is present at the location where the collection of adjacent electrode cliques was taken.

If the divergence flow is not outward proceed to step 361. At step 361, it is determined that a probable collision site is present at the location where the collection of adjacent electrode cliques was taken.

FIG. 16 depicts a table showing P (propagation), C (curl), and D (divergence) of velocity and their characteristic values and shapes expected for uniform wavefront propagation, rotors, focal sources and collision sites. The table shows that a uniform propagation 370 is suggested when propagation is strong and eccentric, the curl is small, and the divergence is small. A rotor 371 is suggested when propagation is weak, the curl is large, and the divergence is small. A focal source 372 is suggested when the propagation is weak, the curl is small, and the divergence is large and positive. A collision site 373 is suggested when the propagation is weak, the curls is small, and the divergence is large and negative. A scar 374 is suggested when the propagation is weak, the curl is small, and the divergence is small.

Figure 17:
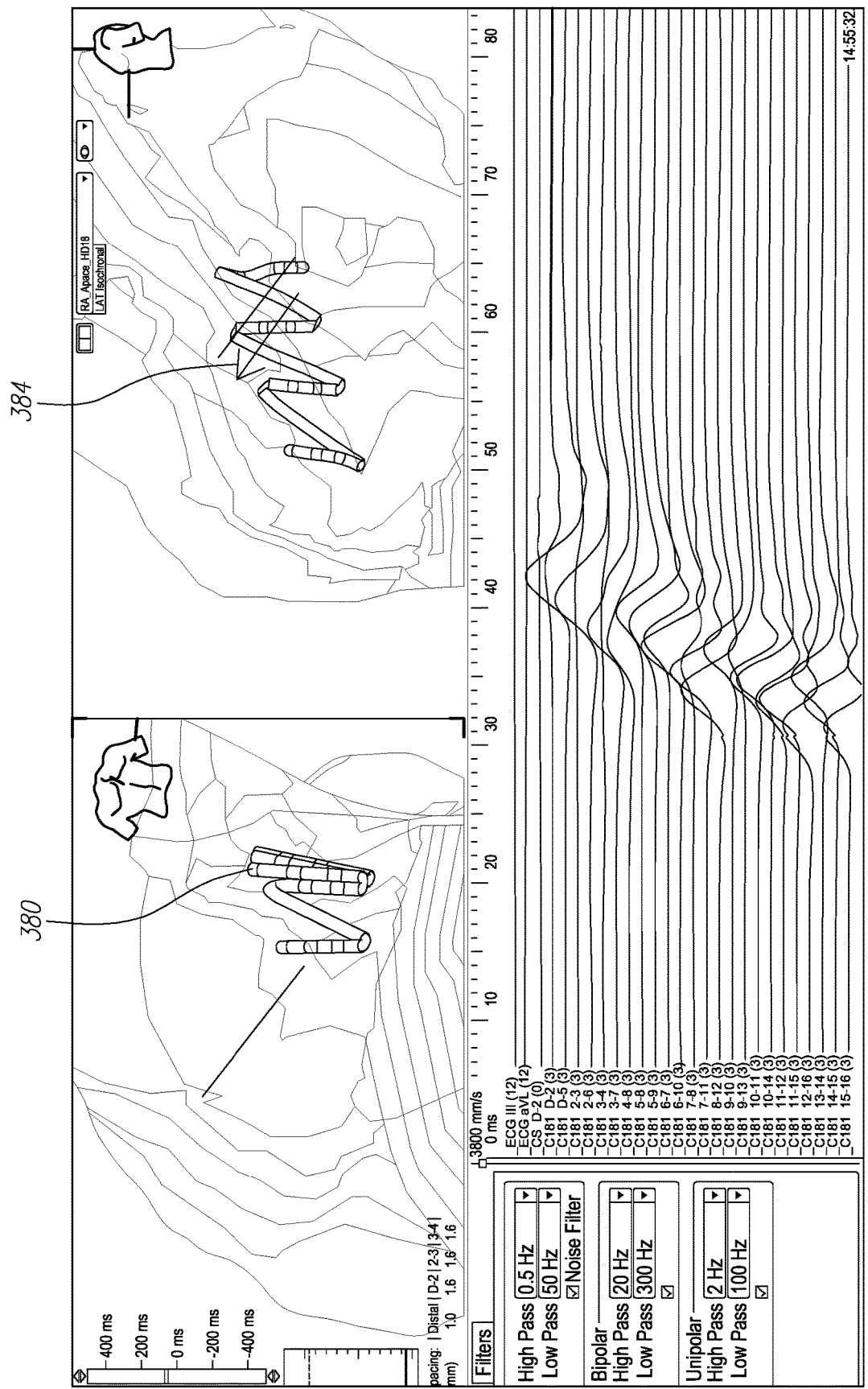
FIG. 17 is a diagram showing the activation pattern near a paddle catheter on a target tissue.

A recorded segment and time when the paddle catheter was placed along the septal wall of the right atrium was located and signals studied to estimate the parameters discussed in the previous section. FIG. 17 depicts two views of a combined map showing a paddle catheter comprising a plurality of electrodes 385, and the location of the paddle catheter in the right atrium on a septal wall. The paddle catheter is situated against a surface of a fossa ovalis in the right atrium. The combined map further shows a plurality of isochrones 383 and an activation direction 384 of a mapped electrical signal. The plurality of isochrones 383 can be used to estimate conduction velocity magnitudes with various colors representing various different velocities. The EGM and position signals from the catheter's electrodes 385 were exported, along with a bipolar contact map of the LAT near the region of the catheter. The LAT map and its contours can be used to roughly predict an activation direction and velocity (a traditional approach). Because the procedure used during this activation was pacing from the CS, the expected activation direction 384 would be mostly anterior (−Y) and superior (+Z) with very little left/right (+/−X) component in the mapping system frame of reference. Conduction velocity, based on rough estimation using distances and color scales in the vicinity of the catheter, is expected to be around 1.0 mm/ms. As can be observed from comparing the left panel 381 and the right panel 382, spline one 380 of the paddle catheter was off the surface of the atrium and hence the electrodes of spline one 380 were not considered for analysis. For the purpose of validation, cliques comprising four electrodes (two from each pair of adjacent splines as seen in FIG. 18 were used.

Figure 18:
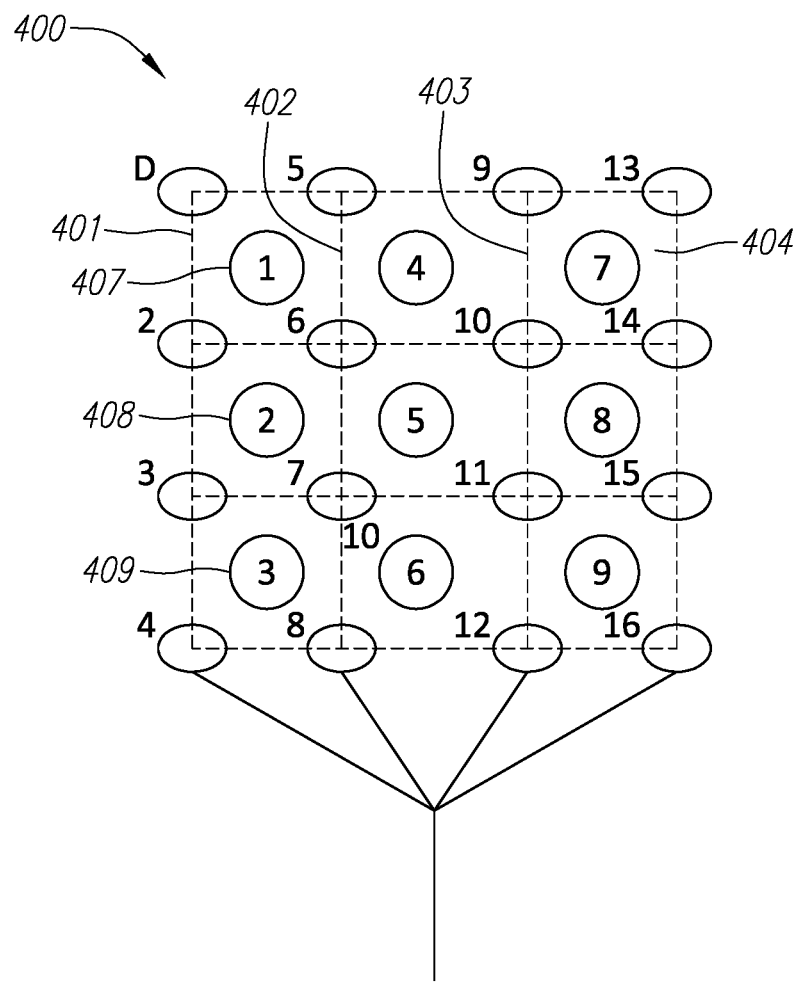
FIG. 18 is a diagram of a paddle catheter and the electrodes and rectangular cliques present on the paddle catheter.

FIG. 18 illustrates the paddle catheter 400 and the cliques used for the computation illustrated in FIG. 17. The paddle catheter 400 can comprise a first spline 401, a second spline 402, a third spline 403, and a fourth spline 404. Each of the splines can comprise four electrodes. Rectangular cliques one 407, two 408, and three 409, comprising electrodes (D,3,6,5), (2,3,7,6), and (3,4,8,7) respectively were not considered as spline one 401 (electrodes D,2,3,4) was deemed to be not in contact with the cardiac surface.

Figure 19:
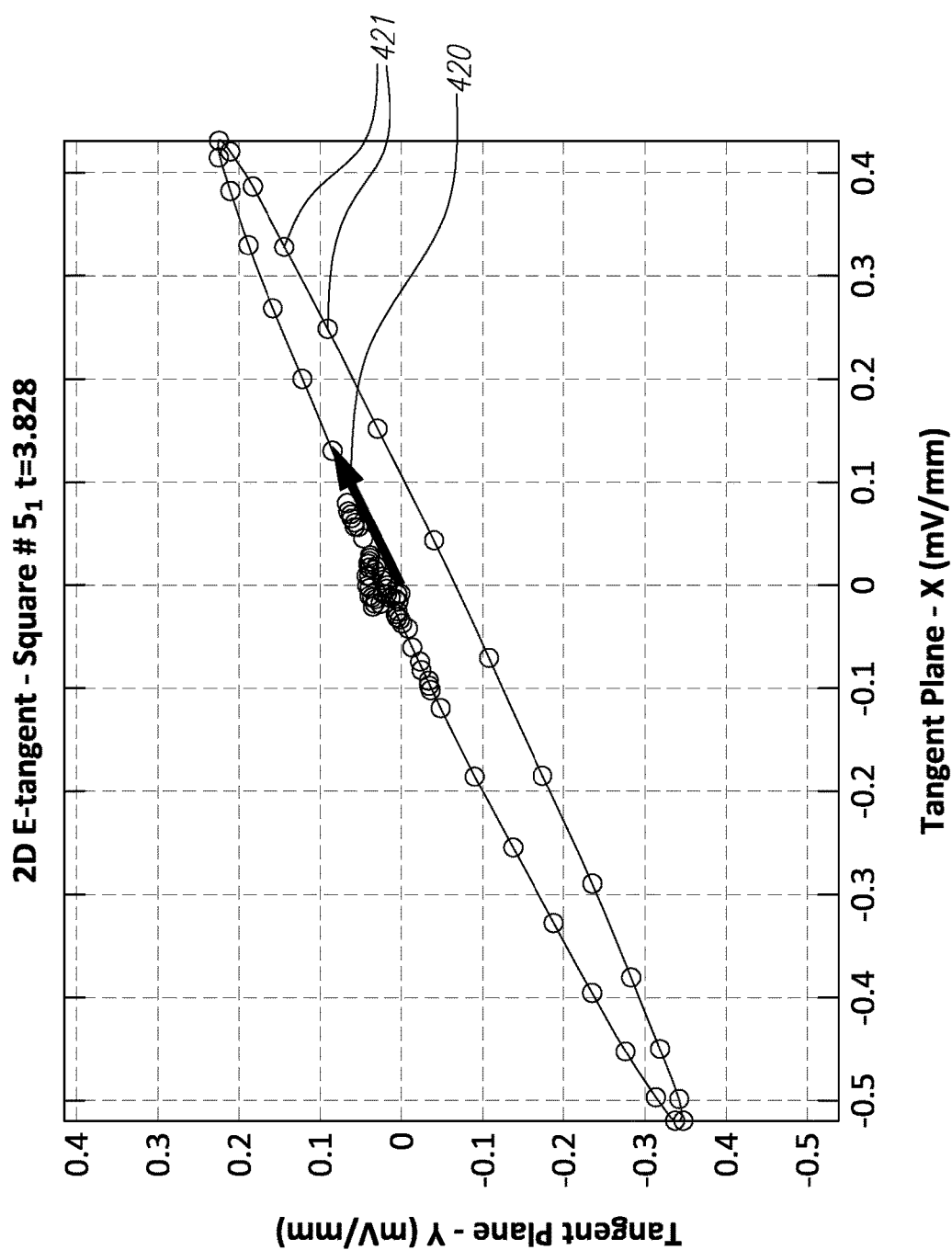
FIG. 19 is a graph of the trajectory of vector $E_t$ over a single beat.

FIG. 19 shows the loop trajectory of vector $E_t$ 420 in the tangent plane over 100 ms of the cardiac cycle when the catheter electrodes see atrial depolarization action. If the wavefront passes the clique electrodes progressing uniformly in a homogeneous medium (as seen in FIG. 4), then vector $E_t$ 420 should comprise voltage swings along a dominant axis aligned with the activation direction. The activation direction, calculated using the method described in the previous section is shown using the arrow. The plot shows the trajectory of vector $E_t$ 420 over a single beat. The tail of the vector is at the isoelectric origin and the plurality of dots 421 indicate the head of the E field vector. The vector sweeps a loop around the origin with maximum and minimum excursions along the activation direction (indicated with the arrow).

Figures 20A, 20B:
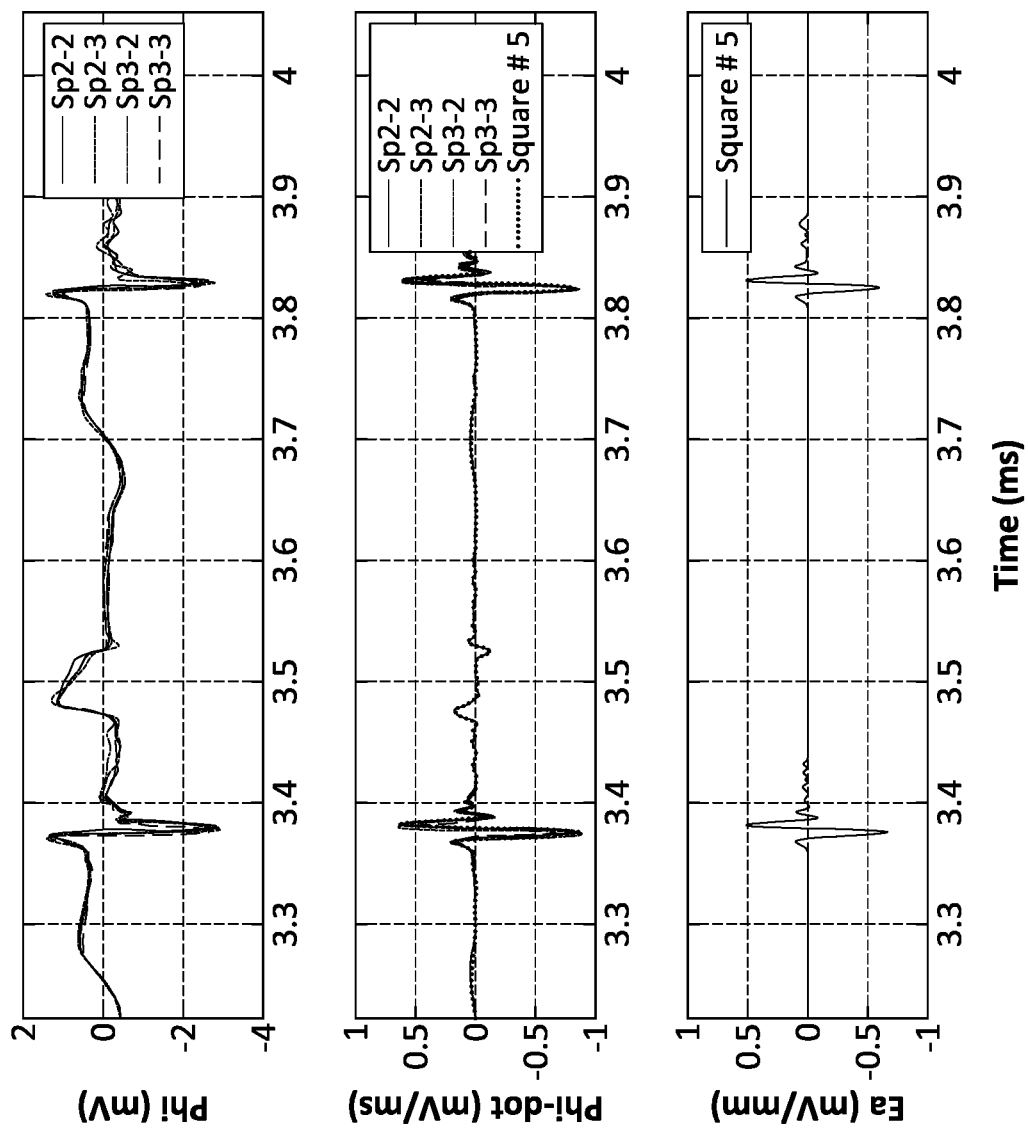
FIG. 20A is a graph showing the EGM signals and equivalent bipole or omnipole $E_a$ vs. time.
FIG. 20B is a line drawing of a shape of an exemplary $E_a$.

FIG. 20A shows the EGM's and the "equivalent bipole" $E_a$ plotted as a function of time for two of the beats that were exported. Note that the morphology and amplitude of the signal is consistent from one beat to the other and that the far-field ventricular signal that we see in the unipolar EGM's is absent. The exemplary $E_a$ has a sharp negative deflection followed by a sharp positive deflection. Also, its amplitude is expected to be solely a function of the substrate that is being investigated. FIG. 20B shows the stylized shape of an exemplary $E_a$ with a sharp negative deflection followed by a sharp positive deflection.

Due to various factors that contribute to non-ideal conditions, including finite spatial separation of electrodes, the morphologies of $\dot{\varphi}$ and $E_a$ do not match exactly but they are very close to proportional. As a result the velocity magnitude is not uniform over the time interval of the beat. Also, when one or both of $\dot{\varphi}$ and $E_a$ of Equation 8 approaches zero, the algorithm fails to produce meaningful results. Under ideal conditions, $\dot{\varphi}$ and $E_a$ would tend to zero at the same instant in time and in the limit when they both tend to zero the ratio could be meaningfully evaluated to be the conduction velocity magnitude. In practice zero crossings of the denominator and numerator play havoc with this ratio.

The practical limitations can be overcome by realizing that classic unipolar signal recorded at an electrode includes contributions from depolarizing tissue upstream and downstream of the electrode location. The information about depolarizing tissue immediately under the electrode is contained within the region of maximal −dv/dt, peak negative deflection, and the immediate up stroke following the unipolar peak negative. This corresponds to the region contained within the peak negative and the subsequent positive peak in $\dot{\varphi}$ and $E_a$. This region can be seen as time interval 501 in FIG. 21. Conduction velocity is calculated using information from the signals within this region.

Listed below are some practical ways to calculate the velocity of activation or propagation. One way is to calculate the velocity as the ratio of the peak-to-peak values of $\dot{\varphi}$ and $E_a$. The conduction velocity estimations shown in this section have been evaluated using this method. An equivalent mathematical way to represent a ratio of peak-to-peak values is shown with definite integrals below.

$$v = \frac{\int_{t_a}^{t_b} \frac{d\dot{\varphi}}{dt} dt'}{\int_{t_a}^{t_b} \frac{dE_a}{dt} dt'} \quad (12)$$

In another embodiment the conduction velocity can be calculated by applying different weights to the information contained within the interval $(t_a < t' < t_b)$ as follows $$v = \frac{\int_{t_a}^{t_b} w \frac{d\dot{\varphi}}{dt} dt'}{\int_{t_a}^{t_b} w \frac{dE_a}{dt} dt'} \quad (13)$$

where w is a weighting function. The weighting function can be used to ensure that more importance is given to certain regions within the time interval as shown in FIG. 22 and discussed below.

Figure 21:
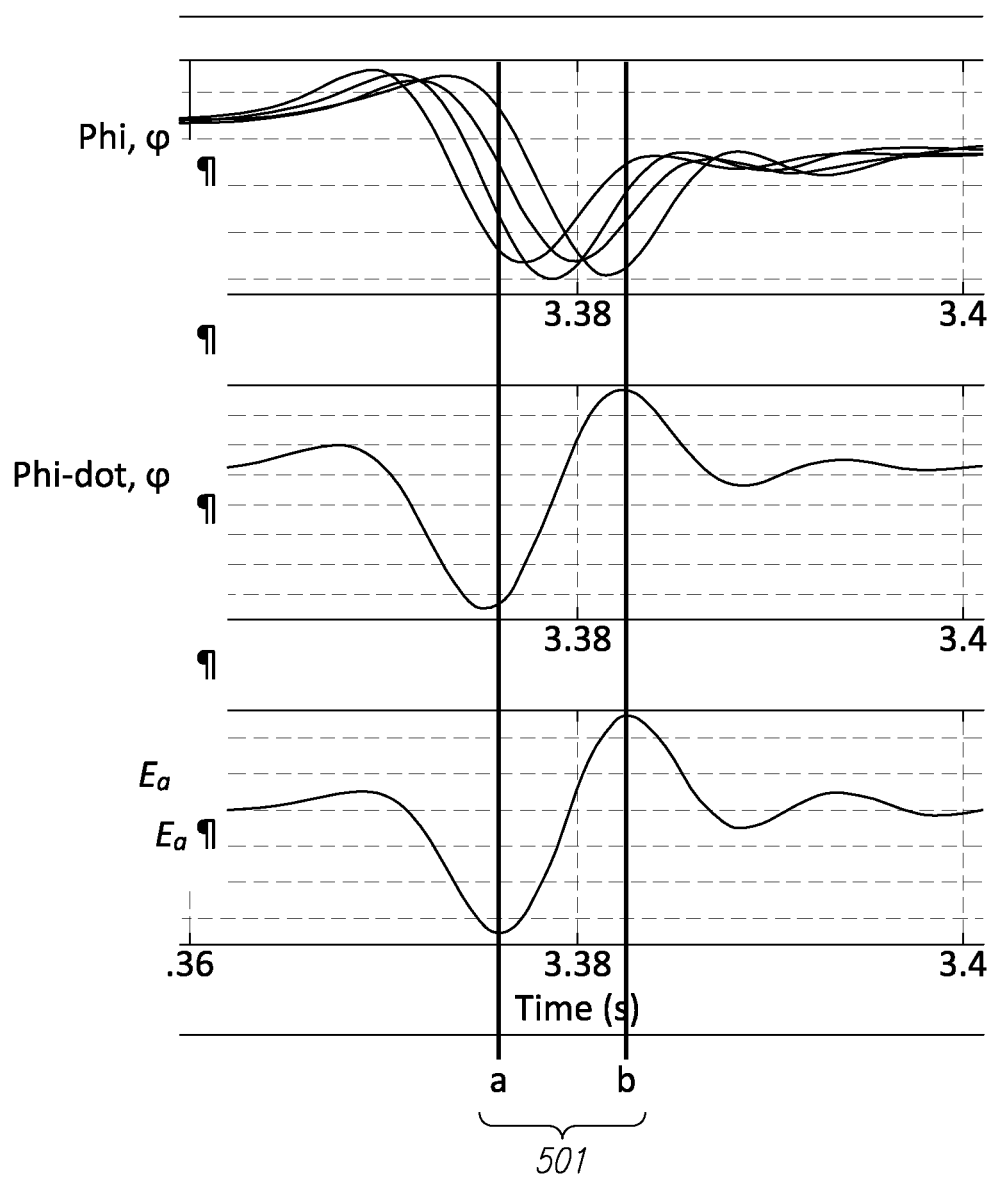
FIG. 21 is a graph showing the time interval that holds the most information about depolarizing tissue under a particular clique of electrodes.

FIG. 21 illustrates a plot showing the time interval (from a to b) 501 that holds the most information about depolarizing tissue under a particular clique of electrodes. This generally corresponds to times around when the unipolar voltage is most negative which is when the inward current of depolarization is maximum under the electrodes of the clique. This introduces a practical and improved means to derive velocity from local $\dot{\varphi}$ and $E_a$ signals.

Figure 22:
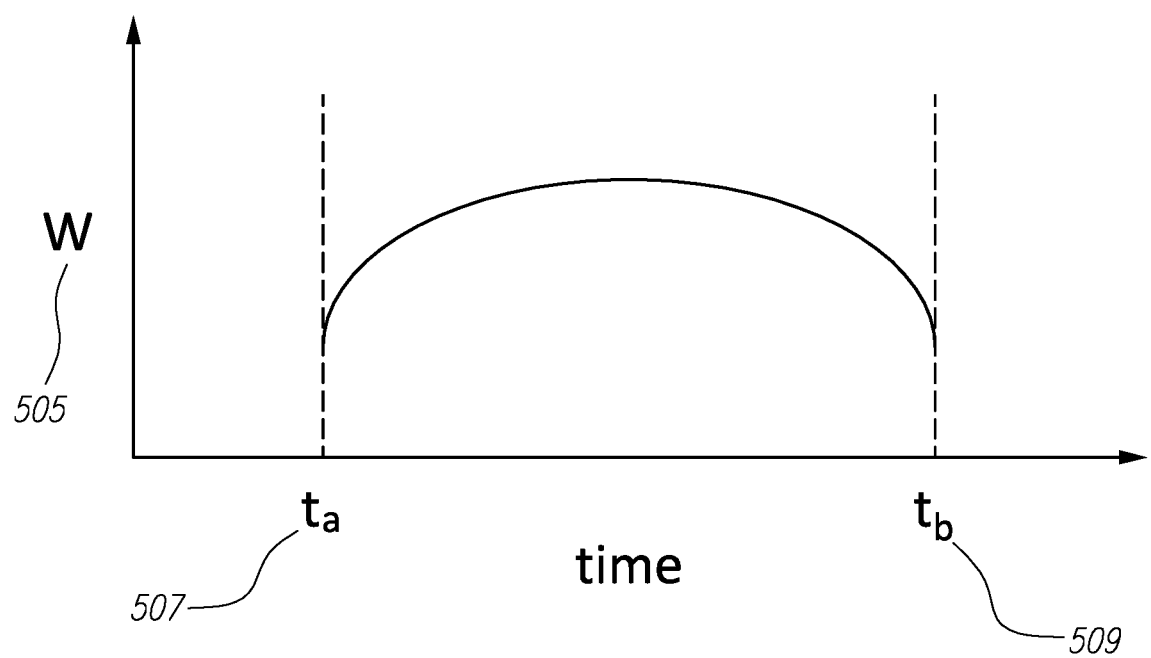
FIG. 22 is a plot showing the weighting function vs. time.

FIG. 22 depicts a weighting function w vs. time. W 505 is shown between time $t_a$ 507 and time $t_b$ 509. In this illustration w is chosen to ensure more importance is given to the region corresponding to the zero-crossing of $E_a$ following its pk-neg.

Figure 23:
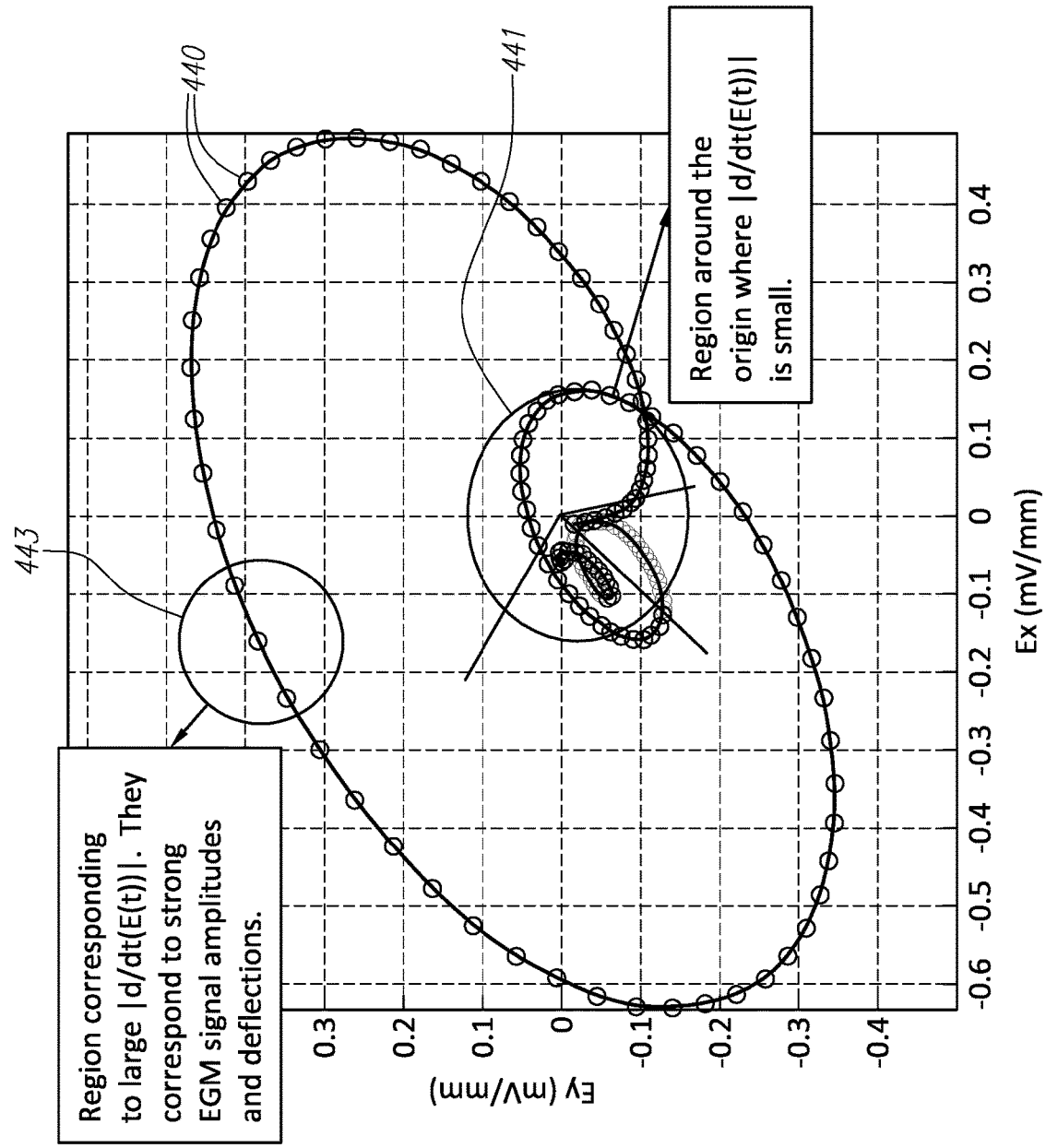
FIG. 23 is a graph of an E-field loop showing regions of large and small $|d/dt(E(t))|$.

In some embodiments, determining the activation direction from the E field loop data can be overly sensitive to data taken when the loop is nearly isoelectric. OIS signals and derived quantities may reflect artifacts due to filtering, offsets, far field effects, or waveform complexity when good information also exists. The artifacts can be minimized by weighting the loop points in calculations, including activation direction cross correlation, not equally by time, but proportional to, or as a monotonic function of, $|d/dt(E(t))|$ as seen in FIG. 23. This can ensure that the E field data points that lie close to the origin or are changing slower than the depolarization, as seen in FIG. 23, are given less weight.

Only the major deflections, which provide the necessary and key information about the underlying substrate, are then used for deriving OIS quantities, including the OIS coordinate frame ($\hat{n}$, $\hat{a}$, $\hat{w}$) and omnipole signals $E_n$ and $E_a$. This can concentrate OIS results on the information containing part of the loop when the E field changes rapidly. This weighting can further be used in deriving OIS coordinate directions entirely from the E field loop, which could also lead to more accurate determination of $E_n$ peak-to-peak, $E_a$ peak-to-peak, and conduction velocity magnitude.

FIG. 23 illustrates an E-field loop showing regions of large and small $|d/dt(E(t))|$. The points 440 are EGM derived E-field points equally spaced in time. As discussed above, closely spaced points contain little information and contain artifacts that can affect OIS derived signals and EP characteristics. The area around the origin 441 has a small $|d/dt(E(t))|$, while the area with a large $|d/dt(E(t))|$ corresponds to strong EGM signal amplitudes and deflections. The area with a large $|d/dt(E(t))|$ is of more interest. As a result, in one embodiment, those areas with a small $|d/dt(E(t))|$ can be removed or deemphasized.

In another embodiment, the loop points can also be weighted based on the magnitude of the E-field (norm(E)) which is the distance from the isoelectric origin. FIGS. 22A and 22B show the tangent E-field loop points before and after weighting based on the method described herein. FIG. 24A illustrates the tangent E-field loop 451 before weighting. FIG. 24B illustrates the tangent E-field loop 455 after weighting the loop points 457 based on the norm of the E-field. As can be seen in the comparison of FIGS. 22A and 22B, the part of the loop that contains the most useful EP information is accentuated and hence more meaningful OIS characteristics can be obtained from the weighted loop.

Figure 25B:
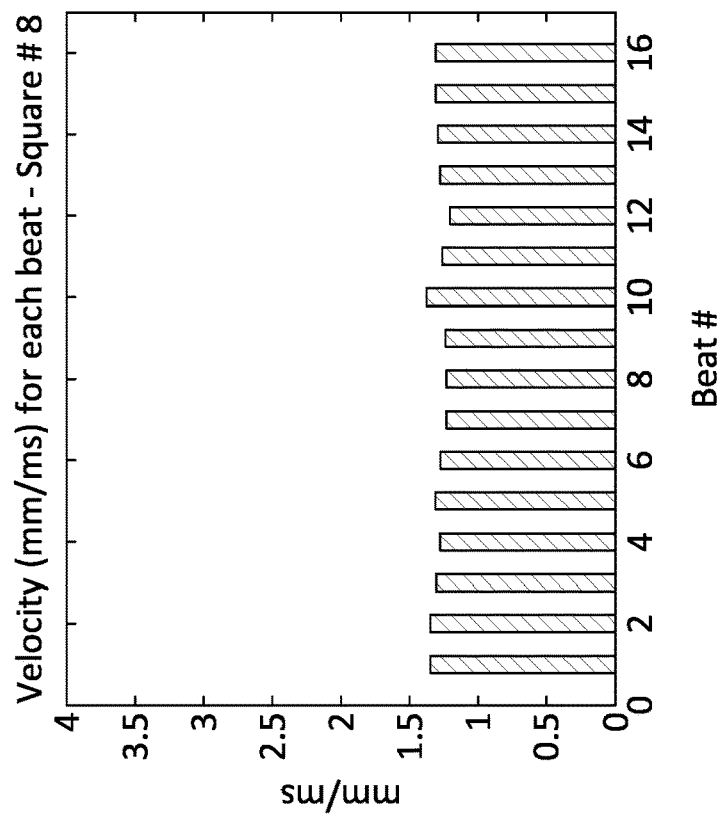
FIGS. 25A and 25B are graphs showing the conduction velocity estimated from two cliques over successive beats.
Figure 25A:
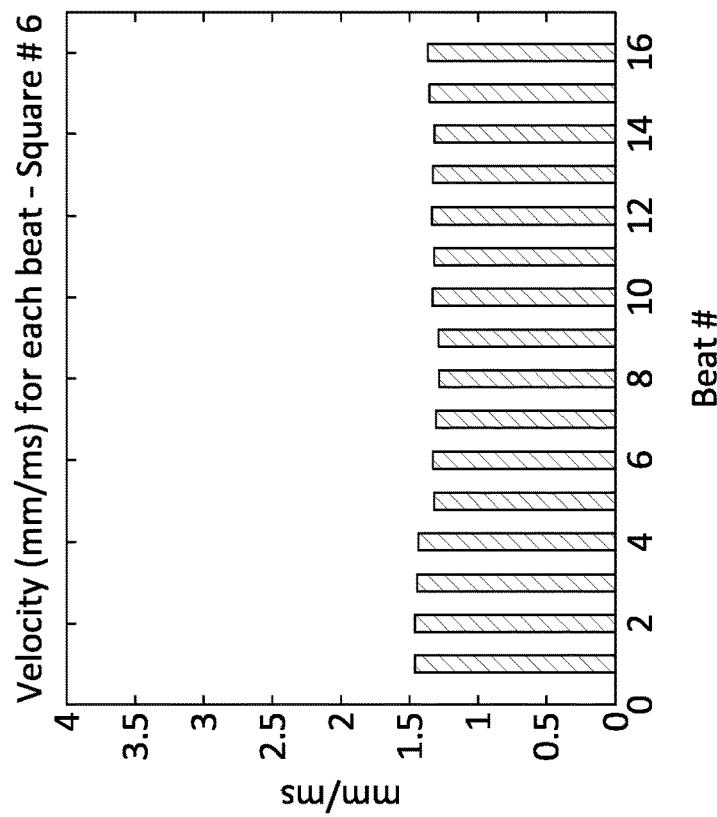

FIGS. 25A and 25B show the magnitude of conduction velocity estimated for each beat on the RA septal wall for two different cliques. FIG. 25A shows the magnitude of the conduction velocity for clique 6 and FIG. 25B shows the magnitude of the conduction velocity for clique 8. The velocity magnitude was estimated by taking the ratio of the peak-to-peak values of $\dot{\varphi}$ and $E_a$. The beat-to-beat variation in conduction velocity magnitude is minimal and the values of around 1.3 mm/ms are roughly what was expected. Conduction velocity magnitude and activation direction (unit vector) estimated for the two adjacent cliques were as follows:

Clique #6
  Velocity magnitude=1.35± 0.06 mm/ms
  Activation direction=(0.12, −0.91, 0.40)
Clique #8
  Velocity magnitude=1.29± 0.05 mm/ms
  Activation direction=(0.10, −0.80, 0.58)

The activation direction and velocity calculated were similar and consistent with expected results in atrial tissue.

Figure 26:
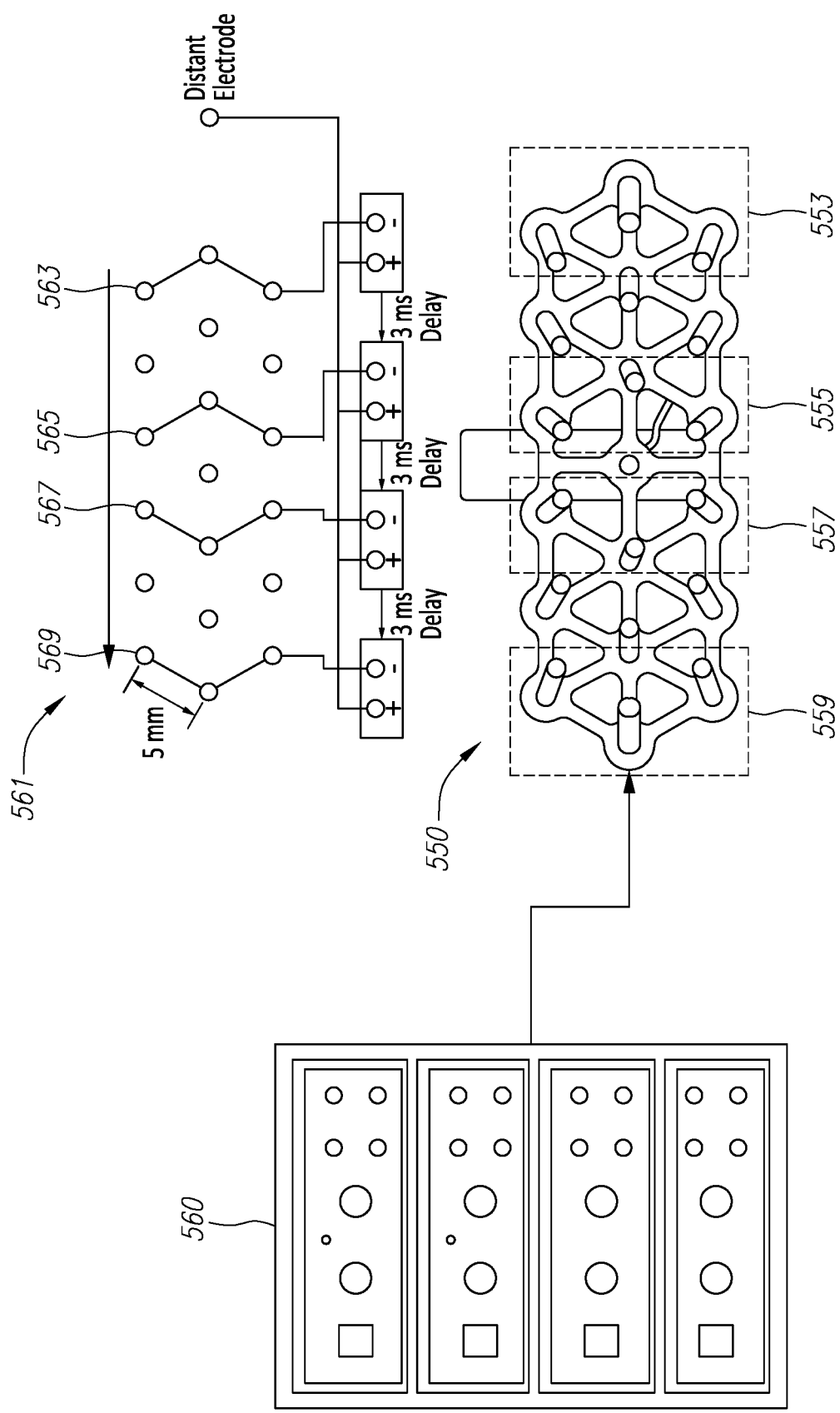
FIG. 26 is a diagram of a saline tank test apparatus to simulate wavefront propagation.

FIG. 26 illustrates a saline tank test apparatus setup to simulate wavefront propagation with the horizontal source array 550. Wavefront propagation was setup in the test apparatus using a horizontal source array 550 by firing the electrodes on the array sequentially with a 3 ms delay to mimic wavefront propagation. Sets of 3 source electrodes (first set 553, second set 555, third set 557, and fourth set 559) separated by 10 mm were driven sequentially separated by 3 ms to summate in the neighboring saline and resemble propagation in vitro. The conduction velocity at the source array electrodes is thus 10 mm/3 ms=3.33 mm/ms. Derived from physical measurements, this conduction velocity serves as a reference for subsequent determinations by traditional and orientation independent means. Each set of electrodes is driven by a single channel generator 560. A source array electrical diagram 561 is also illustrated showing a first set of electrodes 563, a second set of electrodes 565, a third set of electrodes 567, and a fourth set of electrodes 569.

When positioned at its standard location in the saline tank test apparatus, wavefront propagation in the apparatus should be about equal in the right (−X) and anterior direction (−Y) direction with virtually no component in the superior (+Z) direction. As a result the unit activation direction vector is predicted to be (−0.71, −0.71, 0).

Figure 27:
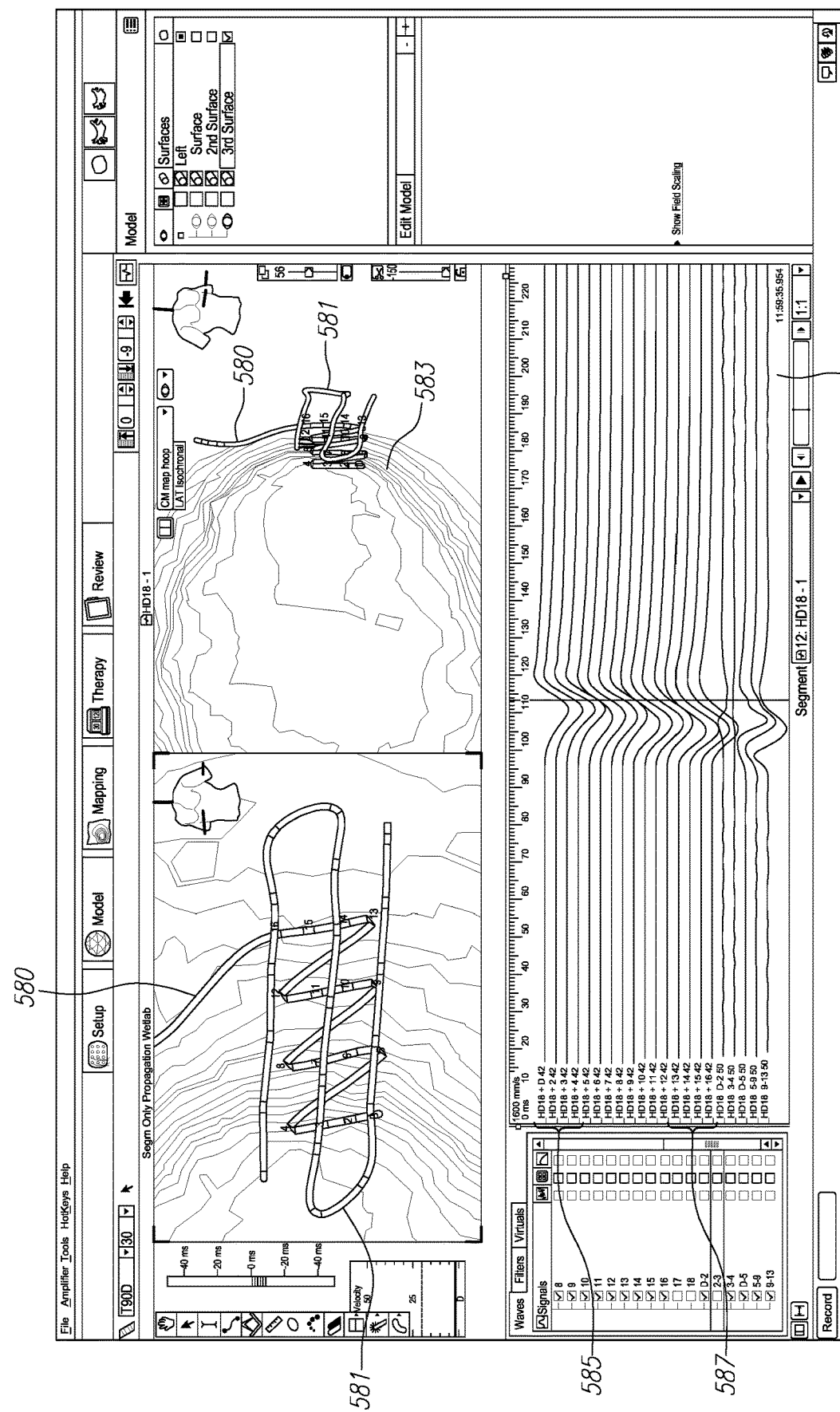
FIG. 27 is a diagram of a paddle catheter in the saline tank test apparatus of FIG. 26.

FIG. 27 shows a paddle catheter 580 in the saline tank test apparatus near the horizontal source array 581 simulating propagation. Wavefront propagation direction and velocity can be estimated from a gradient LAT map made from multiple precise contact map points on a spherical surface 583 near the source array electrodes. In one embodiment, the LAT map can comprise color gradients as known to those in the art. The earliest unipolar signals occur on the first set of waveforms 587 in the waveform window 589 on electrodes 13-16. The last unipolar signals occur on the second set of waveforms 585 on electrodes D-4. Using the precision contact map for activation times (± 0.5 ms due to sampling) and the measured interelectrode distances, a conduction velocity of 3.6 mm/ms (± 10% due to sampling) was determined at the center of the source array. This is close to the reference velocity of 3.33 mm/ms.

Figure 28:
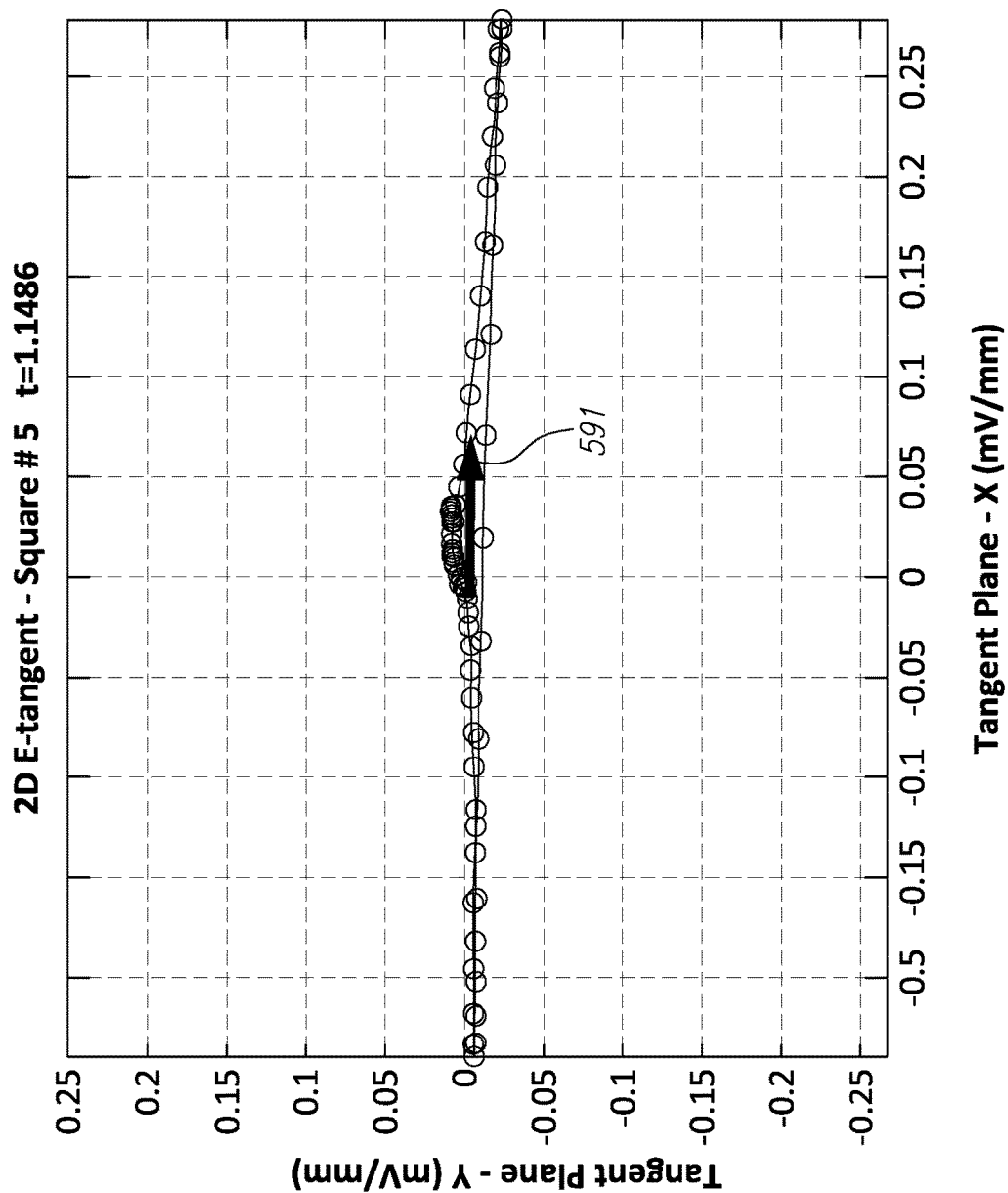
FIG. 28 is a graph showing vector $E_t$ and the activation direction over one saline tank test apparatus beat.
Figure 29:
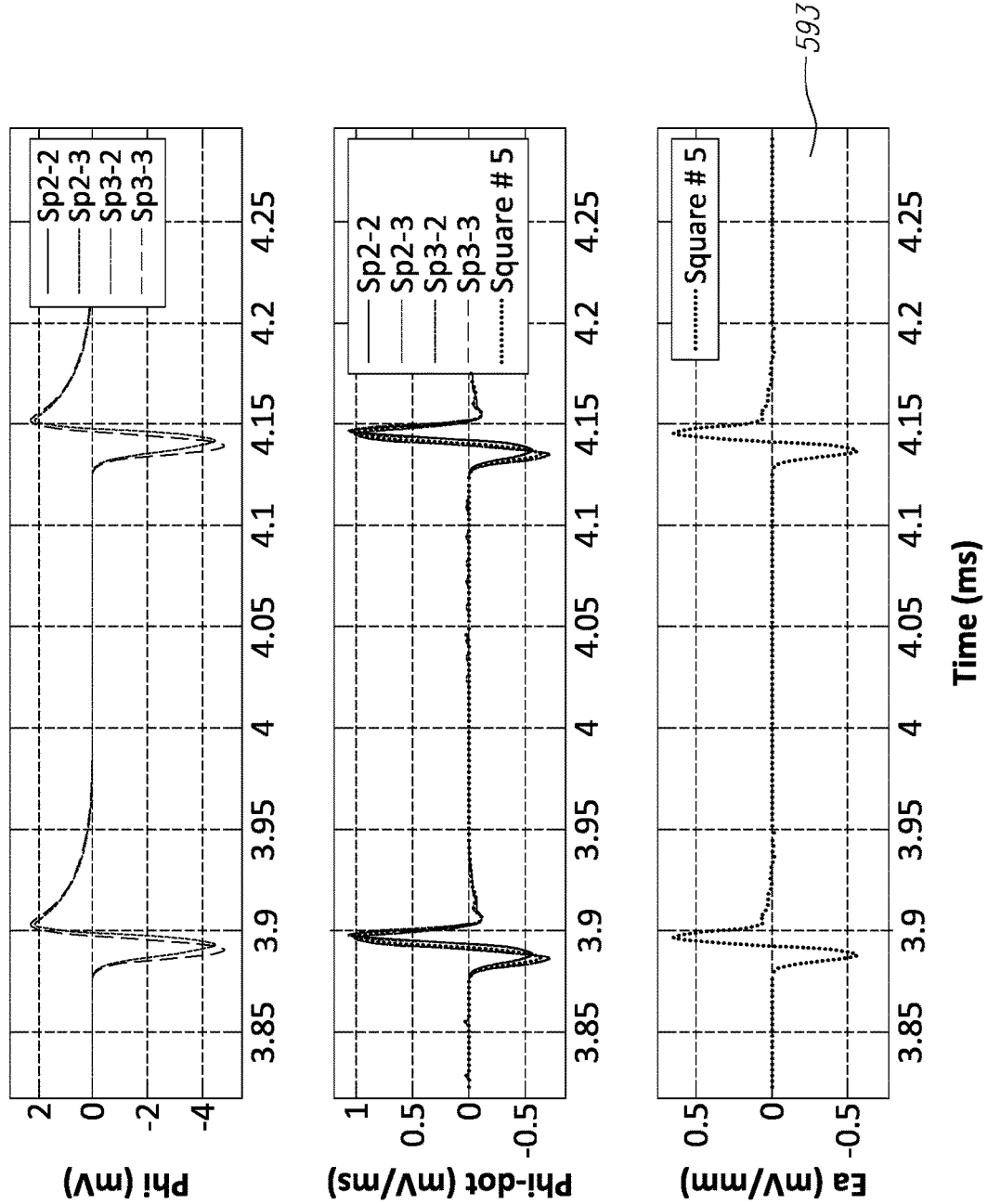
FIG. 29 is a graph showing $\dot{\varphi}$ and $E_a$ vs. time for two successive beats.

FIGS. 28 and 29, show plots of $E_t$, $E_a$, and conduction velocity derived from the paddle catheter in the same saline tank test apparatus propagation model discussed previously. Note that the $E_a$ morphology is very similar to the exemplary signal discussed in the previous section. The conduction velocity and activation direction derived from OIS orientation independent fundamentals of wavefront propagation (and thus rely on the mapping system field scaling) was found to be in good agreement with the precision contact map and the reference values of 3.6 and 3.3 mm/ms respectively.

Clique #5
Velocity magnitude=3.48± 0.02 mm/ms
Activation direction=(−0.79,−0.61,−0.02)

FIG. 28 illustrates a plot showing vector $E_t$ 591 and the activation direction in the test apparatus over one beat. The action occurs in essentially a single direction, that of activation. FIG. 29 illustrates a plot showing omnipole $E_a$ vs. time 593 in the test apparatus propagation model. Note that the signal has the exemplary shape discussed in the previous section and shown from in vivo data in FIG. 20B.

The split tip catheter discussed previously is also suitable for bipolar pacing in a manner that is much more tip localized than the conventional D-2 bipolar pacing and free of the concern over variable locational of capture (and variable thresholds) that can occur when the ring (and not the tip) captures myocardium. This is a great advantage when, for example, pacing is being done to establish lesion efficacy. The alternative, unipolar pacing, involves a distant electrode and thus is responsible for a large pacing artifact that complicates use of pacing for assessing blocks. The basic idea is that pacing is accomplished by assigning alternating polarities to the four tip electrodes. This too may be accomplished by circuit elements such that the four electrograms and mapping system positions remain distinct and yet the tip appears as a "crossed bipole" from the standpoint of pacing. Alternatively this may be done by employing the stimulator, devoting two simultaneous channels to the four electrodes.

With each local depolarization, a new conduction velocity vector may be generated. The system can be configured to display various information including oriented arrow icons, Matlab quiver-like plots, and ripple maps. The system can further have the option to control the persistence of these direction and/or magnitude renderings. In one embodiment, the default process is to update immediately with each new local depolarization (that meets criteria for a depolarization).

Updates that visually replace prior visual assessments are sometimes preferred over cumulative multi-beat maps because if there is only modest movement of the catheter between repeated similar beats, the map will become cluttered with such representations. As a result, it can be beneficial to include a spatial density criterion (like that currently available with traditional mapping systems). New representation points would be added if none are within say 2 mm of previous points (and from same mapped rhythm if that is distinguished). If old points lie within 2 mm of a new point, the new points can delete or hide old points. Particularly when playing back recorded segments and focus is on a region of interest where a multi-electrode mapping catheter is, the system can hide/delete prior representation points in favor of the most recent cardiac cycle since play back began.

In another embodiment, a variable persistence can be given to the point representations based on, a given number of milliseconds duration and observed during slow playback. The points can come into existence and disappear in a manner that (similar to a propagation map available on the EnSite Velocity mapping system) suggests the wavefront itself (a region of typically 1 cm or so wide that encompasses the 10 ms or so of primary depolarization current and EGM generation). This can benefit the system by removing clutter and focusing attention on immediate events.

Transmural RF ablation possesses certain EGM characteristics which are exploitable by an orientation independent, OIS catheter electrode design and software. In particular, the unipolar signal (which to a first approximation is just a polarity inverted $E_n$ signal) may change from an rS pattern preablation to a r' pattern afterward. As a result, $E_n$ can change from a nice dominant upward deflection to a smaller downward deflection, perhaps a downward deflection that was present previously, but now appears minor in comparison with the upward deflection.

In one embodiment, using a paddle catheter like that illustrated in FIG. 2A and FIG. 18, the regular rectangular arrangement of cliques can be used. Each clique under consideration can receive a score determined for how the pattern in the cliques adjacent to it matches templates for uniform, focal source, and rotational conduction. The templates can be made with unit vectors in a uniform direction, radially inward or outward from clique under consideration, and in a clockwise or counterclockwise orientation perpendicular to the radial directions. Scores can be calculated by taking dot products of the OIS derived CV vectors (preferably unit vectors) computed at the cliques with the corresponding unit vectors on the template.

Figure 30B:
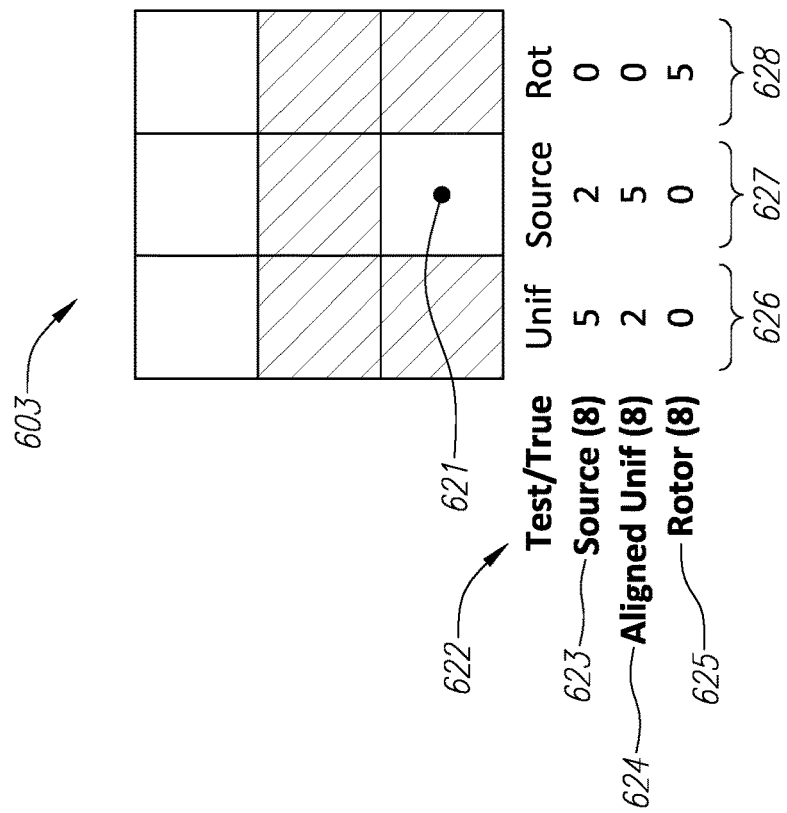
FIGS. 30A and 30B are diagrams of several of the possible types of cliques in a rectangular grid of electrodes and the associated scoring for the cliques.
Figure 30A:
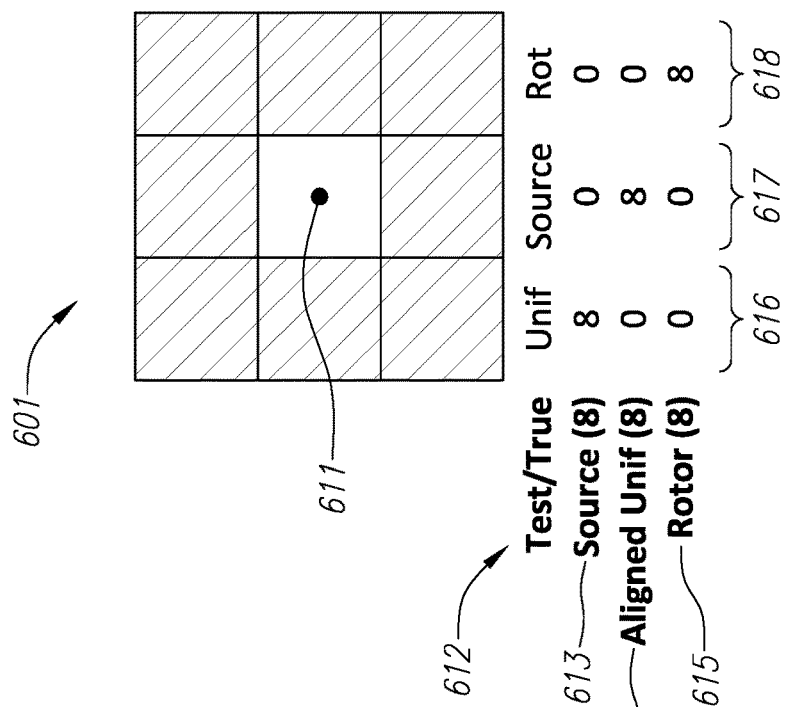

FIGS. 30A and 30B illustrate one embodiment of a scoring system and results for cases when the rectangular clique under consideration is either a center clique 611 or an edge clique 621. The scoring system can be used to determine and display the degree to which the catheter's cliques match uniform propagation, focal source/sink activation, or rotary motion. FIG. 30A shows a nine clique FIG. 601 with a scoring diagram 612 for a center clique 611. The scores from a uniform test pattern 613, a source test pattern 614, and a rotor test pattern 615 are shown when each pattern is compared to a template uniform conduction 616, a template source 617, and a template rotor 618. The maximum score for a center clique 611 in this embodiment is 8, as that is the number of cliques that surround the center clique 611. The scoring diagram 612 illustrates that when comparing the uniform test pattern 613 with template uniform conduction 616, a score of 8 results. When comparing the uniform test pattern 613 with the template source 617, a score of 0 results. When comparing the uniform test pattern 613 with the template rotor 618, a score of 0 results. So if the true or observed pattern was uniform conduction, this would lead to a score of (8,0,0) as described in relation to FIG. 33. When comparing the source test pattern 614 with the template uniform conduction 616, a score of 0 results. When comparing the source test pattern 614 with the template source 617, a score of 8 results. When comparing the source test pattern 614 with the template rotor 618, a score of 0 results. This leads to a score of (0,8,0) for a true source located at 611. When comparing the rotor test pattern 615 with the template uniform conduction 616, a score of 0 results. When comparing the rotor test pattern 615 with the template source 617, a score of 0 results. When comparing the rotor test pattern 615 with the template rotor 618, a score of 8 results. This leads to a score of (0,0,8) for rotation about 611.

FIG. 30B shows a nine clique FIG. 603 with a scoring diagram 622 for an edge clique 621. The scores from a uniform test pattern 623, a source test pattern 624, and a rotor test pattern 625 are shown when each pattern is compared to a template uniform conduction 626, a template source 627, and a template rotor 628. The maximum score for an edge clique 621 in this embodiment is 5, as that is the number of cliques that surround the edge clique 621. The scoring diagram 622 illustrates that when comparing the uniform test pattern 623 with template uniform conduction 626, a score of 5 results. When comparing the uniform test pattern 623 with the template source 627, a score of 2 results. When comparing the uniform test pattern 623 with the template rotor 628, a score of 0 results. This leads to a score of (5,2,0) at 621 as described in relation to FIG. 33. When comparing the source test pattern 624 with the template uniform conduction 626, a score of 2 results. When comparing the source test pattern 624 with the template source 627, a score of 5 results. When comparing the source test pattern 624 with the template rotor 628, a score of 0 results. This leads to a score of (2,5,0) at 621. When comparing the rotor test pattern 625 with the template uniform conduction 626, a score of 0 results. When comparing the rotor test pattern 625 with the template source 627, a score of 0 results. When comparing the rotor test pattern 625 with the template rotor 628, a score of 5 results. This leads to a score of (0,0,5) at 621.

When testing against an observed pattern against a template for uniform conduction, it must be tested multiple times with vectors of the uniform conduction templates facing different directions. In one embodiment, the vectors making up each template are rotated 2 degrees and tested again. This process is repeated with the vectors being rotated through a full 360 degrees each time to ensure that the scoring system can be aligned with actual conduction. In this embodiment, the highest overall score for uniform conduction is then used by the system.

This approach can be further generalized to 2D triangular or quadrilateral cliques such as those that can occur with a helical basket catheter design or more common basket catheter designs. FIG. 30 shows a list of scoring for two of the three types of cliques in the rectangular grid of electrodes seen in FIG. 18. The scoring can involve a variable number of adjacent cliques. The more cliques the higher the possible score for each of the 3 types. Higher scores are associated with greater certainty.

Figure 31:
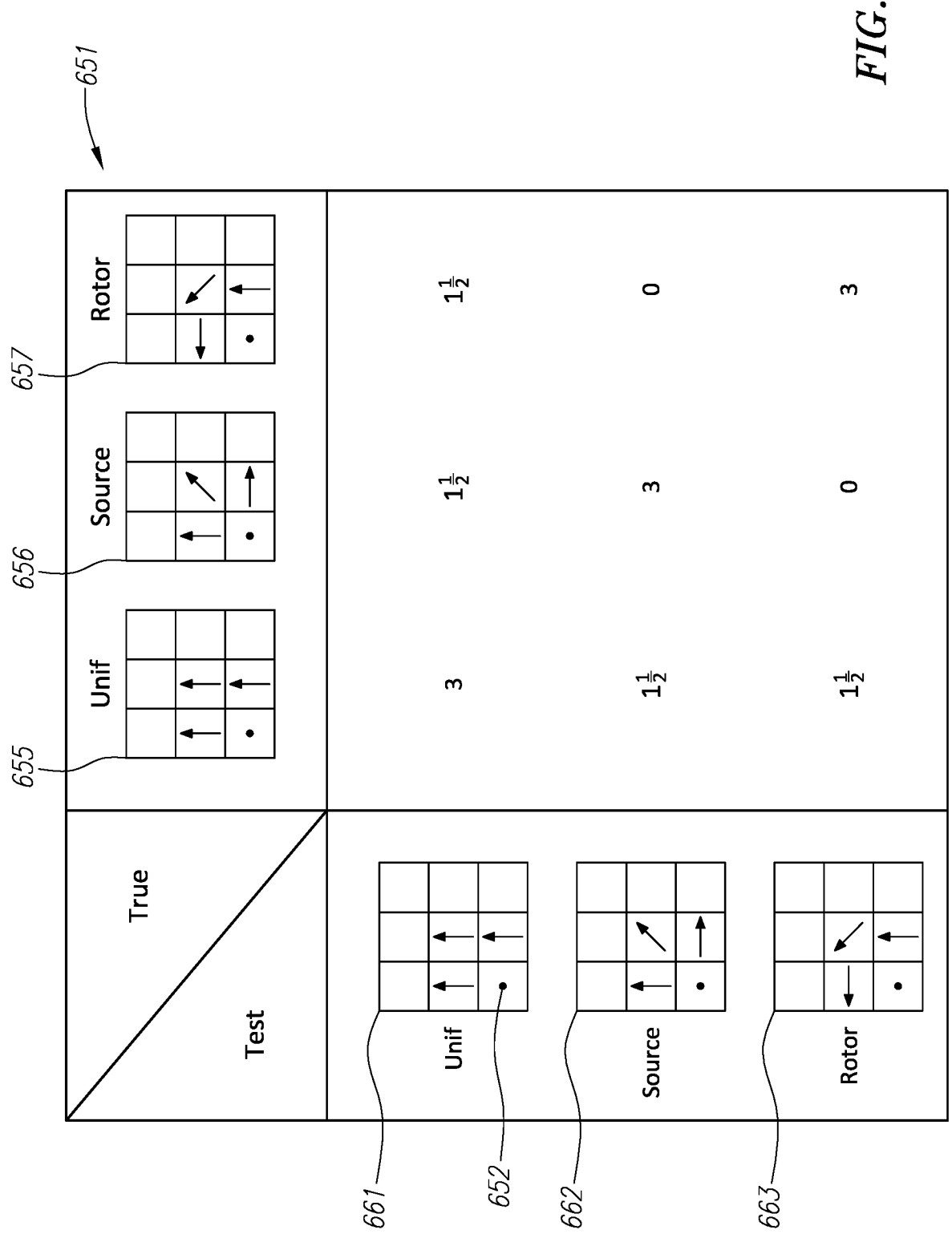
FIG. 31 is a diagram of one embodiment of a scoring system for a corner clique.

FIG. 31 illustrates an more in-depth scoring diagram 651 for a nine clique figure with a corner clique 652. As before, when the observed pattern being tested matches the true template, the scores are highest. In the illustrated embodiment a maximum of 3.0 is shown reflecting the three adjacent rectangular cliques. The lowest scores result from testing a focal source/sink against a rotor or vice versa. The scores from a uniform test pattern 661, a source test pattern 662, and a rotor test pattern 663 are shown when each pattern is compared to a template uniform conduction 655, a template source 656, and a template rotor 657. The scoring diagram 651 illustrates that when comparing the uniform test pattern 661 with template uniform conduction 655, a score of 3 results. When comparing the uniform test pattern 661 with the template source 656, a score of 1.5 results. When comparing the uniform test pattern 661 with the template rotor 657, a score of 1.5 results. This leads to a score of (3,1.5,1.5) at 652 as described in relation to FIG. 33. When comparing the source test pattern 662 with the template uniform conduction 655, a score of 1.5 results. When comparing the source test pattern 662 with the template source 656, a score of 3 results. When comparing the source test pattern 662 with the template rotor 657, a score of 0 results. This leads to a score of (1.5,3,0) at 652. When comparing the rotor test pattern 663 with the template uniform conduction 655, a score of 1.5 results. When comparing the rotor test pattern 663 with the template source 656, a score of 0 results. When comparing the rotor test pattern 663 with the template rotor 657, a score of 3 results. This leads to a score of (1.5,0,3) at 652.

In one embodiment, a conventional 1-D color scale or gray scale coloring scheme can be used for any one of the major patterns (e.g. rotors, uniform conduction or focal source).

Figure 32:
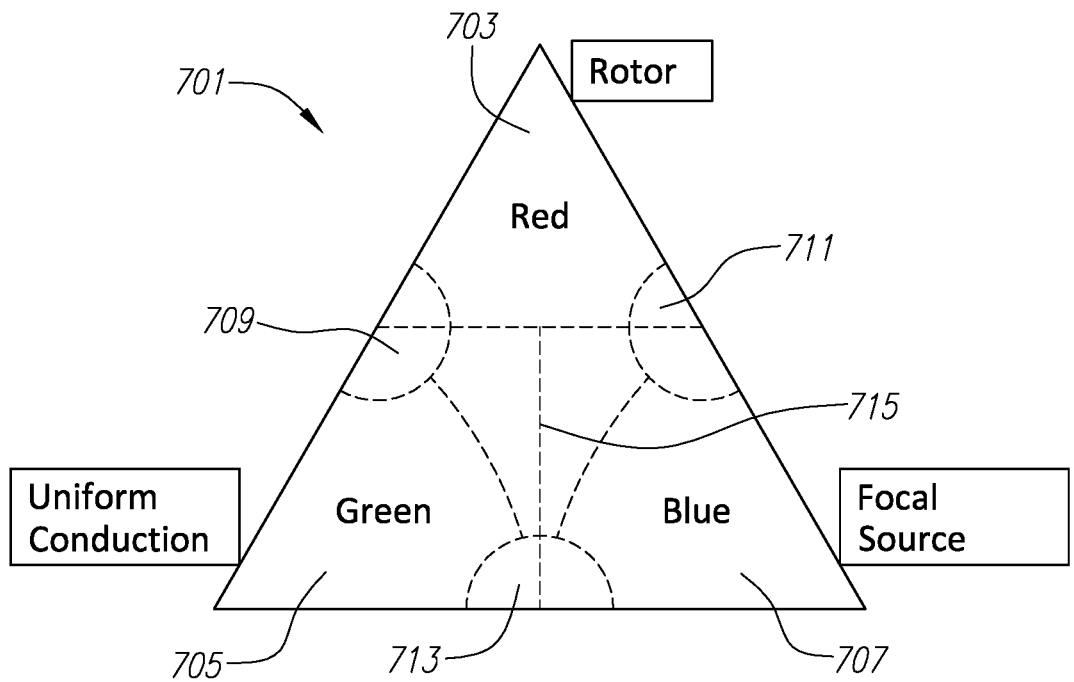
FIG. 32 is diagram of a color triangle capable of associating a specific color to the set of scores for a clique.

However in another embodiment, as illustrated in FIG. 32, a color can be assigned from a color triangle 701 according to each score type. For example, if red 703 is used to represent rotors and green 705 for uniform conduction, then yellow 709 can be used to represent a pattern that resembles a rotor and uniform propagation equally. Similarly, blue 707 can be used to represent a focal source. This would result in a cyan or blue-green 713 being displayed to represent a pattern that resembles a focal source and a uniform conduction equally. Further, purple 711 would be displayed to represent a patter that resembles a focal source and a rotor equally. White or the absence of color 715 can be used to represent a score that equally shows a rotor, a focal source, and a uniform conduction. By using an absence of color, a user would be able to more easily determine that a score is inconclusive. The color triangle 701 can be used to associate a specific color to the set of scores for all of the cliques. The absolute value of scores can be used so that both rotor directions (clockwise and counterclockwise) need not be represented differently. This can similarly apply for focal sources and sinks. Distinguishing these visually is a simple matter of superimposing velocity vector arrows. As the type of clique (center, side, or corner) determines the maximum score and certainty, this can also be represented. The highest scores can be visually represented as fully opaque (or near so) and the lowest scores most translucent. Alternatively, stippling to various levels could be used. The colors of the color triangle 701 can fade from one color to the other colors as the color triangle is moved along from one corner to another. As an example, when moving along an outer axis of the triangle from red 703 to green 705, the color triangle 701 can show a brief amount of orange before turning to yellow 709. The color triangle can further turn from yellow 709 to a yellow-green, before moving to green 705 as the green corner of the color triangle 701 is reached.

Figure 33:
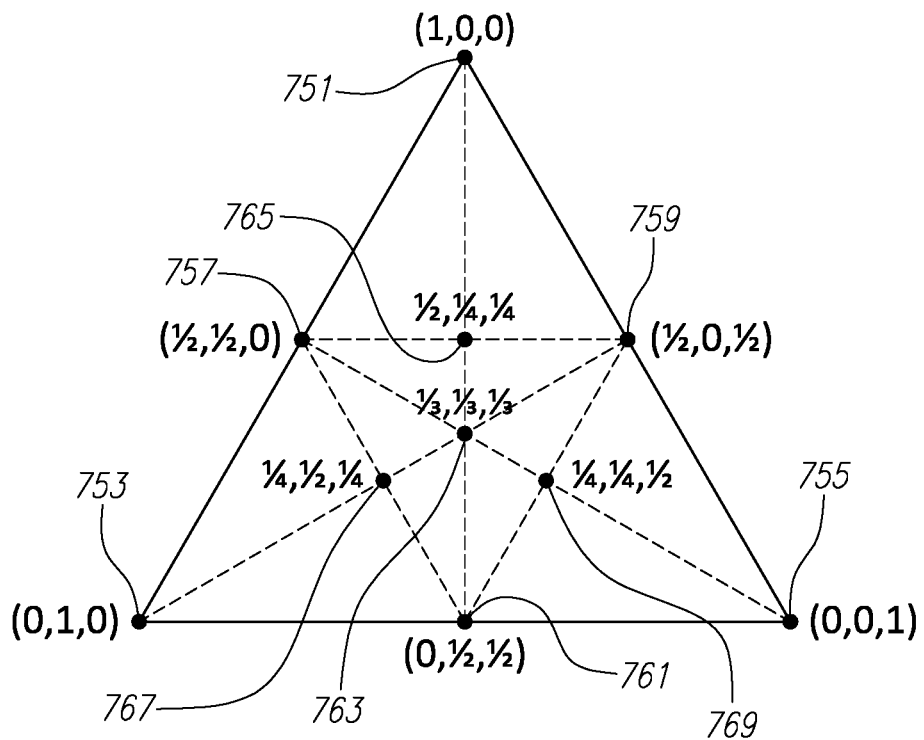
FIG. 33 is a diagram of barycentric coordinates from normalized scores to govern the displayed color shown in FIG. 32.

In some embodiments a module to translate from the 3 scores for each template type to a location on the 2D triangle above can still be needed. FIG. 33 illustrates one embodiment of a way of doing this. Barycentric coordinates from normalized scores govern the choice of displayed color. As illustrated, (1,0,0) is at the top 751, (0,0,1) is at the bottom right 755 of the triangle, and (0,1,0) is at the bottom left 753 of the triangle. An example of the color triangle in use can include a center clique evaluated to the following set of scores (recall the maximum is 8): (5,5,0) representing the degree of match to rotor, uniform, or focal conduction in that order. The scores are normalized by dividing this triple by the L1 norm (sum of absolute values) to obtain (0.5,0.5,0) 761. This is recognized as specifying yellow on the color triangle above. The level of translucency of yellow is determined by ratio of the L∞ norm (the maximum absolute value) here 5, to its maximum possible value 8. As a result, a translucency/opacity score of 5/8 denotes moderate certainty. If the scores had been (8,0,0) the perfect match to a rotor would result in a color triangle value of (1,0,0) and a translucency (or better said opacity) score of 1.0 for complete certainty. Further combinations of the triangle include (0.5,0.25,0.25) 765, (0.5,0,0.5) 759, (0.33,0.33,0.33) 763, (0.25,0.5,0.25) 767, (0.25,0.25,0.5) 769, and (0,0.5,0.5) 761.

Searching for a rotor center or focal source is facilitated by the beat-by-beat colored display. If for example, a rotor is sought, one moves the paddle catheter about until a corner or edge obtains a reddish hue. The whole paddle is then moved in that direction until the center clique is as red as possible and the surrounding clique colors are red-tinged.

Figure 34:
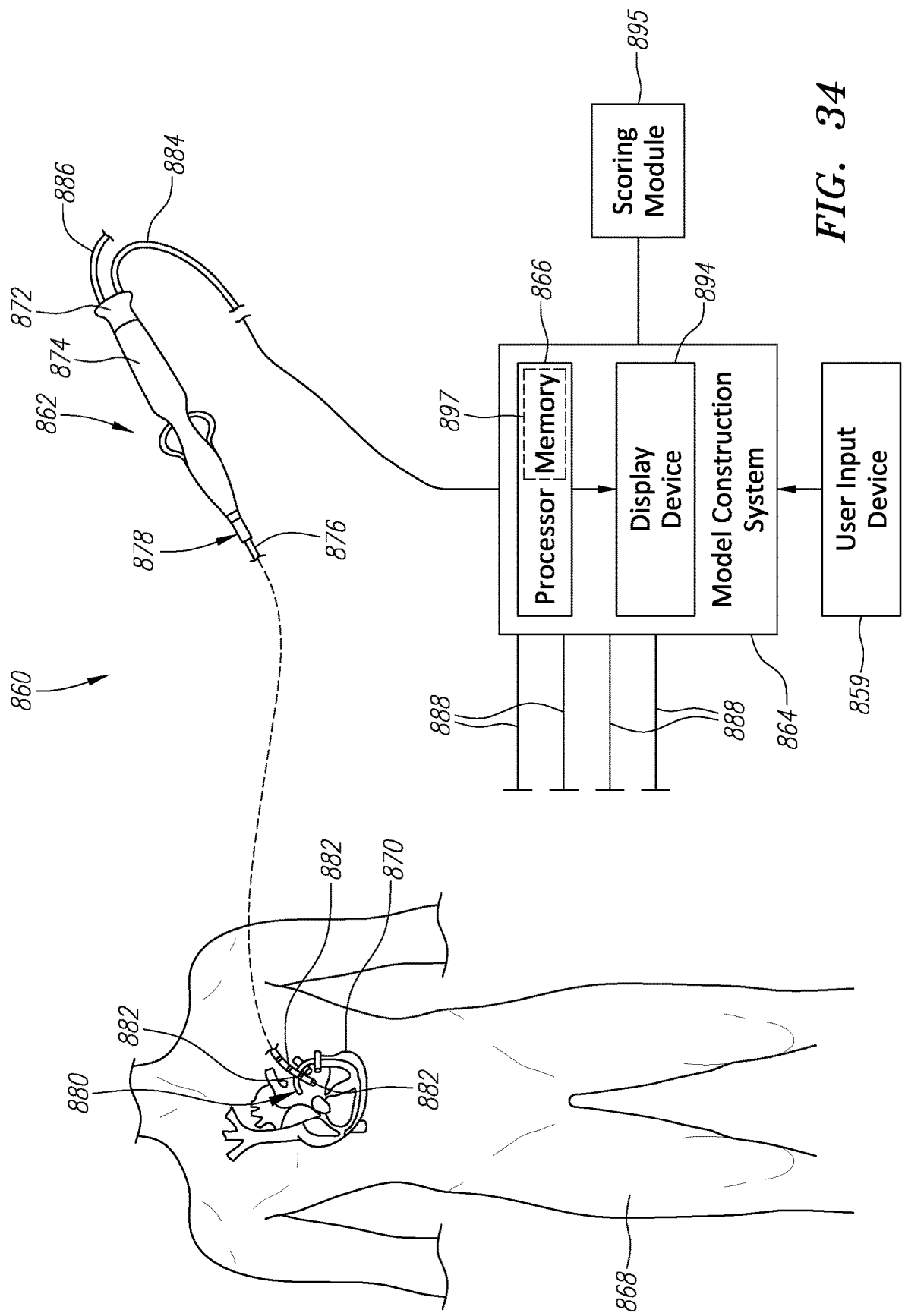
FIG. 34 is a diagrammatic view of a system for generating surface models and/or mapping electrophysiological information thereon and determining a scoring system for a set of cliques.

FIG. 34 illustrates an embodiment of a system 860 comprising a scoring module 895 as described above that can compute and output a scoring system for collected data. The system 860 comprises, among other components, a medical device 862 and a model construction system 864. In one embodiment, the medical device 862 comprises a catheter, and the model construction system 864 comprises, in part, a processing apparatus 866. The processing apparatus 866 may take the form of an electronic control unit, for example, that is configured to obtain a geometry surface model of the cardiac structure, and to construct an EP map corresponding to the cardiac structure using data collected by, for example, the catheter 862. The model construction system 864 can further be coupled to a scoring module 895 that can process the score of any clique as described above and output that information to a display device 894. In one embodiment, the scoring module 895 can be a software program loaded on to the model construction system 864. In other embodiments, the scoring module 895 can be a separate piece of hardware communicatively coupled to the model construction system 864. The catheter 862 is configured to be inserted into a patient's body 868, and more particularly, into the patient's heart 870. The catheter 862 may include a cable connector or interface 872, a handle 874, a shaft 876 having a proximal end 878 and a distal end 880 and one or more sensors 882 mounted in or on the shaft 876 of the catheter 862. In one embodiment, the sensors 882 are disposed at or near the distal end 880 of the shaft 876. The connector 872 provides mechanical, fluid, and electrical connection(s) for cables, such as, for example, cables 884, 886 extending to the model construction system 864 and/or other components of the system 860 (e.g., a visualization, navigation, and/or mapping system (if separate and distinct from the model construction system 864), an ablation generator, irrigation source, etc.).

The sensors 882 mounted in or on the shaft 876 of the catheter 862 are electrically connected to the model construction system 864, and the processing apparatus 866 thereof, in particular. The sensors 882 may be provided for a variety of diagnostic and therapeutic purposes including, for example and without limitation, EP studies, pacing, cardiac mapping, and ablation. In an one embodiment, one or more of the sensors 882 are provided to perform a location or position sensing function. Accordingly, in such an embodiment, as the catheter 862 is moved along a surface of the cardiac structure and/or about the interior thereof, the sensor(s) 882 can be used to collect location data points that correspond to the surface of, or locations within, the cardiac structure. These location data points can then be used by, for example, the model construction system 864 in the construction of a geometry surface model of the cardiac structure.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

What is claimed is:

1. A system for determining electrophysiological data comprising:
   an electronic control unit configured to:
   acquire electrophysiology signals from a plurality of electrodes of one or more catheters;
   select at least one clique of electrodes from the plurality of electrodes to determine a plurality of local electric (E) field data points, wherein the at least one clique of electrodes comprises three electrodes;
   process the electrophysiology signals from the at least one clique to derive the plurality of local E field data points associated with the at least one clique of electrodes, wherein each of the electrodes comprising the at least one clique of electrodes is associated with at least one of the plurality of local E field data points;
   derive at least one orientation-independent bipolar electrophysiology signal from the plurality of local E field data points associated with the at least one clique of electrodes; and
   output catheter-orientation-independent electrophysiologic information to a user or process.

2. The system according to claim 1, wherein the electronic control unit is further configured to determine the location and orientation of the plurality of electrodes.

3. The system according to claim 2, wherein the electronic control unit is further configured to use at least one criteria to determine whether each of the at least one clique is in contact with a target surface.

4. The system according to claim 3, wherein the at least one criteria comprises at least one of an angular deviation, the characteristics of tangent bipole vector (Et), and a scalar version of Et along a unit activation direction (Ea) from a clique of the at least one clique.

5. The system according to claim 3, wherein the at least one criteria comprises an amplitude of a unipolar signal obtained from each of the electrodes in a clique of the at least one clique and the morphology of unipolar signals obtained from the electrodes in the clique of the at least one clique.

6. The system according to claim 3, wherein the electronic control unit is configured to receive one or more criteria from the user or process to determine whether each of the at least one clique is in contact with the target surface.

7. The system according to claim 1, wherein the catheter-orientation-independent electrophysiologic information output by the electronic control unit is beat-by-beat information.

8. The system according to claim 1, wherein the electronic control unit is further configured to:
   weight the E field data points; and
   derive the orientation-independent electrophysiologic information from the weighted E field data points.

9. The system according to claim 8, wherein the electronic control unit is configured to derive at least one of a substrate voltage amplitude, local activation timing, or conduction velocity from the weighted E field data points.

10. The system according to claim 8, wherein the plurality of E field data points form an E field loop, and wherein the electronic control unit is further configured to weight each of the E field data points based on the distance of point in the E field from an isoelectric origin.

11. The system according to claim 8, wherein the plurality of E field data points form an E field loop, and wherein the electronic control unit is further configured to weight the data points in the E field loop based on |d/dt(E(t))|.

12. The system according to claim 8, wherein the plurality of E field data points form an E field loop, and wherein the weight of the E field data points is determined from a weighting function that increases the weight in a region corresponding to the zero-crossing of Ea.

13. The system according to claim 1, wherein the at least one clique of electrodes comprises a plurality of adjacent cliques.

14. The system according to claim 13, wherein the electronic control unit is further configured to compute a local velocity vector for each of the plurality of adjacent cliques.

15. The system according to claim 14, wherein the electronic control unit is further configured to determine a divergence and curl path integral and a path length.

16. The system according to claim 14, wherein the electronic control unit is further configured to determine whether a uniform propagation, a rotor, a focal source, a collision site, or a scar is present within the plurality of adjacent cliques.

17. The system according to claim 16, wherein the electronic control unit is further configured to score each of the plurality of adjacent cliques.

18. The system according to claim 17, wherein the electronic control unit is further configured to compare the score of each of the plurality of adjacent cliques to at least one template.

19. The system according to claim 13, wherein the electronic control unit is configured to calculate a score for a target clique from at least one clique adjacent to the target clique.

20. A method for determining electrophysiological data comprising:
   acquiring electrophysiology signals from a plurality of electrodes of one or more catheters;
   selecting at least one clique of electrodes from the plurality of electrodes to determine a plurality of local E field data points, wherein the at least one clique comprises three electrodes;
   processing the electrophysiology signals from the at least one clique to derive the plurality of local E field data points associated with the at least one clique of electrodes, wherein each of the electrodes comprising the at least one clique of electrodes is associated with at least one of the plurality of local E field data points;
   deriving at least one orientation-independent bipolar electrophysiology signal from the plurality of local E field data points associated with the at least one clique of electrodes; and
   outputting catheter-orientation-independent electrophysiologic information to a user or process.

* * * * *